US008778365B1

(12) United States Patent
Hardas et al.

(10) Patent No.: US 8,778,365 B1
(45) Date of Patent: Jul. 15, 2014

(54) TOPICAL COMPOSITIONS AND METHODS FOR MAKING AND USING SAME

(71) Applicant: Merz Pharmaceuticals, LLC, Greensboro, NC (US)

(72) Inventors: Bhushan Hardas, Summerville, NC (US); Donna Dalton, High Point, NC (US)

(73) Assignee: Merz Pharmaceuticals, LLC, Greensboro, NC (US)

( * ) Notice: Subject to any disclaimer, the term of this patent is extended or adjusted under 35 U.S.C. 154(b) by 0 days.

(21) Appl. No.: 13/756,392

(22) Filed: Jan. 31, 2013

(51) Int. Cl.
A61K 9/00 (2006.01)
A61K 9/14 (2006.01)
A61K 31/74 (2006.01)
A01N 25/32 (2006.01)
A61K 47/38 (2006.01)

(52) U.S. Cl.
CPC ..................................... A61K 47/38 (2013.01)
USPC ......... 424/400; 424/406; 424/484; 424/78.07

(58) Field of Classification Search
CPC .................................. A61K 9/06; A61K 8/042
USPC .............................. 424/400, 406, 484, 78.07
See application file for complete search history.

(56) References Cited

U.S. PATENT DOCUMENTS

| 5,661,170 | A * | 8/1997 | Chodosh ..................... 514/390 |
| 6,231,837 | B1 | 5/2001 | Stroud et al. |
| 7,740,875 | B2 | 6/2010 | Dechow |
| 2002/0045667 | A1 | 4/2002 | Baker, Jr. et al. |
| 2003/0027845 | A1 | 2/2003 | Marfat et al. |
| 2003/0206958 | A1 | 11/2003 | Cattaneo et al. |
| 2004/0261190 | A1 | 12/2004 | Eggenweiler et al. |
| 2005/0059686 | A1 | 3/2005 | Eggenweiler et al. |
| 2005/0176714 | A1 | 8/2005 | Eggenweiler et al. |
| 2005/0209240 | A1 | 9/2005 | Eggenweiler et al. |
| 2005/0222160 | A1 | 10/2005 | Eggenweiler et al. |
| 2005/0276842 | A1 | 12/2005 | Zhang et al. |
| 2006/0034902 | A1 * | 2/2006 | Cormier et al. ............... 424/448 |
| 2006/0078599 | A1 | 4/2006 | Ebmeier et al. |
| 2006/0234981 | A1 | 10/2006 | Baker et al. |
| 2006/0280795 | A1 | 12/2006 | Penhasi et al. |
| 2007/0020196 | A1 | 1/2007 | Pipkin et al. |
| 2007/0027153 | A1 | 2/2007 | Reeth et al. |
| 2007/0071705 | A1 | 3/2007 | De Oliveira et al. |
| 2007/0154402 | A1 | 7/2007 | Trumbore et al. |
| 2007/0189977 | A1 | 8/2007 | Zhang et al. |
| 2007/0189978 | A1 | 8/2007 | Zhang et al. |
| 2007/0189980 | A1 | 8/2007 | Zhang et al. |
| 2007/0190124 | A1 | 8/2007 | Zhang et al. |
| 2007/0196293 | A1 | 8/2007 | Zhang et al. |
| 2007/0196323 | A1 | 8/2007 | Zhang et al. |
| 2007/0196325 | A1 | 8/2007 | Zhang et al. |
| 2007/0196452 | A1 | 8/2007 | Zhang et al. |
| 2007/0196453 | A1 | 8/2007 | Zhang et al. |
| 2007/0196457 | A1 | 8/2007 | Zhang et al. |
| 2007/0196458 | A1 | 8/2007 | Zhang et al. |
| 2007/0196459 | A1 | 8/2007 | Zhang et al. |
| 2007/0269379 | A1 | 11/2007 | Mitragotri et al. |
| 2008/0019927 | A1 | 1/2008 | Zhang et al. |
| 2008/0107742 | A1 | 5/2008 | Hare |
| 2008/0188568 | A1 | 8/2008 | Suvanprakorn et al. |
| 2008/0206161 | A1 | 8/2008 | Tamarkin et al. |
| 2009/0175945 | A1 | 7/2009 | Zhang et al. |
| 2009/0227541 | A1 | 9/2009 | Baker et al. |
| 2009/0247529 | A1 | 10/2009 | Lindahl et al. |
| 2010/0267678 | A1 | 10/2010 | Zhang et al. |
| 2011/0182835 | A1 | 7/2011 | Caetano et al. |
| 2011/0305646 | A1 | 12/2011 | Lenn et al. |
| 2012/0128612 | A1 | 5/2012 | Lenn et al. |
| 2012/0294907 | A1 | 11/2012 | Zhang et al. |
| 2012/0294926 | A1 | 11/2012 | Zhang et al. |
| 2012/0301517 | A1 | 11/2012 | Zhang et al. |
| 2013/0022564 | A1 | 1/2013 | Zhang et al. |

FOREIGN PATENT DOCUMENTS

| WO | WO-2005120473 A2 | 12/2005 |
| WO | WO2007054085 A | 5/2007 |
| WO | WO2007094999 A | 8/2007 |
| WO | WO2008064345 A | 5/2008 |
| WO | WO2009054992 A | 4/2009 |
| WO | WO-2009089361 A2 | 7/2009 |
| WO | WO2010124280 A | 10/2010 |
| WO | WO-2011014850 A2 | 2/2011 |
| WO | WO-2011073392 A1 | 6/2011 |
| WO | WO-2011073395 A1 | 6/2011 |

OTHER PUBLICATIONS

Del Rosso et al. (Cutis. Mar. 2008 81(3): 209-14; abstract only).*
Antifungals, Topical Review, Provider Synergies, L.L.C., 1-16 (2010).
Gold, M.H. et al., An Open-Label Study of Naftifine Hydrochloride 1% Gel in the Treatment of Tinea Versicolor, SkinMed Dermatology for the Clinician, 9(5):283-286 (2011).
Barakat, Heba S., et al., Development of Naftifine Hydrochloride Alcohol-Free Niosome Gel, Drug Development and Industrial Pharmacy, 35:631-367 (2009).
Drug @ FDA, NAFTIN (Jun. 18, 1990).
Drugs.com, Loprox Gel (Jul. 21, 1997).

* cited by examiner

Primary Examiner — Johann R Richter
Assistant Examiner — Genevieve S Alley
(74) Attorney, Agent, or Firm — Choate, Hall & Stewart LLP; Andrea L. C. Reid; Danielle M. Nihan

(57) ABSTRACT

The present invention relates to improved topical gel compositions comprising an active agent, and uses thereof.

17 Claims, 2 Drawing Sheets

TOPICAL COMPOSITIONS AND METHODS FOR MAKING AND USING SAME

FIELD

The present subject matter relates to improved topical pharmaceutical compositions comprising an active agent, and methods of making and using same to treat, ameliorate, or prevent a condition.

BACKGROUND

Topical compositions may be used to deliver an active agent for the treatment of various conditions and diseases. Formulating topical compositions presents several challenges. For example, it may be difficult to formulate topical compositions that will cause less irritation upon application of the same as compared to other topical compositions comprising the same active agent or active agents. In addition, it may also be difficult to prepare storage stable topical compositions that cause little or no irritation. Accordingly, there remains a need to develop more effective topical treatments.

SUMMARY

The present invention provides an improved gel composition for topical treatment. Provided formulations comprise an active agent, as described in detail herein. Methods of utilizing a provided formulation are described herein.

DETAILED DESCRIPTION OF THE INVENTION

Figure 1:
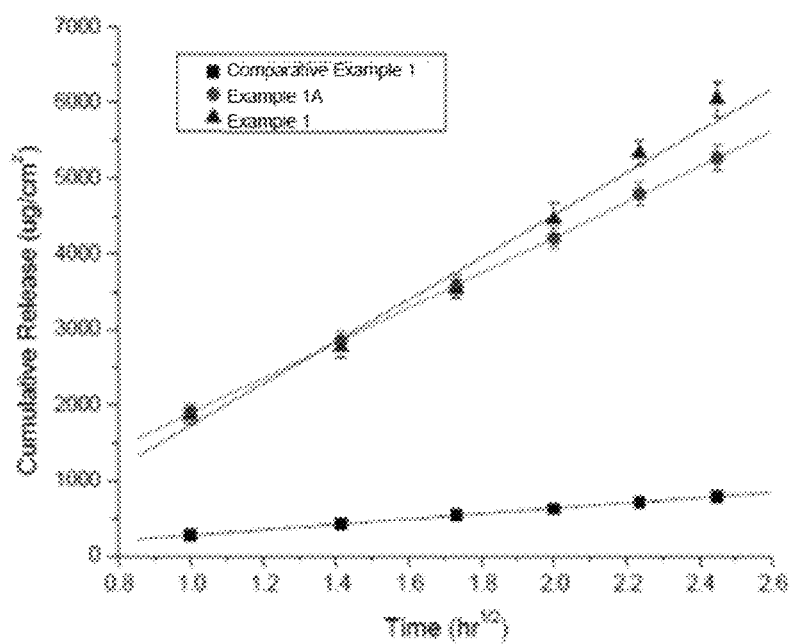
FIG. 1 is a graphical representation of the results obtained from a release assay in vitro test.
Figure 2:
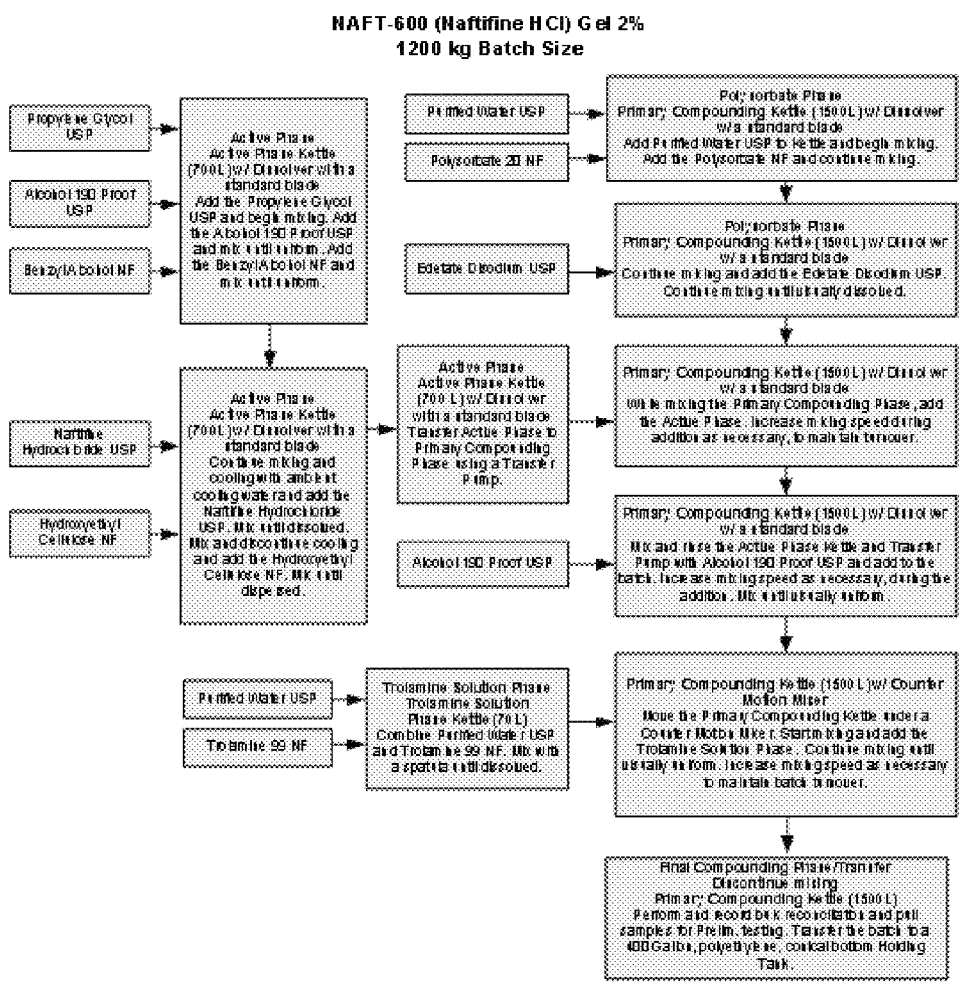
FIG. 2 is a flow chart illustrating a representative process for manufacturing provided gel compositions.

As described above, there remains a need for improved topical gel compositions that are significantly more effective than known topical antifungal pharmaceutical compositions. The present invention provides gel compositions with surprisingly improved delivery of an active agent, which improved delivery allows for less frequent dosing and/or a shorter course of treatment. In some embodiments, compositions described herein dramatically reduce irritation or stinging associated with existing formulations. Further, in some embodiments, presently described gel compositions are effective for treating, inter alia, moccasin-type *Tinea pedis*, which was, heretofore, generally only effectively treated by an oral antifungal medication.

Gel Compositions:

In some embodiments, gel compositions of the present invention are comprised of:
  (i) a first solvent;
  (ii) optionally a second solvent;
  (iii) a non-carbomer rheology modifier;
  (iv) an active agent;
  (v) optionally one or more solubizing agents; and
optionally one or more of: a diluent, a preservative, a pH adjuster, a chelating agent, a coloring agent, and a fragrance. Exemplary such gel compositions are described in further detail below and herein.

In some embodiments, the present invention provides a gel composition, wherein the composition does not comprise a carbomer.

In some embodiments, the present invention provides a gel composition, wherein the gel composition is a water soluble gel composition. In some embodiments, the present invention provides a gel composition, wherein the gel composition is not a water soluble gel composition.

In some embodiments, a provided gel composition has a viscosity or average viscosity of from about 30,000 to about 100,000 Centipoise ("cP"); from about 40,000 to about 90,000 cP; from about 50,000 to about 80,000 cP; from about 55,000 to about 75,000 cP; from about 55,000 to about 70,000 cP; from about 60,000 to about 70,000 cP; or from about 60,000 to about 66,000 cP.

In some embodiments, a provided gel composition has a viscosity or average viscosity of from about 55,000 to about 70,000 centipoise (cP).

In some embodiments, a provided gel composition has a viscosity or average viscosity of from about 30,000 to about 100,000 centipoise (cP).

Definitions:

As used herein, the terms "administer," "administering," and "administration," refer to any method which, in sound medical practice, delivers a provided composition, or an active agent contained therein, to a subject in such a manner as to provide a therapeutic effect.

The phrase "candidal onychomycosis" as used herein refers to a fungal yeast infection of the fingernails and/or toenails caused by a *Candida* spp., including for example, *Candida albicans* and *Candida parapsilosis*.

The term "carbomer" as used herein refers to a polymer of acrylic acid cross-linked with a polyfunctional compound, hence, a poly (acrylic acid) or polyacrylate.

The term "chelating agent" as used herein refers to any known pharmaceutically acceptable chelating agents. Suitable chelating agents can include but are not limited to any one or more of ethylenediaminetetraacetic acid(EDTA) and derivatives thereof, ethylene glycol-bis-(2-aminoethyl)-N,N,N',N'-tetraacetic acid (EGTA) and derivatives thereof, cyclohexanediamine tetraacetic acid (CDTA) and derivatives thereof, hydroxyethylethylenediamine triacetic acid (HEDTA) and derivatives thereof, diethylenetriamine pentaacetic acid (DTPA) and derivatives thereof, dimercaptopropane sulfonic acid (DMPS) and derivatives thereof, dimercaptosuccinic acid (DMSA) and derivatives thereof, aminotrimethylene phosphonic acid (ATPA) and derivatives thereof, N,N-bis(carboxymethyl)glycine (NTA) and derivatives thereof, nitrilotriacetic acid and derivatives thereof, citric acid and derivatives thereof, niacinamide and derivatives thereof, sodium desoxycholate and derivatives thereof, polyphosphates; porphine; and any pharmaceutically acceptable salts thereof.

As used herein, the term "dermatomycosis" refers to a fungal infection of the skin caused by a dermatophyte.

As used herein, the term "diluent" refers to water or saline.

As used herein, the phrases an "effective amount" or a "therapeutically effective amount" of an active agent or ingredient, or pharmaceutically active agent or ingredient, refer to an amount of the pharmaceutically active agent sufficient enough to have a therapeutic effect upon administration. Effective amounts of the pharmaceutically active agent will vary with the kind of pharmaceutically active agent chosen, the particular condition or conditions being treated, the severity of the condition, the duration of the treatment, the specific components of the composition being used, and like factors. For example, the presently described compositions can be topically applied in an amount sufficient to cover an affected area plus a margin of healthy skin or tissue surrounding the affected area, for example, a margin of about 0.5 inches, at a frequency, for example, of once a day, for a time period, for example of about two weeks.

As used herein, the phrase "fungal infection" refers to any superficial fungal infection, including for example, one or more of a superficial fungal infection of the skin, onychomycosis, and a fungal infection of a hair follicle, each of which is as defined herein. Such fungal infections can include superficial fungal infections of the skin, including for example, one or more of *Tinea cruris, Tinea corporis*, interdigital *Tinea pedis*, moccasin-type *Tinea pedis, Tinea manuum, Tinea versicolor* (pityriasis), *Tinea nigra*, cutaneous candidiasis, *Tinea faciei*, and white and black piedra; fungal infections of the hair follicle including one or more of *Tinea capitis, Tinea Favose* (favus), and *Tinea barbae*; and onychomycosis, a fungal infection of one or more of the nail bed, matrix, and nail plate, caused by, for example, dermatophytes, yeasts, and non-dermatophyte molds.

As used herein, the phrase "fungal infection of the hair follicle" refers to a fungal infection of at least the tubular in folding of the epidermis (skin) containing the root of a hair of any one or more of the scalp, eyebrows, eyelashes, and bearded area of an individual. The phrase "fungal infection of the hair follicle" also refers to a fungal infection of the tubular infolding of the epidermis (skin) containing the root of a hair of any one or more of the scalp, eyebrows, eyelashes, and bearded area, along with a fungal infection of the hair shaft, of an individual. Such fungal infections can include, for example, one or more of *Tinea capitis, Tinea favosa*, and *Tinea Barbae*. The term "hair follicle" refers to a tubular infolding of the epidermis (skin) containing the root of a hair. The follicle is lined by cells derived from the epidermal layer of the skin. *Tinea capitis* (or severe highly-inflammatory cases sometimes termed Kerion) is a superficial fungal infection (dermatophytosis) of the skin of the scalp, eyebrows, and eyelashes, that attacks the hair follicles and shaft. The disease is primarily caused by dermatophytes in the *Trichophyton* and *Microsporum* genera, including for example, *Microsporum audouini, Microsporum canis, Microsporum distortum, Microsporum gypseum, Trichophyton megninii, Trichophyton mentagrophytes, Trichophyton rubrum, Trichophyton schoenleinii, Trichophyton tonsurans*, and *Trichophyton verrucosum*. The clinical presentation is typically a single or multiple patches of hair loss, sometimes with a 'black dot' pattern (often with broken-off hairs), that may be accompanied by inflammation, scaling, pustules, and itching. *Tinea favosa* can be considered a variety of *Tinea capitis* because it involves the scalp; however, it may also involve glabrous skin and nails. *Tinea favosa* is primarily caused by dermatophytes in the *Trichophyton* and *Microsporum* genera, including for example, *Microsporum gypseum* and *Trichophyton schoenleinii*. *Tinea barbae* is a superficial dermatophytosis that is limited to the bearded areas of the face, neck, chin, cheeks, and/or lips and occurs almost exclusively in older adolescent and adult males. The clinical presentation of *Tinea barbae* includes inflammatory, deep, kerion-like plaques and non-inflammatory superficial patches resembling *Tinea corporis* or bacterial folliculitis. The mechanism that causes *Tinea barbae* is similar to that of *Tinea capitis*, and is frequently the result of a *Trichophyton rubrum* (*T. rubrum*) infection but may also be the result of *Trichophyton mentagrophytes* var *granulosum* and *Trichophyton verrucosum*. Finally *Microsporum canis* and *Trichophyton mentagrophytes* var *erinacei* have been known to cause *Tinea barbae* but are relatively rare.

As used herein, the term "infection" refers to the invasion, development and/or multiplication of a microorganism within or on another organism. An infection may be localized to a specific region of an organism or systemic.

The phrase "non-carbomer rheology modifier/thickener" as used herein refers to any known rheology modifier/thickener that is not a carbomer. Suitable non-carbomer rheology modifiers/thickeners can include but are not limited to hydroxy celluloses, semi-synthetic polymers including carboxymethyl cellulose and starch; natural polysaccharides including but not limited to guar gum, locust bean gum, xanthan, chitosan and alginate. Suitable hydroxy celluloses include hydroxyethyl cellulose (HEC), hydroxymethyl cellulose (HMC), hydroxypropyl cellulose (HPC), hydroxypropylmethyl cellulose (HPMC), and hydroxyethylmethyl cellulose (HEMC).

The phrase "non-irritating," as used herein, refers to the presently described topical pharmaceutical compositions, including for example, the presently described gel topical pharmaceutical compositions, that elicit reduced irritation, for example, reduced burning and/or stinging, in a subject, for example, as compared to the irritation elicited by known topical pharmaceutical compositions. For example, less than 5% of subjects treated with the presently described topical pharmaceutical composition report irritation due to application of the pharmaceutical composition, i.e., burning and/or stinging; less than 4% of subjects treated with the presently described topical pharmaceutical composition report irritation due to application of the pharmaceutical composition; less than 3% of subjects treated with the presently described topical pharmaceutical composition report irritation due to application of the pharmaceutical composition; less than 2% of subjects treated with the presently described topical pharmaceutical composition report irritation due to application of the pharmaceutical composition; or less than 1% of subjects treated with the presently described topical pharmaceutical composition report irritation due to application of the pharmaceutical composition. See the Examples and comparative Examples described herein. As used herein the term "pH adjuster" refers to any pharmaceutically acceptable composition, compound, or agent, suitable for adjusting the pH of the presently described topical pharmaceutical compositions without negatively affecting any property thereof. Suitable pH adjusters can include any pharmaceutically acceptable acid or base. Suitable pH adjusters can include but are not limited to hydrochloric acid, sulfuric acid, citric acid, acetic acid, formic acid, phosphoric acid, tartric acid, trolamine, sodium hydroxide and potassium hydroxide.

The phrase "occlusive dressing or covering" as used herein refers to any porous or non-porous dressing or covering that may retain moisture and/or heat, and/or may increase the concentration and/or absorption of the active agent being topically applied. Suitable occlusive coverings can include, for example, a bandage, wrap, coban-type dressings, silicone-type bandages, foam bandages, duct tape, plastic wrap, latex, rubber, or other non-permeable material, a commercially available adhesive bandage, gauze, a patch, an adhesive patch, a sock, and/or a glove or mitten.

The term "onychomycosis" as used herein refers to a fungal infection of the nail bed, matrix, and/or or nail plate. Onychomycosis is caused by three main classes of fungi: dermatophytes, yeasts (candidal onychomycosis), and non-dermatophyte molds. Dermatophytes are the most common cause of onychomycosis. Onychomycosis caused by non-dermatophyte molds is becoming more common worldwide. Onychomycosis due to *Candida* is less common. Dermatophytes that can cause onychomycosis include one or more of *Trichophyton rubrum, Trichophyton interdigitale, Epidermophyton floccosum, Trichophyton violaceum, Microsporum*

*gypseum, Trichophyton tonsurans, Trichophyton soudanense,* and *Trichophyton verrucosum,* and such disease is often also referred to as *Tinea ungium.* Candidal onychomycosis include cutaneous candidisis and mucocutaneous candidiasis, that are caused by one or more *Candida* species, including for example, *Candida albicans* and *Candida parapsilosis.* Non-dermatophyte molds that can cause onychomycosis can include one or more of, for example, *Scopulariopsis brevicaulis, Fusarium* spp., *Aspergillus* spp., *Alternaria, Acremonium, Scytalidinum dimidiatum,* and *Scytalidinium hyalinum.* There are four classic types of onychomycosis including the following: distal and lateral subungal onychomycosis (DLSO) that is the most common form of onychomycosis, and is usually caused by *Trichophyton rubrum* and/or *Trichophyton interdigitale,* which invades the nail bed and the underside of the nail plate; white superficial onychomycosis (WSO) is caused by fungal (e.g., *T. mentagrophytes*) invasion of the superficial layers of the nail plate to form "white islands" on the plate, non-dermatophyte molds cause deep white superficial onychomycosis; proximal subungal onychomycosis (PSO) is fungal penetration of the newly formed nail plate through the proximal nail fold and it is the least common form of onychomycosis in healthy people, but is found more commonly when the patient is immunocompromised; endonyx onychomycosis (EO), and candidal onychomycosis (CO) which is *Candida* species invasion of the fingernails.

As used herein, the phrase "pharmaceutically acceptable salts" refers to salts of certain ingredient(s) which possess the same activity as the unmodified compound(s) and which are neither biologically nor otherwise undesirable. A salt can be formed with, for example, organic or inorganic acids. Such suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids.

As used herein the term "preservative" refers to any known pharmaceutically acceptable preservative that functions by inhibiting bacteria, fungi, yeast, mold, other microbe, and/or by inhibiting oxidation. Suitable preservatives include but are not limited to antimicrobial agents and/or antioxidants. Suitable antimicrobial agents can include but are not limited to benzoates, benzyl alcohol, sodium benzoate, sorbates, propionates, and nitrites. Suitable antioxidants can include but are not limited to vitamin C, butylated hydroxytoluene (BHT), sulphites, and vitamin E.

The term "prevent," "preventing," or "prevention," as used herein refers to any reduction, no matter how slight, of a subject's predisposition or risk for developing a condition, disease, disorder or symptom thereof. For purposes of prevention, the subject is any subject, and preferably is a subject that is at risk for, or is predisposed to, developing a condition, disease, disorder. The term "prevention" includes either preventing the onset of a clinically evident condition, disease, disorder altogether or preventing the onset of a pre-clinically evident condition, disease, disorder in individuals at risk. This includes prophylactic treatment of subjects at risk of developing condition, disease, disorder.

As used herein, the term "solvent" refers to any pharmaceutically acceptable medium which is a liquid at ambient temperature, in which one or more solutes can be dissolved, or one or more substances can be partially dissolved or suspended, which medium is present in a provided composition in an amount of about 10 wt % or more. Numerous solvents are well known in the chemical and pharmaceutical arts and are contemplated herein and below.

As used herein, the term "solubilizing agent" refers to any pharmaceutically acceptable liquid medium, surfactant, and/or emulsifier that is present in a provided composition in an amount of less than about 10 wt %. One of skill in the chemical and pharmaceutical arts will readily appreciate that certain of the above-described solvents may also be used in substantially lower amounts such that they are characterized herein as solubilizing agents rather than solvents. Accordingly, in some embodiments, a solubilizing agent is any one of the above-listed solvents present in a provided formulation in an amount less than 10 wt % of the formulation. For example, in some embodiments, a solubilizing agent is a dialkylene glycol monoalkyl ether, such as, e.g., diethylene glycol monoethyl ether, present in an amount of less than 10 wt %. In some embodiments, a solubilizing agent is an alcohol, for instance, ethanol, present in an amount less than 10 wt %. Exemplary other such solubilizing agents are described below and herein.

The phrase "substantially pure" as used herein refers to an individual compound form, which is substantially devoid of all other forms, as well as degradation products of a form, and any residual solvent, and is at least 85% pure on a % weight basis, unless otherwise specified. The compound form can have at least 90% purity on a % weight basis, at least 93% purity on a % weight basis, at least 95% purity on a % weight basis, or at least 97%, 98%, 99%, or 99.5% purity on a % weight basis.

As used herein, "subject" or "individual" or "animal" or "patient" or "mammal," refers to any subject, particularly a mammalian subject, for whom diagnosis, prognosis, or therapy is desired, for example, a human.

As used herein, the term "superficial fungal infection of the skin" refers to a fungal infection present on the outer layer of skin, including *Tinea cruris* (jock itch), *Tinea corporis* (ringworm), *Tinea pedis,* interdigital *Tinea pedis,* moccasin-type *Tinea pedis, Tinea manuum, Tinea versicolor* (piyriasis), *Tinea nigra,* cutaneous candidiasis, *Tinea faciei* (facial ringworm), and white and black piedra. *Tinea corporis* (body ringworm), *Tinea cruris* (jock itch), and *Tinea faciei* (facial ringworm), can be caused by *Epidermophyton floccosum, Microsporum canis, Trichophyton mentagrophytes, T. rubrum, T. tonsurans, T. verrucosum,* and/or *T. violaceum. Tinea pedis* (athlete's foot) or *Tinea manuum* (fungal infection of the hand), are caused by *Epidermophyton floccosum, Microsporum canis, Trichophyton mentagrophytes, T. rubrum, T. tonsurans, T. verrucosum,* and/or *T. violaceum.* Cutaneous candidiasis can be caused by *C. albicans.*

As used herein, a "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. A useful composition herein needs only to reduce the severity of a disease, disorder, or condition, reduce the severity of symptoms associated therewith, provide improvement to a patient or subject's quality of life, or delay or inhibit the onset of a disease, disorder, or condition.

As used herein, all percentages are by weight of the total composition (i.e., wt %), unless otherwise specified.

Any concentration ranges, percentage range, or ratio range recited herein are to be understood as expressly disclosing and including any concentrations, percentages or ratios of any integer within that range and fractions thereof, such as one tenth and one hundredth of an integer, and any sub-range falling within a range, unless otherwise indicated.

Any number range recited herein relating to any physical feature, including for example, polymer subunits, size or thickness, are to be understood as expressly disclosing and including any integer or fraction of an integer within a disclosed range, or any sub-range within a disclosed range, unless otherwise indicated.

For the purpose of clarity, any element or feature of any method or composition or process described herein, can be combined with any other element or feature of any other method or composition or process described herein.

Other terms as used herein are meant to be defined by their well-known meanings in the art.

Solvents

As defined above, a gel composition of the present invention comprises one or more solvents as described above and defined herein. For instance, in some embodiments, a provided gel composition comprises only one solvent, such as a glycol solvent (e.g., propylene glycol) or an alkyl alcohol solvent (e.g., ethanol). In other embodiments, a gel composition of the present invention comprises more than one solvent. In some embodiments wherein a gel composition of the present invention comprises more than one solvent, the present invention refers to one of the more than one solvents as a "first solvent" and another of the more than one solvents as a "second solvent." In such instances, by "first solvent" is meant any of the solvents described above and herein; by "second solvent" is meant any of the solvents described above and herein other than the "first solvent." Likewise, also contemplated herein are additional solvents, e.g., a "third solvent," a "fourth solvent," etc., which solvents are also characterized in that each is a different solvent from the others. In some embodiments, a first or second solvent is, for example, a glycol solvent. In some embodiments, a first or second solvent is, for example, an alcohol solvent. Exemplary such one or more solvents, and combinations thereof, are contemplated by the present invention and described herein.

In some embodiments, a solvent is an alcohol solvent. In certain embodiments, the alcohol solvent is an alkyl alcohol. Exemplary such alcohol solvents include, but are not limited to, one or more of methanol, ethanol, n-propyl alcohol, iso-propyl alcohol, n-butyl alcohol, t-butyl alcohol, 2-butanol, iso-butanol, pentanol, hexanol, cyclohexanol, and hexadecan-1-ol. In some embodiments, the alcohol solvent is methanol, ethanol, n-propyl alcohol, or isopropyl alcohol. In certain embodiments, the alcohol solvent is ethanol. In some embodiments, a solvent is a mixture of one or more such alcohols.

As used herein and unless otherwise indicated, the term "ethanol" refers to 190 proof USP grade ethanol. In some embodiments, USP grade ethanol is ethanol containing NLT 92.3% and NMT 93.8%, by weight, corresponding to NLT 94.9% and NMT 96.0%, by volume, at 15.56°, of $C_2H_5OH$.

In some embodiments, a solvent is, e.g., a triacetin and/or diol and/or polyol solvent. Diol solvents can include, but are not limited to, glycol solvents. In certain embodiments, a solvent is an alkylene glycol solvent. For instance, in some embodiments, the alkylene glycol solvent is ethylene glycol, propylene glycol, butylene glycol, or the like. In certain embodiments, the glycol solvent is propylene glycol.

In some embodiments, a solvent is a glycol ether. For instance, in some embodiments, a solvent is a dialkylene glycol monoalkyl ether, such as, e.g., diethylene glycol monoethyl ether. Other such glycol ethers are known in the chemical and pharmaceutical arts and are contemplated by the present invention.

In some embodiments, a solvent is present in a gel composition in an amount greater than 10 wt % to about 50 wt %; from greater than 10 wt % to about 45 wt %; from greater than 10 wt % to about 35 wt %; from greater than 10 wt % to about 30 wt %; from greater than 10 wt % to about 25 wt %; from greater than 10 wt % to about 20 wt %; from greater than 10 wt % to about 15 wt %; from about 15 wt % to about 30 wt %; from about 15 wt % to about 25 wt %; from about 15 wt % to about 20 wt %; from about 20 wt % to about 45 wt %; from about 25 wt % to about 45 wt %; from about 30 wt % to about 40 wt %; from about 16 wt % to about 24 wt %; from about 17 wt % to about 23 wt %; from about 18 wt % to about 24 wt %; from about 18 wt % to about 23 wt %; from about 18 wt % to about 22 wt %; from about 18 wt % to about 21 wt %; from about 18 wt % to about 20 wt %; from about 18.5 wt % to about 19.5 wt %; from about 19 wt % to about 20 wt %; from about 19 wt % to about 21 wt %; from about 19 wt % to about 22 wt %; from about 19 wt % to about 23 wt %; from about 19 wt % to about 24 wt %; from about 19 wt % to about 25 wt %; about 11 wt %; about 12 wt %; about 13 wt %; about 14 wt %; about 15 wt %; about 16 wt %; about 17 wt %; about 18 wt %; about 19 wt %; about 20 wt %; about 21 wt %; about 22 wt %; about 23 wt %; about 24 wt %; about 25 wt %; about 26 wt %; about 27 wt %; about 28 wt %; about 29 wt %; about 30 wt %; about 31 wt %; about 32 wt %; about 33 wt %; about 34 wt %; about 35 wt %; about 36 wt %; about 37 wt %; about 38 wt %; about 39 wt %; about 40 wt %; about 41 wt %; about 42 wt %; about 43 wt %; about 44 wt %; or about 45 wt %.

In some embodiments, a solvent is present in a gel composition in an amount of from about 16 wt % to about 24 wt %. In some embodiments, a solvent is present in a gel composition in an amount of from about 17 wt % to about 23 wt %. In some embodiments, a solvent is present in a gel composition in an amount of from about 18 wt % to about 22 wt %. In some embodiments, a solvent is present in a gel composition in an amount of from about 18 wt % to about 21 wt %. In certain embodiments, a solvent is present in a gel composition in an amount of about 18 wt %. In certain embodiments, a solvent is present in a gel composition in an amount of about 19 wt %. In certain embodiments, a solvent is present in a gel composition in an amount of about 20 wt %.

In some embodiments, a solvent is present in a gel composition in an amount of from about 20 wt % to about 45 wt %. In some embodiments, a solvent is present in a gel composition in an amount of from about 25 wt % to about 45 wt %. In some embodiments, a solvent is present in a gel composition in an amount of from about 30 wt % to about 45 wt %. In some embodiments, a solvent is present in a gel composition in an amount of from about 35 wt % to about 45 wt %. In some embodiments, a solvent is present in a gel composition in an amount of about 35 wt %; about 36 wt %; about 37 wt %; about 38 wt %; about 39 wt %; about 40 wt %; about 41 wt %; about 42 wt %; about 43 wt %; about 44 wt %; or about 45 wt %. In certain embodiments, a solvent is present in a gel composition in an amount of about 41%.

In certain embodiments, a gel composition of the present invention comprises more than one solvent, wherein at least one of the more than one solvents is a glycol solvent.

In certain embodiments, a gel composition of the present invention comprises more than one solvent, wherein at least one of the more than one solvents is an alcohol solvent.

In certain embodiments, a gel composition of the present invention comprises more than one solvent, wherein at least one of the more than one solvents is an alcohol solvent and one of the more than one solvents is a glycol solvent. In certain embodiments, an alcohol solvent and a glycol solvent are each present in an amount of about 15 wt % to about 35 wt %. In certain embodiments, an alcohol solvent and a glycol solvent are each present in an amount of about 15 wt % to about 30 wt %. In certain embodiments, an alcohol solvent and a glycol solvent are each present in an amount of about 15 wt % to about 25 wt %. In certain embodiments, an alcohol solvent and a glycol solvent are each present in an amount of about 18 wt % to about 21 wt %. In some embodiments, the alcohol solvent is an alkyl alcohol (e.g., ethanol) present in an amount of about 15-25 wt % and the glycol solvent is an alkylene glycol (e.g., propylene glycol) present in an amount of about 15-25 wt %. In some embodiments, the alcohol solvent is ethanol and is present in an amount of about 18-20 wt % and the glycol solvent is propylene glycol and is present in an amount of about 18-20 wt %.

Solubilizing Agent:

In some embodiments, a gel composition of the present invention comprises one or more solubilizing agents as described above and defined herein. For instance, in some embodiments, the one or more solubilizing agent is a polysorbate solubilizing agent. In some embodiments, the one or more solubilizing agent is an alcohol solubilizing agent. In some embodiments, the one or more solubilizing agent is a dialkylene glycol monoalkyl ether solubilizing agent. Exemplary solubilizing agents are described below and herein.

In some embodiments, a solubilizing agent is a suitable surfactant or emulsifier. Suitable surfactants or emulsifiers include one or more non-ionic surfactants, PEG-80 sorbitan laurate (2,3-dihydroxypropyl octanoate) (e.g., TWEEN 28), a polyoxyethylene co-solvent, and polysorbate surfactants/emulsifiers.

In some embodiments, a solubilizing agent is a suitable surfactant. In certain embodiments, a suitable surfactant is a polysorbate. Exemplary polysorbate solubilizing agents include, but are not limited to, Polysorbate 20 (polyoxyethylen-(20)-sorbitanmonolaurate), Polysorbate 21 (polyoxyethylen-(4)-sorbitanmonolaurate), Polysorbate 25, Polysorbate 40 (polyoxyethylen-(20)-sorbitanmonopalmitate), Polysorbate 41, Polysorbate 45, Polysorbate 60 (polyoxyethylen-(20)-sorbitanmonostearate), Polysorbate 61 (polyoxyethylen-(4)-sorbitanmonostearate), Polysorbate 65 (polyoxyethylen-(20)-sorbitantristearate), Polysorbate 80 (polyoxyethylen-(20)-sorbitanmonooleate), Polysorbate 81 (polyoxyethylen-(5)-sorbitanmonooleate), Polysorbate 85 (polyoxyethylen-(20)-sorbitantrioleate), Polysorbate 120 (polyoxyethylen-(20)-sorbitanmonoisostearate), Polysorbate 121, and Polysorbate 125.

In certain embodiments, the polysorbate solubilizing agent is Polysorbate 20 (polyoxyethylen-(20)-sorbitanmonolaurate), Polysorbate 40 (polyoxyethylen-(20)-sorbitanmonopalmitate), Polysorbate 60 (polyoxyethylen-(20)-sorbitanmonostearate), Polysorbate 65 (polyoxyethylen-(20)-sorbitantristearate), or Polysorbate 80 (polyoxyethylen-(20)-sorbitanmonooleate).

In certain embodiments, the polysorbate solubilizing agent is Polysorbate 20 (polyoxyethylen-(20)-sorbitanmonolaurate). In certain embodiments, the polysorbate solubilizing agent is Polysorbate 80 (polyoxyethylen-(20)-sorbitanmonooleate).

In some embodiments, a solubilizing agent is a glycol ether. In some embodiments, asolubilizing agent is a dialkylene glycol monoalkyl ether. In certain embodiments, a solubilizingsolubilizing agent is diethylene glycol monoethyl ether. In some embodiments, a solubilizing agent is a glycol ether present in an amount of less than about 8 wt %. In some embodiments, a solubilizing agent is a glycol ether present in an amount of less than about 7 wt %. In some embodiments, a solubilizing agent is a glycol ether present in an amount of less than about 6 wt %. In some embodiments, a solubilizing agent is a glycol ether present in an amount of less than about 5 wt %. In some embodiments, a solubilizingsolubilizing agent is a glycol ether, e.g., diethylene glycol monoethyl ether, present in an amount ranging from about 0.5 wt % to about 3.0 wt %.

In some embodiments, it is highly desirable that a provided gel composition elicit reduced irritation, for example, reduced burning and/or stinging, in a subject, for example, as compared to the irritation elicited by known topical pharmaceutical compositions. Accordingly, in some embodiments, the presently described gel compositions do not comprise an alcohol solvent. Rather, in certain embodiments, a gel composition of the present invention comprises alcohol in a reduced amount, for instance as a solubilizing agent. In certain embodiments, a gel composition of the present invention comprises one or more solubilizing agents, wherein at least one solubilizingsolubilizing agent is a polysorbate solubilizing agent and at least one solubilizing agent is an alcohol solubilizing agent. In certain embodiments, a gel composition of the present invention comprises one or more solubilizing agents, wherein at least one solubilizingsolubilizing agent is a polysorbate solubilizing agent and at least one solubilizing agent is a dialkylene glycol monoalkyl ether solubilizing agent. In some embodiments, a gel composition of the present invention comprises a polysorbate solubilizing agent, an alcohol solubilizing agent, and optionally a third solubilizing agent. For instance, in certain embodiments, a gel composition of the present invention comprises a polysorbate solubilizing agent (e.g., Polysorbate 20), an alcohol solubilizing agent (e.g., an alkyl alcohol solvent such as ethanol), and a dialkylene glycol monoalkyl ether solubilizing agent (e.g., diethylene glycol monoethyl ether). Exemplary other such one or more solubilizing agents, and combinations thereof, are contemplated by the present invention and are described herein.

In some embodiments, the solubilizingsolubilizing agent is present in an amount of about 0.5 wt %. In some embodiments, a solubilizingsolubilizing agent is present in an amount of about 0.75 wt %. In some embodiments, a solubilizingsolubilizing agent is present in an amount of about 1.0 wt %. In some embodiments, a solubilizingsolubilizing agent is present in an amount of about 1.25 wt %. In some embodiments, a solubilizingsolubilizing agent is present in an amount of about 1.5 wt %. In some embodiments, a solubilizingsolubilizing agent is present in an amount of about 1.75 wt %. In some embodiments, a solubilizingsolubilizing agent is present in an amount of about 2.0 wt %. In some embodiments, a solubilizingsolubilizing agent is present in an amount of about 2.25 wt %. In some embodiments, a solubilizingsolubilizing agent is present in an amount of about 2.5 wt %. In some embodiments, a solubilizingsolubilizing agent is present in an amount of about 2.75 wt %. In some embodiments, a solubilizingsolubilizing agent is present in an amount of about 3.0 wt %. In some embodiments, a solubilizingsolubilizing agent is present in an amount of about 3.25 wt %. In some embodiments, a solubilizingsolubilizing agent is present in an amount of about 3.5 wt %. In some embodiments, a solubilizingsolubilizing agent is present in an amount of about 3.75 wt %. In some embodiments, a solubilizingsolubilizing agent is present in an amount of about 4.0 wt %. In some embodiments, a solubilizingsolubilizing agent is present in an amount of about 4.25 wt %. In some embodiments, a solubilizingsolubilizing agent is present in an amount of about 4.5 wt %. In some embodiments, a solubilizingsolubilizing agent is present in an amount of about 4.75 wt %. In some embodiments, a solubilizingsolubilizing agent is present in an amount of about 5.0 wt %. In some embodiments, a solubilizingsolubilizing agent is present in an amount of about 6.0 wt %. In some embodiments, a solubilizingsolubilizing agent is present in an amount of about 7.0 wt %. In some embodiments, a solubilizing agent is present in an amount of about 8.0 wt %. In some embodiments, a solubilizing agent is present in an amount of about 9.0 wt %. In some embodiments, a solubilizing agent is present in an amount of less than about 10.0 wt %.

In some embodiments, a solubilizing agent is present in an amount ranging from about 0.5 wt % to about 3.0 wt %. In some embodiments, a solubilizing agent is present in an amount ranging from about 1.0 wt % to about 2.0 wt %. In some embodiments, a solubilizing agent is present in an amount of about 1.5 wt %.

In some embodiments, a solubilizing agent is present in an amount ranging from about 4.0 wt % to about 9.0 wt %. In some embodiments a solubilizing agent is present in an amount ranging from about 4.5 wt % to about 9.0 wt %. In some embodiments, a solubilizing agent is present in an amount ranging from about 5.0 wt % to about 9.0 wt %. In some embodiments, a solubilizing agent is present in an amount of about 5.0 wt %. In some embodiments, a solubilizing agent is present in an amount of about 8.0 wt %. In certain embodiments, a solubilizing agent is an alcohol solubilizing agent, e.g., ethanol, and is present in an amount of about 8.0 wt %.

Non-Carbomer Rheology Moder:

The non-carbomer rheology modifier for use in the presently described gel compositions can include any known rheology modifier/thickener that is not a carbomer.

In some embodiments, the non-carbomer rheology modifier for use in the presently described gel compositions can include any known rheology modifier/thickener that is not an alkyl cellulose, e.g., ethyl cellulose.

Suitable non-carbomer rheology modifiers/thickeners include hydroxy celluloses, semi-synthetic polymers including but not limited to carboxymethyl cellulose and starch; natural polysaccharides including but not limited to guar gum, locust bean gum, xanthan, chitosan and alginate. Suitable hydroxy celluloses hydroxyethyl cellulose (HEC), hydroxymethyl cellulose (HMC), hydroxypropyl cellulose (HPC), hydroxyethylmethyl cellulose (HEMC), and hydroxypropylmethyl cellulose (HPMC).

In some embodiments, the non-carbomer rheology modifier is hydroxyethyl cellulose (HEC) and is present in a described gel composition in an amount ranging from about 1.5 wt % to about 2.0 wt %. In certain embodiments, the hydroxyethylcelluose is present in an amount of about 1.75 wt %.

One of skill in the relevant chemical and pharmaceutical arts will appreciate that hydroxycelluloses are available in a variety of chain lengths and that the amount required by a particular formulation may vary depending on, inter alia, the chain length of the selected hydroxycellulose. In some embodiments, the HEC has a viscosity of between 100 and 25000 mPa's. In certain embodiments, the HEC has a viscosity of between 1500-2500 mPa's.

The described non-carbomer rheology modifiers/thickeners can be present in the described gel compositions in an amount of from >0.5 wt % to about 4 wt %; from >0.5 wt % to about 3 wt %; from >0.5 wt % to about 2.5 wt %; from >0.5 wt % to about 2 wt %; from >0.5 wt % to about 2.25 wt %; from >0.5 wt % to about 2 wt %; from about 0.5 wt % to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.7 wt % to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.9 wt % to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 1 wt % to about 4 wt %; from about 1 wt % to about 3.5 wt %; from about 1 wt % to about 3 wt %; from about 1 wt % to about 2.5 wt %; from about 1 wt % to about 2.25 wt %; from about 1.1 wt % to about 2.3 wt %; from about 1.3 wt % to about 2.3 wt %; from about 1.4 wt % to about 1.7 wt %; from about 1.4 wt % to about 1.8 wt %; from about 1.4 wt % to about 1.9 wt %; from about 1.4 wt % to about 2 wt %; from about 1.4 wt % to about 2.1 wt %; from about 1.4 wt % to about 2.2 wt %; from about 1.4 wt % to about 2.3 wt %; from about 1.5 wt % to about 1.8 wt %; from about 1.5 wt % to about 1.9 wt %; from about 1.5 wt % to about 2 wt %; from about 1.5 wt % to about 2.1 wt %; from about 1.5 wt % to about 2.2 wt %; from about 1.5 wt % to about 2.3 wt %; from about 1.6 wt % to about 1.8 wt %; from about 1.6 wt % to about 1.9 wt %; from about 1.6 wt % to about 2 wt %; from about 1.6 wt % to about 2.1 wt %; from about 1.6 wt % to about 2.2 wt %; from about 1.6 wt % to about 2.3 wt %; from about 1.65 wt % to about 1.75 wt %; from about 1.65 wt % to about 1.85 wt %; from about 1.7 wt % to about 1.8 wt %; from about 1.7 wt % to about 1.9 wt %; from about 1.7 wt % to about 2 wt %; from about 1.7 wt % to about 2.1 wt %; from about 1.7 wt % to about 2.2 wt %; from about 1.7 wt % to about 2.3 wt %; from about 1.7 wt % to about 2.25 wt %; about 1.7 wt %; or about 1.75 wt % non-carbomer rheology modifier.

Preservatives:

The preservatives for use in the presently described gel compositions can include those described herein, including any known pharmaceutically acceptable preservative that functions by inhibiting bacteria and/or fungi, and/or by inhibiting oxidation. Suitable preservatives can include but are not limited to antimicrobial agents and/or antioxidants. Suitable antimicrobial agents can include but are not limited to benzoates, benzyl alcohol, sodium benzoate, sorbates, propionates, and nitrites. Suitable antioxidants can include but are not limited to vitamin C, butylated hydroxytoluene (BHT), sulphites, and vitamin E, as well as any known pharmaceutically acceptable preservative. In certain embodiments, the preservative is benzyl alcohol.

The described preservatives and/or antioxidants can be present in the described gel compositions in an amount of, for example, from about 0.001 wt % to about 15 wt %; from about 0.01 wt % to about 5 wt %; from about 0.2 wt % to about 4 wt %; from about 0.3 wt % to about 4 wt %; from about 0.4 wt % to about 4 wt %; from about 0.5 wt % to about 4 wt %; from about 0.6 wt % to about 4 wt %; from about 0.7 wt % to about 3 wt %; from about 0.8 wt % to about 2 wt %; from about 0.9 wt % to about 1.5 wt %; from about 0.9 wt % to about 1.1 wt %; about 0.9 wt %; about 1 wt %; or about 1.1 wt % preservative.

In certain embodiments, a gel composition of the present invention comprises benzyl alcohol in an amount ranging from about 0.9 wt % to about 1.1 wt %. In certain embodiments, a gel composition of the present invention comprises benzyl alcohol in an amount of about 1.0 wt %. In some embodiments, benzyl alcohol is absent from a gel composition of the present invention.

pH Adjusters:

pH adjusters for use in the presently described gel compositions can include any pharmaceutically acceptable composition, compound, or agent, suitable for adjusting the pH of the presently described topical pharmaceutical compositions without negatively affecting any property thereof. Suitable pH adjusters can include any pharmaceutically acceptable acid or base. Suitable pH adjusters include those described herein.

In some embodiments, gel compositions of the present invention comprise a basic pH adjuster. For example, in certain embodiments, the pH adjuster is an amine base. Exemplary such amine bases are known in the chemical and pharmaceutical arts and include, e.g., triethanolamine (i.e., Trolamine). In certain embodiments, a gel composition of the present invention comprises from about 0.12 wt % to about 0.23 wt % triethanolamine. In certain embodiments, a gel composition of the present invention comprises from about 0.14 wt % to about 0.21 wt % triethanolamine. In certain embodiments, a gel composition of the present invention comprises from about 0.15 wt % to about 0.20 wt % triethanolamine. In certain embodiments, a gel composition of the present invention comprises from about 0.16 wt % to about 0.19 wt % triethanolamine. In certain embodiments, a gel composition of the present invention comprises about 0.17 wt % triethanolamine.

In some embodiments, a basic pH adjuster is hydroxide. In certain embodiments, the hydroxide is in the form of a salt of an alkali or alkaline earth metal. For instance, in some embodiments, a hydroxide salt is sodium hydroxide, potassium hydroxide, or calcium hydroxide. In some embodiments, a pH adjuster is carbonate. In certain embodiments, the carbonate is in the form of a salt of an alkali or alkaline earth metal. For instance, in some embodiments, a carbonate salt is sodium carbonate, potassium carbonate, or calcium carbonate. Exemplary other such hydroxide and carbonate bases and the like are well-known in the chemical and pharmaceutical arts and contemplated herein.

The described pH adjusters can be present in a described gel compositions in an amount of from >0.01 wt % to about 1 wt %; from >0.05 wt % to about 1 wt %; from about 0.05 wt % to about 0.5 wt %; from about 0.08 wt % to about 0.4 wt %; from about 0.08 wt % to about 0.35 wt %; from about 0.08 wt % to about 0.3 wt %; from about 0.08 wt % to about 0.25 wt %; from about 0.09 wt % to about 0.4 wt %; from about 0.09 wt % to about 0.3 wt %; from about 0.09 wt % to about 0.25 wt %; from about 0.1 wt % to about 0.25 wt %; from about 0.11 wt % to about 0.24 wt %; from about 0.12 wt % to about 0.23 wt %; from about 0.13 wt % to about 0.22 wt %; from about 0.14 wt % to about 0.21 wt %; from about 0.15 wt % to about 0.2 wt %; from about 0.16 wt % to about 0.19 wt %; from about 0.16 wt % to about 0.18 wt %; from about 0.165 wt % to about 0.175 wt %; about 0.16 wt %; about 0.17 wt %; or about 0.18 wt % pH adjuster.

In some embodiments, a presently described gel composition has a pH of from about 4.0 to about 7.5; from about 4.0 to about 7.0; from about 4.0 to about 6.5; from about 4.0 to about 6.0; from about 4.5 to about 6.5; from about 4.5 to about 6.0; from about 4.5 to about 5.5; from about 4.7 to about 5.5; from about 4.8 to about 5.4; or from about 4.7 to about 5.5, from about 4.9 to about 5.3; from about 4.5 to about 6.0; from about 4.6 to about 5.9; from about 4.7 to about 5.8; from about 4.8 to about 5.7; from about 4.9 to about 5.6; from about 5.0 to about 5.4; from about 5.1 to about 5.3; from about 5.5 to about 7.5; from about 5.6 to about 7.4; from about 5.7 to about 7.3; from about 5.8 to about 7.2; from about 5.9 to about 7.1; from about 6.0 to about 7.0; from about 6.1 to about 6.9; from about 6.2 to about 6.8; from about 6.3 to about 6.7; from about 6.4 to about 6.6; about 4.5; about 4.6; about 4.7; about 4.8; about 4.9; about 5.0; about 5.1; about 5.2; about 5.3; about 5.4; about 5.5; about 5.6; about 5.7; about 5.8; about 5.9; about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. For example, the pH of the presently described gel composition comprising 2 wt % active agent, for example naftifine hydrochloride at 23° C.±2° C. can be from about 4.5 to about 6.0. In some embodiments, a presently described gel composition has a pH of from about 6.5 to about 8.5. In some embodiments, a presently described gel composition has a pH of about 6.5, about 6.6, about 6.7, about 6.7, about 6.8, about 6.9, about 7.0, about 7.1, about 7.2, about 7.3, about 7.5, about 7.5, about 7.6; about 7.7; about 7.8; about 7.9; about 8.0; about 8.1; about 8.2; about 8.3; about 8.4; or about 8.5. For example, the pH of the presently described gel composition comprising 0.025 wt % active agent, for example fluticasone propionate at 23° C.±2° C. can be from about 7.5 to about 8.5.

Chelating Agents:

Chelating agents for use in the presently described gel compositions can include any known pharmaceutically acceptable chelating agents. Suitable chelating agents can include but are not limited to any one or more of ethylenediaminetetraacetic acid(EDTA), cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccinic acid (DMSA), aminotrimethylene phosphonic acid (ATPA), polyphosphates; porphine; and any pharmaceutically acceptable salt thereof. In certain embodiments, a suitable chelating agent is disodium EDTA (i.e., edetate disodium).

The described chelating agents can be present in the described topical pharmaceutical compositions in an amount of, for example, from about 0.001 wt % to about 10 wt %; from about 0.005 wt % to about 5 wt %; from about 0.005 wt % to about 0.5 wt %; from about 0.001 wt % to about 1 wt %; from about 0.01 to about 5 wt %; from about 0.006 wt % to about 0.04 wt %; from about 0.007 wt % to about 0.035 wt %; from about 0.008 wt % to about 0.035 wt %; from about 0.009 wt % to about 0.035 wt %; from about 0.01 wt % to about 0.03 wt %; from about 0.015 wt % to about 0.025 wt %; from about 0.018 wt % to about 0.022 wt %; from about 0.019 wt % to about 0.021 wt %; about 0.019 wt %; about 0.02 wt %; or about 0.021 wt % chelating agent.

In certain embodiments, a gel composition of the present invention comprises from about 0.01 wt % to about 0.03 wt % disodium EDTA (i.e., edetate disodium). In certain embodiments, a gel composition of the present invention comprises from about 0.015 wt % to about 0.025 wt % disodium EDTA (i.e., edetate disodium). In certain embodiments, a gel composition of the present invention comprises from about 0.017 wt % to about 0.023 wt % disodium EDTA (i.e., edetate disodium). In certain embodiments, a gel composition of the present invention comprises about 0.02 wt % disodium EDTA (i.e., edetate disodium).

Active Agents

The presently described pharmaceutical compositions may comprise an active agent and/or a pharmaceutically acceptable salt thereof. The active agent may be present in the topical pharmaceutical compositions in an amount of from 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01% to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; from about 3 wt % to about 5 wt %; from about 3 wt % to about 4.5 wt %; from about 3 wt % to about 4 wt %; from about 3 wt % to about 3.5 wt %; or in any other amount within any of the above ranges.

In some embodiments, the active agent or pharmaceutically acceptable salt thereof may be present in the topical pharmaceutical compositions in an amount of from 0.01 wt % to about 1.0 wt %; from about 0.01 wt % to about 0.9 wt %; from about 0.01 wt % to about 0.85 wt %; from about 0.01 wt % to about 0.8 wt %; from about 0.01 wt % to about 0.75 wt %; from about 0.01 wt % to about 0.70 wt %; from about 0.01 wt % to about 0.65 wt %; from about 0.01 wt % to about 0.60 wt %; from about 0.01 wt % to about 0.55 wt %; from about 0.01 wt % to about 0.50 wt %; from about 0.01 wt % to about 0.45 wt %; from about 0.01 wt % to about 0.40 wt %; from about 0.01 wt % to about 0.35 wt %; from about 0.01 wt % to about 0.30 wt %; from about 0.01 wt % to about 0.25 wt %; from about 0.01 wt % to about 0.20 wt %; from about 0.01 wt % to about 0.15 wt %; from about 0.01 wt % to about 0.10 wt %; from about 0.015 wt % to about 0.1 wt %; from about 0.02 wt % to about 0.1 wt %; from about 0.025 wt % to about 0.1 wt %; from about 0.03 wt % to about 0.1 wt %; from about 0.035 wt % to about 0.1 wt %; from about 0.04 wt % to about 0.1 wt %; from about 0.045 wt % to about 0.1 wt %; from about 0.05 wt % to about 0.1 wt %; from about 0.06 wt % to about 0.1 wt %; from about 0.07 wt % to about 0.1 wt %; from about 0.08 wt % to about 0.1 wt %; from about 0.09 wt % to about 0.1 wt %; or in any other amount within any of the above ranges.

In some embodiments, the active agent or pharmaceutically acceptable salt thereof is present in a gel composition in an amount of from about 0.01 wt % to about 0.06 wt %; from about 0.015 wt % to about 0.055 wt %; from about 0.015 wt % to about 0.05 wt %; or from about 0.02 wt % to about 0.05 wt %. In some embodiments, the active agent or pharmaceutically acceptable salt thereof may be present in an amount of about 0.025 wt %. In some embodiments, the active agent or pharmaceutically acceptable salt thereof may be present in an amount of about 0.05 wt %. In some embodiments the active agent or pharmaceutically acceptable salt thereof may be present in an amount of about 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, or 0.1 wt %.

The described active agent and/or a pharmaceutically acceptable salt thereof can be present in a gel composition of the present invention in an amount of from about 0.05 wt % to about 6.0 wt %, of from about 0.1 wt % to about 6.0 wt %, of from about 0.5 wt % to about 6.0 wt %, of from about 0.6 wt % to about 6.0 wt %, of from about 0.7 wt % to about 6.0 wt %, of from about 0.8 wt % to about 6.0 wt %, of from about 0.9 wt % to about 6.0 wt %, of from about 1.0 wt % to about 6.0 wt %, of from about 1.5 wt % to about 6.0 wt %, of from about 2.0 wt % to about 6.0 wt %, of from about 2.5 wt % to about 6.0 wt %, of from about 3.0 wt % to about 6.0 wt %, of from about 3.5 wt % to about 6.0 wt %, of from about 4.0 wt % to about 6.0 wt %, of from about 4.5 wt % to about 6.0 wt %, of from about 5.0 wt % to about 6.0 wt %, of from about 5.5 wt % to about 6.0 wt %, of from about 0.05 wt % to about 3.0 wt %, of from about 0.1 wt % to about 2.9 wt %, of from about 0.2 wt % to about 2.7 wt %, of from about 0.3 wt % to about 2.5 wt %, of from about 0.4 wt % to about 2.3 wt %, of from about 0.5 wt % to about 2.1 wt %, of from about 0.6 wt % to about 1.9 wt %, of from about 0.7 wt % to about 1.7 wt %, of from about 0.8 wt % to about 1.5 wt %, of from about 0.9 wt % to about 1.3 wt %, of from about 1 wt % to about 1.1 wt %, of from about 0.05 wt % to about 1.0 wt %, of from about 0.06 wt % to about 1.0 wt %, of from about 0.07 wt % to about 1.0 wt %, of from about 0.08 wt % to about 1.0 wt %, of from about 0.09 wt % to about 1.0 wt %, of from about 0.1 wt % to about 1.0 wt %, of from about 0.15 wt % to about 1.0 wt %, of from about 0.2 wt % to about 1.0 wt %, of from about 0.25 wt % to about 1.0 wt %, of from about 0.3 wt % to about 1.0 wt %, of from about 0.35 wt % to about 1.0 wt %, of from about 0.4 wt % to about 1.0 wt %, of from about 0.45 wt % to about 1.0 wt %, of from about 0.5 wt % to about 1.0 wt %, of from about 0.55 wt % to about 1.0 wt %, of from about 0.6 wt % to about 1.0 wt %, of from about 0.65 wt % to about 1.0 wt %, of from about 0.7 wt % to about 1.0 wt %, of from about 0.75 wt % to about 1.0 wt %, of from about 0.8 wt % to about 1.0 wt %, of from about 0.85 wt % to about 1.0 wt %, of from about 0.9 wt % to about 1.0 wt %, of from about 0.95 wt % to about 1.0 wt %, of from about 0.5 wt % to about 4.0 wt %, of from about 0.75 wt % to about 4.0 wt %, of from about 1 wt % to about 4.0 wt %, of from about 1.25 wt % to about 4.0 wt %, of from about 1.5 wt % to about 4.0 wt %, of from about 2 wt % to about 4.0 wt %, of from about 2.25 wt % to about 4.0 wt %, of from about 2.5 wt % to about 4.0 wt %, of from about 2.75 wt % to about 4.0 wt %, of from about 3 wt % to about 4.0 wt %, of from about 3.75 wt % to about 4.0 wt %, of from about 1.5 wt % to about 3.0 wt %, from about 1.5 wt % to about 2.5 wt %, from about 1.6 wt % to about 2.4 wt %, from about 1.7 wt % to about 2.3 wt %, from about 1.75 wt % to about 2.25 wt %, from about 1.8 wt % to about 2.2 wt %, from about 1.9 wt % to about 2.1 wt %, about 2.0 wt %, about 2.5 wt %, from about 1.9 wt % to about 3.0 wt %, from about 2.0 wt % to about 3.0 wt %, from about 2.1 wt % to about 3.0 wt %, from about 2.2 wt % to about 3.0 wt %, from about 2.3 wt % to about 3.0 wt %, from about 2.4 wt % to about 3.0 wt %, from about 2.5 wt % to about 3.0 wt %, from about 2.6 wt % to about 3.0 wt %, from about 2.7 wt % to about 3.0 wt %, from about 2.8 wt % to about 3.0 wt %, from about 2.9 wt % to about 3.0 wt %, about 3.0 wt %, 2.0 wt %, 2.5 wt %, or 3.0 wt %.

Antibacterial Agents

In some embodiments, the active agent or pharmaceutically acceptable salt thereof is an antibacterial agent. In some embodiments, the antibacterial agent is, for example, bacitracin, polymyxin (B), neomycin, muprirocin, retapamulin, gentamycin, silver sulfadiazine, benzol peroxide, hydrogen peroxide, clindamycin phosphate, erythromycin, minocycline, doxycyclinemetronidazole, azelaic acid, sodium sulfacetamide, sodium sulfacetamide sulfur, dapsone (diamino-diphenyl sulfone), neramexane, penicillins, cephalosporins, carbapenems, monobactams, chloramphenicol, fluoroquinolones, tetracyclines, glycylcylines, macrolides, ketolide (telithromycin), daptomycin, linezolid, metronidazole, dalfopristin-quinupristin, trimethoprim-sulfamethoxazole, spectinomycin, vancomycin, fosfomycin, cycloserine, lincosamides, aminoglycosides, colistin, novobiocin, metronidazole, sulfonamides, capreomycin, and kanamycin.

In some embodiments, an active agent or pharmaceutically acceptable salt thereof is an antiseptic agent including, e.g., detergents, bleaches, triclosan, chlorohexidine and povidone/iodine.

Antifungal Agents

In some embodiments, the active agent or pharmaceutically acceptable salt thereof is an antifungal agent. For example, in some embodiments, the antifungal agent is a polyene, an azole, an allylamine (for instance, naftifine or terbinafine) a benzyl amine (for instance, butenafine), or other antifungal agents (for instance, amorolfine). Examples of polylenes include, e.g., nystatin and Amphotericin B. Examples of azoles include miconazole, clotrimazole, ketoconazole, oxiconazole, eberconazole, econazole, sulconazole and sertaconazle bifonazole, butoconazole, fenticonazole, isoconazole, omoconazole and tioconazole, or pharmaceutically acceptable salts thereof. Exemplary other antifungals include naftifine, terbinafine and butenafine, or pharmaceutically acceptable salts. Still other antifungal agents include, e.g., ciclopirox or selenium sulfide. Additional antifungals include agents that block NA synthesis including, e.g., flucytosine, and those that disrupt microtubule function including, e.g., griseofulvin. Suitable antifungals can include one of candicidin, filipin, hamycin, natamycin, and rimocidin. Triazoles, including albaconazole, fluconazole, isavuconazole, itraconazole, posaconazole, ravuconazole, terconazole, and voriconazole are also suitable antifungal active agents. Also suitable are, thiazoles including, e.g., abafungin. Suitable antifungal agents include, e.g., of amorolfin, butenafine, naftifine, and terbinafine. In addition, echinocandins, including anidulafungin, caspofungin, and micafungin, are suitable antifungals. Also suitable are griseofulvin, benzoic acid, ciclopirox, haloprogin, polygodial, tolnaftate, undecylenic acid, and Crystal violet.

Suitable antifungal agents for use in the present topical pharmaceutical compositions include, but are not limited to, natifine, butenafine, terbinafine, and amorolfine, as well as any pharmaceutically acceptable salts thereof. Suitable salts of antifungal agents include but are not limited to hydrochloride salts. In some embodiments, certain antifungal agents or pharmaceutically acceptable salts thereof are believed to act by interfering with squalene 2,3-epoxidase, which results in decreased amounts of the principal membrane sterols, especially ergosterol.

Naftifine and pharmaceutically acceptable salts thereof have fungicidal activity against organisms, including but not limited to, dermatophytes, including for example, *Trichophyton rubrum, Trichophyton interdigitale, Trichophyton verrucosum, Trichophyton mentagrophytes, Trichophyton megninii, Trichophyton tonsurans, Trichophyton schoenleinii, Trichophyton soudanense, Trichophyton violaceum, Epidermophyton floccosum, Microsporum audouini, Microsporum canis, Microsporum distortum, Microsporum gypseum*; nondermatophyte molds including, for example, *Scopulariopsis brevicaulis, Fusarium* spp., *Aspergillus* spp., *Alternaria, Acremonium, Scytalidinum dimidiatum*, and *Scytalidinium hyalinum*; and *Candida* spp. including, for example, *Candida albicans*, and *Candida parapsilosis*.

Butenafine and pharmaceutically acceptable salts thereof, for example, butenafine hydrochloride, have fungicidal activity against organisms, including but not limited to, dermatophytes, including for example, *Trichophyton rubrum, Trichophyton mentagrophytes, Trichophyton tonsurans, Epidermophyton floccosum, Microsporum canis*; nondermatophyte molds including, for example, *Aspergillus* spp.; *Candida* spp. including, for example, *Candida albicans* and *Candida parapsilosis; Malassezia furfur*; and *Cryptococcus*.

Terbinafine and pharmaceutically acceptable salts thereof, for example, terbinafine hydrochloride, is active against many fungi, including dermatophytes (*Trichophyton, Microsporum, Epidermophyton*), filamentous (e.g. *Aspergillus*), dimorphic (e.g., *Blastomyces*), and dematiaceous fungi and yeasts. Terbinifine has an antifungal spectrum of activity similar to that of naftifine. More specifically, Terbinafine and pharmaceutically acceptable salts thereof, for example, butenafine hydrochloride, have fungicidal activity against organisms, including but not limited to, dermatophytes, including for example, *Trichophyton rubrum, Trichophyton mentagrophytes, Trichophyton tonsurans, Trichophyton violaceum, Epidermophyton floccosum, Microsporum audouini, Microsporum canis*; nondermatophyte molds including, for example, *Aspergillus* spp. and *Scopulariopsis brevicaulis; Candida* spp. including, for example, *Candida albicans* and *Candida parapsilosis; Blastomyces*; and *Histoplasma.*

Amorolfine and pharmaceutically acceptable salts thereof, for example, amorolfine hydrochloride, is active against many fungi, including dermatophytes (*Trichophyton, Microsporum, Epidermophyton*), filamentous (e.g. *Aspergillus*), dimorphic (e.g., *Blastomyces* and *Sporothrix schenckii*), dematiaceous fungi and yeasts, and *Sporothrix schenckii*. Amorolfine and pharmaceutically acceptable salts thereof, for example, amorolfin hydrochloride, have fungicidal activity against organisms, including but not limited to, dermatophytes including, for example, *Trichophyton rubrum, Trichophyton mentagrophytes, Epidermophyton floccosum*; nondermatophyte molds including, for example, *Scopulariopsis* spp. including *Scopulariopsis brevicaulis, Fusarium* spp. including *Fusarium solani, Aspergillus* spp. including *Aspergillus flavus*, and *Acremonium* spp.; *Candida* spp. including, for example, *Candida albicans* and *Candida parapsilosis*; and *Malassezia* spp. including *Malassezia furfur.*

In some embodiments, an antifungal agent is selected from the group consisting of naftifine, butenafine, terbinafine, and amorolfine. In some embodiments, the antifungal agent is butenafine. In some embodiments, the antifungal agent is terbinafine. In some embodiments, the antifungal agent is amorolfine.

Methods for making the presently described antifungal agents and pharmaceutically acceptable salts thereof are disclosed in U.S. Pat. Nos. 4,755,534; 4,680,291; and 4,282,251, each of which is incorporated by reference herein in its entirety.

Antiparasitics

In some embodiments, the active agent or pharmaceutically acceptable salt thereof is an anti-parasitic agent. For example, in some embodiments, the anti-parasitic agent is permethrin, ivermectin, pyrethrins, lindane, malathion, benzyl benzoate, thiabendazole or diiodohydroxyquinoline (iodoquinol).

Immune Enhancing Agents

Additionally, the active agent or pharmaceutically acceptable salt thereof is an immune enhancing agent. For example, the immune enhancing agent may be imiquimod or interferon. In some embodiments, the active agent or pharmaceutically acceptable salt thereof is an anti-tumor/oncology or chemotherapeutic agents. For example, the anti-tumor agent may bemechlorethamine (chlormethine) or other similar alkylating agents, cisplatin, carboplatin, oxaliplatin, cyclophosphamide, chlorambucil, ifosfamide, vinca alkaloids and taxanes such as vincristine, vinblastine, vinorelbine, vindesine. bexarotene, etoposide and teniposide, and topoisomerase inhibitors including type I topoisomerase inhibitors such as camptothecins: irinotecan and topotecan or type II inhibitors including amsacrine, etoposide, etoposide phosphate, and teniposide.

Cytodestructive Agents

In some embodiments, an active agent, or pharmaceutically acceptable salt thereof is a cytodestructive agent. Examples of cytodestructive agents include, e.g., bleomycin, podophyllin/podofilox, trichloroacetic acid, canthadrin, salicylic acid, 5-fluorouracil and ingenol mebutate.

Hormonal Agents

In some embodiments, an active agent, or pharmaceutically acceptable salt thereof is a hormonal agent, including, e.g., spironolactone, aldactone and finasteride.

In some embodiments, an active agent or pharmaceutically acceptable salt thereof is a sex hormone including, e.g., estogens, estriol, estradiol, estrone, testosterone, methyltestosterone, progesterone, medroxyprogesterone, hydroxyprogesterone, norethindrone and megesterol.

Calcineurin Inhibitors

In some embodiments, an active agent, or pharmaceutically acceptable salt thereof is a calcineurin inhibitor, for example, tacrolimus and pimecrolimus.

Steroid Agents

In some embodiments, an active agent, or pharmaceutically acceptable salt thereof is a steroid agent. In some embodiments, the steroid agent is a hydrocortisone type steroid, including, e.g., hydrocortisone, hydrocortisone acetate, hydrocortisone butyrate, cortisone acetate, tixocortol pivalate, prednisolone, methylprednisolone, or prednisone. In some embodiments, the steroid agent is an acetonide or related substances including, e.g., triamcinolone acetonide, triamcinolone alcohol, mometasone, amcinonide, budesonide, desonide, fluocinonide, fluocinolone acetonide, or halcinonide. In some embodiments, the steroid agent is a betamethasone type steroid agent, including, e.g. betamethasone, betamethasone sodium phosphate, dexamethasone, dexamethasone sodium phosphate, or fluocortolone. In some embodiments, the steroid agent is an a halogenated (less labile) steroid, including, e.g., hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, or fluprednidene acetate. In some embodiments, the steroid agent is a labile prodrug ester, including, e.g., hydrocortisone-17-butyrate, 17-aceponate, 17-buteprate, and Prednicarbate. Additional steroids according to the present subject matter include, e.g., flunisolide, fluticasone, fluticasone propionate, amcinonide, clocortolone pivalate, halobetasol, desoximetasone and beclomethasone dipropionate and fludroxycortide (also known as flurandrenolone or flurandrenolide).

Retinoid Agent

In some embodiments, an active agent or pharmaceutically acceptable salt thereof is a retinoid agent, including, e.g., retinol, retinal, tretinoin (retinoic acid, Retin-A), isotretinoin, alitretinoin, etretinate and its metabolite acitretin, tazarotene, bexarotene and adapalene.

Vitamin Analogs

In some embodiments, an active agent or pharmaceutically acceptable salt thereof is a vitamin analog, including e.g., a vitamin D3 synthetic analog, calcipotriene, the naturally occurring form calcitriol.

Non-Steroidal Anti-Inflammatory Agents

In some embodiments, an active agent or pharmaceutically acceptable salt thereofis a non-steroidal anti-inflammatory (NSAID) drug. Examples of NSAIDS include, e.g., aspirin, salsalate, ibuprofen, naproxen, acid derivatives, COX-2 inhibitors, and LOX/COX inhibitors. Examples of acid derivatives include, e.g., diclofenac, piroxicam and mefenamic acid. Examples of COX-2 inhibitors include, e.g., celecoxib and rofecoxib. An example of a LOX/COX inhibitor is licofelone.

In some embodiments, an active agent or pharmaceutically acceptable salt thereof is a non-steroidal anti-inflammatory agent including, e.g., fenoprofen, ibuprofen, flurbiprofen, ketoprofen, naproxen, oxaprozin, diclofenac, etodalac, indomethacin, ketorolac, nabumetone, sulindac, tolmentin, meclofenamate, flufenamic acid, mefenamic acid, meclofenamic acid, piroxicam, salicylates, diflunisal, indomethacin, phenylbutazone, oxyphenbutazone, sulfinpyrazone, allopurinol, penicillamin, colchicine and probenicid.

Topical Contact Allergen

In some embodiments, an active agent or pharmaceutically acceptable salt thereof is a topical contact allergen including, e.g., squaric acid dibutyl ester (SADBE), diphenylcyclopropenone (DPC) or dinitrochlorobenzene (DNCB).

Skin Cosmetic Active Agent

In some embodiments, an active agent or pharmaceutically acceptable salt thereof is a skin cosmetic active agent. Non-limiting examples of skin cosmetic active agents include, e.g., hydroquinone, arbutin, deoxyarbutin, dihydroxyacetone (DHA), oxymetazolin, brimonidine, epinephrine, plant extracts, aloe, caffeine, cocoa, tea extract, primrose oil, vitamins, vitamin analogs, eflornithine hydrochloride, alpha hydroxy acids (AHA), ammonium lactate, glycolic acids, coal tar, sinecatechins, surfactants and cleansers. Plant extracts include, e.g., arnica and *allium* extract.

In some embodiments, an active agent or pharmaceutically acceptable salt thereof is a sunscreen. Examples of sunscreens include, e.g., zinc oxide, avobenzone, octinoxate, oxybenzone, titanium dioxide, trolamine salicylate and ensulzole.

In some embodiments, an active agent or pharmaceutically acceptable salt thereof is a keratolytic agent, including, e.g., urea, salicyclic acid, sulfur, and tar/coal tar.

In some embodiments, an active agent or pharmaceutically acceptable salt thereof is a vitamin. Examples of vitamins include, e.g., vitamin A, vitamin D, vitamin E, vitamin B1, vitamin B2, vitamin B3, vitamin B6, vitamin B12, vitamin C, multivitamin preparations and vitamin combinations.

Nasal Decongestants

In some embodiments, an active agent or pharmaceutically acceptable salt thereof is a nasal decongestant including, e.g., phenylpropanolamine, pseudoephedrine, phenylephrine, ephedrine, naphazoline, oxymetazoline, tetrahydrozoline, xylometazoline amd propylhexedrine.

Miscellaneous

In some embodiments, an active agent or pharmaceutically acceptable salt thereof is a miscellaneous agent including, e.g., finasteride, lamsoprazole, papaverine and prostaglandins.

Antirheumatic Agents

In some embodiments, an active agent or pharmaceutically acceptable salt thereof is an antirheumatic agent including, e.g., gold compounds, penicillamine, azathioprine and methotrexate.

Gout Agents

In some embodiments, an active agent or pharmaceutically acceptable salt thereof is an agent for gout including, e.g., probenecid, sulfinpyrazone, allopurinol and colchicine.

Pain Management Agents

In some embodiments, an active agent or pharmaceutically acceptable salt thereof is a pain management agent including, e.g., a nonopiod analgesic (acetaminophen, aspirin, choline magnesium trisalicylate, NSAIDs, tramadol (opioid & nonopioid)), an opioid analgesic (codeine, dihydrocodeine, hydrocodone, oxycodone, morphine, hydromorphone, fentanyl), or an analgesic adjuvant used to enhance the effect of an analgesic or counteract side effects of such (tricyclic antidepressants, benzodiazepines, caffeine, corticosteroids, anticonvulsants).

In some embodiments, an active agent or pharmaceutically acceptable salt thereof is an analgesic agent including, e.g., codeine, hydrocodone, hydromorphone, morphine, oxymorphone, oxycodone, meperidine, methadone, propoxyphene, tramadol, acetaminophen, pentazocine and fentanyl salicylates.

Antimycobacterial Agents

In some embodiments, an active agent or pharmaceutically acceptable salt thereof is an antimycobacterial including, e.g., isoniazide, rifamycin (rifabutin, rifampin, rifapentine), pyrazinamide, ethambutol, fluoroquinolones (moxifloxacin, levofloxacin, ciprofloxacin), aminoglycosides (streptomycin, amikacin, amikamycin, kanamycin), azithromycin, clarithromycin, capreomycin, rifampicin, nalidixic acid, ciprofloxacin, ofloxacin, p-aminosalicyclic acid, isoniazid, ethionamide, cycloserine, clofazimine, macrolides (clarithromycin, azithromycin), doxycycline, tigecycline, trimethoprim-sulfamethoxazole, amikacin, tobramycin, imipenem, linezolid, and cefoxitin.

Sulfonamide Agents

In some embodiments, an active agent or pharmaceutically acceptable salt thereof is a sulfonamide including, e.g., sulfadiazine, sulfacytine, sulfamethoxazole and suflamethiazole.

Antituberculosis Agents

In some embodiments, an active agent or pharmaceutically acceptable salt thereof is an antituberculous drug including isoniazid, rifampin, rifabutin, ethambutol HCl, pyrazinamide, aminosalicylate, sodium ethionamide, cycloserine, streptomycin sulfate, capreomycin.

Amebicide Agents

In some embodiments, an active agent or pharmaceutically acceptable salt thereof is an amebicide including, e.g., paromomycin, iodoquinol, metronidazole, emetine and chloroquine.

Antiviral Agents

In some embodiments, an active agent or pharmaceutically acceptable salt thereof is an antiviral including, e.g., acyclovir, pencyclovir, cidofovir, idoxuridine, stavudine, zidovudine, ribavarin, amantadine, foscarnet, didanosine, acyclovir, ganciclovir, cidofovir, zalcitabine, rimantadine, calacyclovir, famiciclovir, abacavir, didanosine, emtricitabine, lamivudine, stavudine, tenofovir, zalcitabine, zidovudine, zidovudine-lamivudine, TRIZIVIR (zidovudine, lamivudine, abacavir), EPZICOM (aba-cavir-lamivudine), TRUVADA (tenofovir-emtricitabine), efavirenz, nevirapine, and delavirdine, amprenavir, atazanavir, fosamprenavir, indinavir, lopinavir-ritonavir, nelfinavir, ritonavir, saquinavir, and tipranavir Anti-Influenza In some embodiments, an active agent or pharmaceutically acceptable salt thereof is an anti-influenza agent including, e.g., rimatadine, amantadine, oseltamivir, and zanamivir.

Anti-Infective Agents

In some embodiments, an active agent or pharmaceutically acceptable salt thereof is a miscellaneous anti-infective including, e.g., trimethoprim, trimethoprim-sulfamethoxazole, erythromycin-sulfisoxazole, furazolidone, pentamidine, eflornithine, atovaquone, trimetrexate and glucuronate.

In some embodiments, an active agent or pharmaceutically acceptable salt thereof is aleprostatics including dapsone and clofazime.

Antihelmintic Agents

In some embodiments, an active agent or pharmaceutically acceptable salt thereof is an antihelmintic agent including, e.g., mebendazole, diethylcarbamazine citrate, pyrantel, thiabendazole, piperazine, quinacrine, niclosamide, oxamniquine and praziquantel.

Antihistamine Agents

In some embodiments, an active agent or pharmaceutically acceptable salt thereof is an antihistamine including, e.g., diphenhydramine, chlorpheniramine, pyrilamine, doxepin, carbinoxamine, clemastine, tripelennamine, brompheniramine, dexchlorpheniranune, triprolidine, methdilazine, promethazine, trimeprazine, hydroxyzine HCl, azatadine, cyproheptadine, phenindamine, astemizole, loratadine, terfenadine and cetirizine.

Antimetabolite Agent

In some embodiments, an active agent or pharmaceutically acceptable salt thereof is an antimetabolite agent including, e.g., 5-fluorouracil, 6-mercaptopurine, mycophenolic acid, methotrexate, cytarabine, floxuridineand thioguanine Anticholinergic Agent In some embodiments, an active agent or pharmaceutically acceptable salt thereof is an anticholinergic agent including e.g., atropine, bornaprine, glycopyrrolate, scopolamine, homatropine, tropatepine, tropicamide, pirenzepine, isopropamide, propantheline, methscopolamine, methantheline, trihexyphenidyl, benztropine and biperiden.

Steroidal Anti-Inflammatory Agents

In some embodiments, an active agent or pharmaceutically acceptable salt thereof is a steroidal anti-inflammatory agent including e.g., cortisone, hydrocortisone, hydrocortisone acetate, prednisone, prednisolone, triamcinolone, methylprednisolone, dexamethasone, betamethasone, clobetasol, diflorasone, halobetasol, amicinonide, desoximetasone, fluocinolone, halcinonide, clocortolone, flurandrenolide, fluticasone, mometasone, aclometasone, desonide, and fludrocortisone. In some embodiments, the active agent is fluticasone.

Local Anesthetic Agents

In some embodiments, an active agent or pharmaceutically acceptable salt thereof is alocal anesthetic including e.g., dibucaine, lidocaine, benzocaine, butamben, picrate, tetracaine, dyclonine, pramoxine and prilocalne.

Sunscreen Agents

In some embodiments, an active agent or pharmaceutically acceptable salt thereof is a sunscreen agent including, e.g., oxybenzone, dioxybenzone, p-aminobenzoic acid, ethyl dihydroxy propyl PABA, padimate 0, glyceryl PABA, cinoxate, ethylhexyl p-methoxycinnamate, octocrylene, octyl methoxycinnamate, ethylhexyl salicylate, homosalate, octyl salicylate, menthyl anthranilate, digalloyl trioleate and avobenzone.

Muscle Relaxants

In some embodiments, an active agent or pharmaceutically acceptable salt thereof is a muscle relaxant including, e.g., carisoprodol, chlorphenesin, chlorzoxazone, cyclobenzaprine, metaxalone, methocarbamol, orphenadrine, diazepam and baclofen.

Exemplary Gel Compositions Containing an Active Agent

In some embodiments, the present invention provides a gel composition comprising any of the above-described active agents in any of the above described amounts. In some embodiments, the active agent is an antifungal agent as described above. In certain embodiments, the antifungal agent is naftifine (e.g., naftifine hydrochloride). In some embodiments, the active agent is a steroid as described above. In certain embodiments, the active agent is a corticosteroid such as fluticasone (e.g., fluticasone propionate).

In some embodiments, the present invention provides a gel composition comprising or consisting essentially of:
  (i) an active agent;
  (ii) a first solvent;
  (iii) optionally a second solvent;
  (iv) a non-carbomer rheology modifier; and
optionally one or more of: a solubilizing agent, a diluent, a preservative, a pH adjuster, a chelating agent, a coloring agent, and a fragrance. Exemplary such active agents, solvents, non-carbomer rheology modifiers, solubilizing agents, diluents, preservatives, pH adjusters, and chelating agents, are described above and herein. Exemplary such gel compositions are described in further detail below and herein.

In some embodiments, the present invention provides a gel composition, comprising or consisting essentially of from about 0.01 wt % to about 6.0 wt % of an active agent or a pharmaceutically acceptable salt thereof, from about 10 wt % to about 25 wt % of a first solvent, from about 10 wt % to about 25 wt % of a second solvent, from about 0.75 wt % to about 2.25 wt % of a non-carbomer rheology modifier, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 6.0 wt % of an active agent or a pharmaceutically acceptable salt thereof, from about 15 wt % to about 25 wt % of a first solvent, from about 15 wt % to about 25 wt % of a second solvent, from about 0.75 wt % to about 2.25 wt % of a non-carbomer rheology modifier, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of an active agent or a pharmaceutically acceptable salt thereof, from about 15 wt % to about 25 wt % of a first solvent, from about 15 wt % to about 25 wt % of a second solvent, from about 0.75 wt % to about 2.25 wt % of a non-carbomer rheology modifier, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % an active agent or a pharmaceutically acceptable salt thereof, from about 15 wt % to about 25 wt % of a glycol solvent, from about 15 wt % to about 25 wt % of an alcohol solvent; from about 0.75 wt % to about 2.25 wt % of a hydroxy cellulose, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of an active agent or a pharmaceutically acceptable salt thereof, from about 15 wt % to about 25 wt % of a glycol solvent, from about 15 wt % to about 25 wt % of an alcohol solvent, from about 0.75 wt % to about 2.25 wt % of a hydroxy cellulose, from about 3 wt % to about 8 wt % of a solubilizing agent, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of an active agent or a pharmaceutically acceptable salt thereof, from about 15 wt % to about 25 wt % propylene glycol, from about 15 wt % to about 25 wt % ethanol, from about 0.75 wt % to about 2.25 wt % hydroxyethyl cellulose, from about 3 wt % to about 8 wt % Polysorbate 20, and optionally one or more of: a solubilizing agent, a diluent, a pH adjuster, a chelating agent, a preservative, a fragrance, and a coloring agent. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof, in an amount of from about 0.01 wt % to about 4.0 wt %, propylene glycol in an amount of from about 18 wt % to about 22 wt %, ethanol in an amount of from about 17 wt % to about 21 wt %, hydroxyethyl cellulose in an amount of from about 1.5 wt % to about 2 wt %, Polysorbate 20 in an amount of from about 4 wt % to about 6 wt %, and optionally one or more of: a solubilizing agent, a diluent, a pH adjuster, a chelating agent, a preservative, a fragrance, and a coloring agent. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof, in an amount of from about 0.01 wt % to about 4.0 wt %, propylene glycol in an amount of from about 18 wt % to about 22 wt %, ethanol in an amount of from about 17 wt % to about 21 wt %, hydroxyethyl cellulose in an amount of from about 1.5 wt % to about 2 wt %, Polysorbate 20 in an amount of from about 4 wt % to about 6 wt %, water, and optionally one or more of: a solubilizing agent, a pH adjuster, a chelating agent, a preservative, a fragrance, and a coloring agent. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof, in an amount of from about 0.01 wt % to about 4.0 wt %, propylene glycol in an amount of from about 19 wt % to about 21 wt %, ethanol in an amount of from about 18 wt % to about 20 wt %, hydroxyethyl cellulose in an amount of from about 1.6 wt % to about 1.9 wt %, and optionally one or more of: a solubilizing agent, a diluent, a pH adjuster, a chelating agent, a preservative, a fragrance, and a coloring agent.

In some embodiments, the present invention provides a gel composition, comprising or consisting essentially of an active agent or pharmaceutically acceptable salt thereof, in an amount of from about 0.01 wt % to about 4.0 wt %, propylene glycol in an amount of from about 19 wt % to about 21 wt %, ethanol in an amount of from about 18 wt % to about 20 wt %, hydroxyethyl cellulose in an amount of from about 1.6 wt % to about 1.9 wt %, Polysorbate 20 in an amount of from about 4.5 wt % to about 5.5 wt %, water, and optionally one or more of: a pH adjuster, a chelating agent, a preservative, a fragrance, and a coloring agent. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof, in an amount of from about 0.01 wt % to about 4.0 wt %, propylene glycol in an amount of from about 19.5 wt % to about 20.5 wt %, ethanol in an amount of from about 18.5 wt % to about 19.5 wt %, hydroxyethyl cellulose in an amount of from about 1.7 wt % to about 1.8 wt %, Polysorbate 20 in an amount of from about 4.75 wt % to about 5.25 wt %, and optionally one or more of: a diluent, a pH adjuster, a chelating agent, a preservative, a fragrance, and a coloring agent. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof, in an amount of from about 0.01 wt % to about 4.0 wt %, propylene glycol in an amount of from about 19.5 wt % to about 20.5 wt %, ethanol in an amount of from about 18.5 wt % to about 19.5 wt %, hydroxyethyl cellulose in an amount of from about 1.7 wt % to about 1.8 wt %, Polysorbate 20 in an amount of from about 4.75 wt % to about 5.25 wt %, water, and optionally one or more of: a pH adjuster, a chelating agent, a preservative, a fragrance, and a coloring agent. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof in an amount of from about 0.01 wt % to about 4.0 wt %, about 20 wt % propylene glycol, about 19 wt % ethanol, about 1.75 wt % hydroxyethyl cellulose, about 5 wt % Polysorbate 20, water, and optionally one or more of: a pH adjuster, a chelating agent, a preservative, a fragrance, and a coloring agent. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof in an amount of from about 0.01 wt % to about 4.0 wt %, about 20 wt % propylene glycol, about 19 wt % ethanol, about 1.75 wt % hydroxyethyl cellulose, about 5 wt % Polysorbate 20, water, trolamine, ethylenediaminetetracetic acid (EDTA) or a salt thereof, benzyl alcohol, and optionally one or more of: a fragrance, and a coloring agent. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof in an amount of from about 0.01 wt % to about 4.0 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, water, and optionally one or more members selected from the group consisting of a fragrance and a coloring agent. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof in an amount of from about 0.01 wt % to about 4.0 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof in an amount of from about 1.0 wt % to about 3.0 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water. In certain embodiments, a provided gel composition is as described above, with the exception that Polysorbate 20 is replaced with Polysorbate 80.

In some embodiments, the present invention provides a gel composition, comprising or consisting essentially of an active agent or pharmaceutically acceptable salt thereof in an amount of about 2.0 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water. In certain embodiments, a provided gel composition is as described above, with the exception that Polysorbate 20 is replaced with Polysorbate 80.

In some embodiments, the present invention provides a gel composition, comprising or consisting essentially of from about 0.01 wt % to about 3.0 wt % of an active agent or a pharmaceutically acceptable salt thereof, from about 10 wt % to about 25 wt % of a first solvent, from about 10 wt % to about 25 wt % of a second solvent, from about 0.75 wt % to about 2.25 wt % of a non-carbomer rheology modifier, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 3.0 wt % of an active agent or a pharmaceutically acceptable salt thereof, from about 15 wt % to about 25 wt % of a first solvent, from about 15 wt % to about 25 wt % of a second solvent, from about 0.75 wt % to about 2.25 wt % of a non-carbomer rheology modifier, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of an active agent or a pharmaceutically acceptable salt thereof, from about 15 wt % to about 25 wt % of a first solvent, from about 15 wt % to about 25 wt % of a second solvent, from about 0.75 wt % to about 2.25 wt % of a non-carbomer rheology modifier, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % an active agent or a pharmaceutically acceptable salt thereof, from about 15 wt % to about 25 wt % of a glycol, from about 15 wt % to about 25 wt % of an alcohol solvent; from about 0.75 wt % to about 2.25 wt % of a hydroxy cellulose, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of an active agent or a pharmaceutically acceptable salt thereof, from about 15 wt % to about 25 wt % of a glycol solvent, from about 15 wt % to about 25 wt % of an alcohol solvent, from about 0.75 wt % to about 2.25 wt % of a hydroxy cellulose, from about 3 wt % to about 8 wt % of a solubilizing agent, and optionally one or more of: a solubilizing agent, a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of an active agent or a pharmaceutically acceptable salt thereof, from about 15 wt % to about 25 wt % propylene glycol, from about 15 wt % to about 25 wt % ethanol, from about 0.75 wt % to about 2.25 wt % hydroxyethyl cellulose, from about 3 wt % to about 8 wt % Polysorbate 20, and optionally one or more of: a solubilizing agent, a diluent, a pH adjuster, a chelating agent, a preservative, a fragrance, and a coloring agent.

In some embodiments, the present invention provides a gel composition, comprising or consisting essentially of an active agent or pharmaceutically acceptable salt thereof, in an amount of from about 0.01 wt % to about 2.0 wt %, propylene glycol in an amount of from about 18 wt % to about 22 wt %, ethanol in an amount of from about 17 wt % to about 21 wt %, hydroxyethyl cellulose in an amount of from about 1.5 wt % to about 2 wt %, Polysorbate 20 in an amount of from about 4 wt % to about 6 wt %, and optionally one or more of: a solubilizing agent, a diluent, a pH adjuster, a chelating agent, a preservative, a fragrance, and a coloring agent.

In some embodiments, the present invention provides a gel composition, comprising or consisting essentially of an active agent or pharmaceutically acceptable salt thereof, in an amount of from about 0.01 wt % to about 2.0 wt %, propylene glycol in an amount of from about 18 wt % to about 22 wt %, ethanol in an amount of from about 17 wt % to about 21 wt %, hydroxyethyl cellulose in an amount of from about 1.5 wt % to about 2 wt %, Polysorbate 20 in an amount of from about 4 wt % to about 6 wt %, water, and optionally one or more of: a solubilizing agent, a pH adjuster, a chelating agent, a preservative, a fragrance, and a coloring agent.

In some embodiments, the present invention provides a gel composition, comprising or consisting essentially of an active agent or pharmaceutically acceptable salt thereof, in an amount of from about 0.01 wt % to about 2.0 wt %, propylene glycol in an amount of from about 19 wt % to about 21 wt %, ethanol in an amount of from about 18 wt % to about 20 wt %, hydroxyethyl cellulose in an amount of from about 1.6 wt % to about 1.9 wt %, and optionally one or more of: a solubilizing agent, a diluent, a pH adjuster, a chelating agent, a preservative, a fragrance, and a coloring agent.

In some embodiments, the present invention provides a gel composition, comprising or consisting essentially of an active agent or pharmaceutically acceptable salt thereof, in an amount of from about 0.01 wt % to about 2.0 wt %, propylene glycol in an amount of from about 19 wt % to about 21 wt %, ethanol in an amount of from about 18 wt % to about 20 wt %, hydroxyethyl cellulose in an amount of from about 1.6 wt % to about 1.9 wt %, Polysorbate 20 in an amount of from about 4.5 wt % to about 5.5 wt %, water, and optionally one or more of: a pH adjuster, a chelating agent, a preservative, a fragrance, and a coloring agent.

In some embodiments, the present invention provides a gel composition, comprising or consisting essentially of an active agent or pharmaceutically acceptable salt thereof, in an amount of from about 0.01 wt % to about 2.0 wt %, propylene glycol in an amount of from about 19.5 wt % to about 20.5 wt %, ethanol in an amount of from about 18.5 wt % to about 19.5 wt %, hydroxyethyl cellulose in an amount of from about 1.7 wt % to about 1.8 wt %, Polysorbate 20 in an amount of from about 4.75 wt % to about 5.25 wt %, and optionally one or more of: a diluent, a pH adjuster, a chelating agent, a preservative, a fragrance, and a coloring agent.

In some embodiments, the present invention provides a gel composition, comprising or consisting essentially of an active agent or pharmaceutically acceptable salt thereof, in an amount of from about 0.01 wt % to about 2.0 wt %, propylene glycol in an amount of from about 19.5 wt % to about 20.5 wt %, ethanol in an amount of from about 18.5 wt % to about 19.5 wt %, hydroxyethyl cellulose in an amount of from about 1.7 wt % to about 1.8 wt %, Polysorbate 20 in an amount of from about 4.75 wt % to about 5.25 wt %, water, and optionally one or more of: a pH adjuster, a chelating agent, a preservative, a fragrance, and a coloring agent.

In some embodiments, the present invention provides a gel composition, comprising or consisting essentially of an active agent or pharmaceutically acceptable salt thereof in an amount of from about 0.01 wt % to about 2.0 wt %, 20 wt % propylene glycol, 19 wt % ethanol, 1.75 wt % hydroxyethyl cellulose, 5 wt % Polysorbate 20, water, and optionally one or more of: a pH adjuster, a chelating agent, a preservative, a fragrance, and a coloring agent.

In some embodiments, the present invention provides a gel composition, comprising or consisting essentially of an active agent or pharmaceutically acceptable salt thereof in an amount of from about 0.01 wt % to about 2.0 wt %, about 20 wt % propylene glycol, about 19 wt % ethanol, about 1.75 wt % hydroxyethyl cellulose, about 5 wt % Polysorbate 20, water, trolamine, ethylenediaminetetracetic acid (EDTA) or a salt thereof, benzyl alcohol, and optionally one or more of: a fragrance, and a coloring agent.

In some embodiments, the present invention provides a gel composition, comprising or consisting essentially of an active agent or pharmaceutically acceptable salt thereof in an amount of from about 0.01 wt % to about 2.0 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, water, and optionally one or more members selected from the group consisting of a fragrance and a coloring agent.

In some embodiments, the present invention provides a gel composition, comprising or consisting essentially of an active agent or pharmaceutically acceptable salt thereof in an amount of from about 0.01 wt % to about 1.5 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water.

In some embodiments, the present invention provides a gel composition, comprising or consisting essentially of an active agent or pharmaceutically acceptable salt thereof in an amount of from about 0.01 wt % to about 1.0 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water.

In some embodiments, the present invention provides a gel composition, comprising or consisting essentially of an active agent or pharmaceutically acceptable salt thereof in an amount of from about 0.01 wt % to about 0.05 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water.

In some embodiments, the present invention provides a gel composition, comprising or consisting essentially of an active agent or pharmaceutically acceptable salt thereof in an amount of from about 0.02 wt % to about 0.04 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water.

In some embodiments, the present invention provides a gel composition, comprising or consisting essentially of an active agent or pharmaceutically acceptable salt thereof in an amount of from about 0.02 wt % to about 0.03 wt %, about 20 wt % propylene glycol, about 19 wt % ethanol, about 5 wt % Polysorbate 20, about 1.75 wt % hydroxyethyl cellulose, 0.17 wt % trolamine, about 0.02 wt % ethylenediaminetetracetic acid (EDTA) or a salt thereof, about 1 wt % benzyl alcohol, and water.

In some embodiments, the present invention provides a gel composition, comprising or consisting essentially of an active agent or pharmaceutically acceptable salt thereof in an amount of about 0.025 wt %, 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water.

In some embodiments, the present invention provides a gel composition, comprising or consisting essentially of an active agent or pharmaceutically acceptable salt thereof in an amount of from about 0.03 wt % to about 0.07 wt %, about 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water.

In some embodiments, the present invention provides a gel composition, comprising or consisting essentially of an active agent or pharmaceutically acceptable salt thereof in an amount of from about 0.04 wt % to about 0.06 wt %, about 20 wt % propylene glycol, about 19 wt % ethanol, about 5 wt % Polysorbate 20, about 1.75 wt % hydroxyethyl cellulose, 0.17 wt % trolamine, about 0.02 wt % ethylenediaminetetracetic acid (EDTA) or a salt thereof, about 1 wt % benzyl alcohol, and water.

In some embodiments, the present invention provides a gel composition, comprising or consisting essentially of an active agent or pharmaceutically acceptable salt thereof in an amount of about 0.05 wt %, 20 wt % propylene glycol, about 19 wt % ethanol, about 5 wt % Polysorbate 20, about 1.75 wt % hydroxyethyl cellulose, about 0.17 wt % trolamine, about 0.02 wt % ethylenediaminetetracetic acid (EDTA) or a salt thereof, about 1 wt % benzyl alcohol, and water.

Gel Compositions Comprising an Antifungal Agent

In some embodiments, the present invention provides a gel composition comprising or consisting essentially of:

(i) an active agent selected from an antifungal agent;

(ii) a first solvent selected from a glycol solvent;

(iii) a second solvent selected from an alkyl alcohol solvent;

(iv) a non-carbomer rheology modifier selected from a hydroxyl cellulose;

(v) a solubolzing agent selected from a polysorbate solubilizing agent; and optionally one or more of: an additional solubilizing agent, a diluent, a preservative, a pH adjuster, a chelating agent, a coloring agent, and a fragrance.

In some embodiments, the present invention provides a gel composition wherein the active agent is naftifine or a salt thereof. In some embodiments, the present invention provides a gel composition wherein the active agent is naftifine hydrochloride.

In some embodiments, the present invention provides a gel pharmaceutical composition, comprising or consisting essentially of naftifine or pharmaceutically acceptable salt thereof, in an amount of from about 0.5 wt % to about 4.0 wt %, propylene glycol in an amount of about 20 wt %, ethanol in an amount of about 19 wt %, hydroxyethyl cellulose in an amount of about 1.75 wt %, Polysorbate 20 in an amount of about 5 wt %, water, and optionally one or more of: a pH adjuster, a chelating agent, a preservative, a fragrance, and a coloring agent. In certain embodiments, the gel composition is as described above, with the exception that Polysorbate 20 is replaced with Polysorbate 80.

In some embodiments, the present invention provides a gel composition, comprising or consisting essentially of naftifine or pharmaceutically acceptable salt thereof, in an amount of from about 1.0 wt % to about 3.0 wt %, about 20 wt % propylene glycol, about 19 wt % ethanol, about 1.75 wt % hydroxyethyl cellulose, about 5 wt % Polysorbate 20, water, trolamine, ethylenediaminetetracetic acid (EDTA) or a salt thereof, benzyl alcohol, and optionally one or more of: a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of naftifine or pharmaceutically acceptable salt thereof, in an amount of from about 1.0 wt % to about 3.0 wt %, about 20 wt % propylene glycol, about 19 wt % ethanol, about 1.75 wt % hydroxyethyl cellulose, about 5 wt % Polysorbate 20, water, about 0.17 wt % trolamine, about 0.02 wt % ethylenediaminetetracetic acid (EDTA) or a salt thereof, about 1.0 wt % benzyl alcohol, and optionally one or more of: a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of naftifine or pharmaceutically acceptable salt thereof in an amount of about 0.1 wt %, 0.5 wt %, 1.0 wt %, 1.5 wt %, 2.0 wt %, 2.5 wt %, 3.0 wt %, 3.5 wt % or 4.0 wt %, about 20 wt % propylene glycol, about 19 wt % ethanol, about 1.75 wt % hydroxyethyl cellulose, about 5 wt % Polysorbate 20, water, about 0.17 wt % trolamine, about 0.02 wt % ethylenediaminetetracetic acid (EDTA) or a salt thereof, about 1.0 wt % benzyl alcohol, and optionally one or more of: a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of naftifine or pharmaceutically acceptable salt thereof in an amount of about 2 wt %, propylene glycol in an amount of about 20 wt %, ethanol in an amount of about 19 wt %, Polysorbate 20 in an amount of about 5 wt %, hydroxyethyl cellulose in an amount of about 1.75 wt %, and water. In certain embodiments, the gel composition is as described above, with the exception that Polysorbate 20 is replaced with Polysorbate 80.

In some embodiments, the present invention provides a gel composition, comprising or consisting essentially of naftifine or pharmaceutically acceptable salt thereof in an amount of about 2.0 wt %, about 20 wt % propylene glycol, about 19 wt % ethanol, about 1.75 wt % hydroxyethyl cellulose, about 5 wt % Polysorbate 20, water, about 0.17 wt % trolamine, about 0.02 wt % ethylenediaminetetracetic acid (EDTA) or a salt thereof, about 1.0 wt % benzyl alcohol, and optionally one or more of: a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of naftifine hydrochloride in an amount of about 2.0 wt %, about 20 wt % propylene glycol, about 19 wt % ethanol, about 1.75 wt % hydroxyethyl cellulose, about 5 wt % Polysorbate 20, water, about 0.17 wt % trolamine, about 0.02 wt % ethylenediaminetetracetic acid (EDTA) or a salt thereof, about 1.0 wt % benzyl alcohol, and optionally one or more of: a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of naftifine hydrochloride in an amount of about 2.0 wt %, about 20 wt % propylene glycol, about 19 wt % ethanol, about 1.75 wt % hydroxyethyl cellulose, about 5 wt % Polysorbate 20, water, about 0.17 wt % trolamine, about 0.02 wt % ethylenediaminetetracetic acid (EDTA) or a salt thereof, and about 1.0 wt % benzyl alcohol. In certain embodiments, the gel composition is as described above, with the exception that Polysorbate 20 is replaced with Polysorbate 80.

In some embodiments, the present invention provides a gel composition for topical administration consisting essentially of:

(i) naftifine or a pharmaceutically acceptable salt thereof, present in an amount of from about 0.5 wt % to about 4 wt %;

(ii) a first solvent which is a glycol solvent present in an amount of from about 10 wt % to about 25 wt %;

(iii) a second solvent which is an alcohol solvent present in an amount of from about 10 wt % to about 25 wt %;

(iv) a non-carbomer rheology modifier; and optionally one or more of: a solubilizing agent, water, a preservative, a pH adjuster, a chelating agent, a coloring agent, and a fragrance.

In certain embodiments, the gel composition is as described above, wherein the naftifine or a pharmaceutically acceptable salt thereof is present in an amount of from about 1.0 wt % to about 3.0 wt %. In certain embodiments, the gel composition is as described above, wherein the glycol solvent is present in an amount of about 18 wt % to about 22 wt %. In certain embodiments, the gel composition is as described above, wherein the glycol solvent is propylene glycol. In certain embodiments, the gel composition is as described above, wherein the alcohol is present in an amount of from about 17 wt % to about 22 wt %. In certain embodiments, the gel composition is as described above, wherein the alcohol is ethanol. In certain embodiments, the gel composition is as described above, wherein the non-carbomer rheology modifier is a hydroxy cellulose. In certain embodiments, the gel composition is as described above, wherein the hydroxy cellulose is present in an amount of from about 0.75 wt % to about 2.25 wt %. In certain embodiments, the gel composition is as described above, wherein the hydroxy cellulose hydroxyethyl cellulose. In certain embodiments, the gel composition is as described above, wherein at least one of the one or more solubilizing agents is a polysorbate solubilizing agent. In certain embodiments, the gel composition is as described above, wherein the polysorbate solubilizing agent is present in an amount of from about 3 wt % to about 8 wt %. In certain embodiments, the gel composition is as described above, wherein the polysorbate solubilizing agent is Polysorbate 20 or Polysorbate 80. In certain embodiments, the gel composition is as described above, wherein the naftifine or pharmaceutically acceptable salt thereof is naftifine hydrochloride. In certain embodiments, the gel composition is as described above, wherein the naftifine or a pharmaceutically acceptable salt thereof (e.g., naftifine hydrochloride) is present in an amount of about 2.0 wt %, the glycol solvent (e.g., propylene glycol) is present in an amount of about 20 wt %, the alcohol solvent (e.g., ethanol) is present in an amount of about 19 wt %, the non-carbomer rheology modifier (e.g., hydroxyethyl cellulose) is present in an amount of about 1.75 wt %, and the solubilizing agent is a polysorbate (e.g., Polysorbate 20 or Polysorbate 80) present in an amount of about 5 wt %.

In some embodiments, the present invention provides a gel composition comprising or consisting essentially of from about 0.01 wt % to about 4.0 wt % naftifine, or a pharmaceutically acceptable salt thereof, not more than 50 wt % of a first solvent, a non-carbomer rheology modifier, a first solubilizing agent, and optionally one or more of: a diluent, a preservative, a pH adjuster, a chelating agent, a coloring agent, and a fragrance.

In some embodiments, the present invention provides a gel composition comprising or consisting essentially of from about 0.01 wt % to about 4.0 wt % naftifine, or a pharmaceutically acceptable salt thereof, not more than 45 wt % of a first solvent, a non-carbomer rheology modifier, a first solubilizing agent, and optionally one or more of: a diluent, a preservative, a pH adjuster, a chelating agent, a coloring agent, and a fragrance.

In some embodiments, the present invention provides a gel composition, comprising or consisting essentially of from about 0.01 wt % to about 4.0 wt % naftifine or a pharmaceutically acceptable salt thereof, not more than 45 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % naftifine, or a pharmaceutically acceptable salt thereof, not more than 45 wt % of an alcohol solvent, from about 0.75 wt % to about 2.25 wt % of a hydroxy cellulose, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % naftifine, or a pharmaceutically acceptable salt thereof, not more than 45 wt % of an alcohol solvent, from about 0.75 wt % to about 2.25 wt % of a hydroxy cellulose, from about 3 wt % to about 8 wt % of a polysorbate solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % naftifine, or a pharmaceutically acceptable salt thereof, not more than 45 wt % of an alcohol solvent, from about 0.75 wt % to about 2.25 wt % of a hydroxy cellulose, from about 3 wt % to about 8 wt % Polysorbate 80, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % naftifine, or a pharmaceutically acceptable salt thereof, not more than 45 wt % ethanol, from about 1.25 wt % to about 1.75 wt % of hydroxy propylcellulose, from about 4 wt % to about 6 wt % Polysorbate 80, and optionally one or more of: a diluent, a pH adjuster, a chelating agent, a preservative, a fragrance, and a coloring agent.

In some embodiments, the present invention provides a gel composition, comprising or consisting essentially of from about 0.5 wt % to about 3.0 wt % naftifine, or a pharmaceutically acceptable salt thereof, not more than 45 wt % ethanol, from about 1.25 wt % to about 1.75 wt % of hydroxy propylcellulose, from about 4 wt % to about 6 wt % Polysorbate 80, and optionally one or more of: a diluent, a pH adjuster, a chelating agent, a preservative, a fragrance, and a coloring agent.

In some embodiments, the present invention provides a gel composition, comprising or consisting essentially of from about 1.0 wt % to about 3.0 wt % naftifine, or a pharmaceutically acceptable salt thereof, not more than 45 wt % ethanol, from about 1.25 wt % to about 1.75 wt % of hydroxy propylcellulose, from about 4 wt % to about 6 wt % Polysorbate 80, and optionally one or more of: a diluent, a pH adjuster, a chelating agent, a preservative, a fragrance, and a coloring agent.

In some embodiments, the present invention provides a gel composition, comprising or consisting essentially of from about 1.5 wt % to about 2.5 wt % naftifine, or a pharmaceutically acceptable salt thereof, not more than 45 wt % ethanol, from about 1.25 wt % to about 1.75 wt % of hydroxy propylcellulose, from about 4 wt % to about 6 wt % Polysorbate 80, and optionally one or more of: a diluent, a pH adjuster, a chelating agent, a preservative, a fragrance, and a coloring agent.

In some embodiments, the present invention provides a gel composition, comprising or consisting essentially of about 2.0 wt % naftifine, or a pharmaceutically acceptable salt thereof, not more than 45 wt % ethanol, about 1.5 wt % of hydroxy propylcellulose, about 5 wt % Polysorbate 80, water, diisopropanolamine, ethylenediaminetetracetic acid (EDTA) or a salt thereof, and optionally one or more of: a fragrance and a coloring agent.

In some embodiments, the present invention provides a gel composition, consisting essentially of from about 2.0 wt % naftifine, or a pharmaceutically acceptable salt thereof, about 45 wt % ethanol, about 1.5 wt % of hydroxy propylcellulose, about 5 wt % Polysorbate 80, water, about 0.13 wt % diisopropanolamine, about 0.02 wt % ethylenediaminetetracetic acid (EDTA) or a salt thereof, and optionally one or more of: a fragrance and a coloring agent.

Gel Compositions Comprising a Steroidal Anti-Inflammatory Agent

As described above and herein, in some embodiments, the present invention provides gel compositions in which the active agent is a steroid. In certain embodiments, the active agent is a corticosteroid such as fluticasone (e.g., fluticasone propionate).

Steroids/Fluticasone

As described above and herein, in some embodiments, the present invention provides gel compositions comprising or consisting essentially of:

(i) an active agent selected from a steroid;
(ii) a first solvent selected from a glycol solvent;
(iii) optionally a second solvent;
(iv) a non-carbomer rheology modifier;
(v) a first solubilizing agent selected from a polysorbate solubilizing agent;
(vi) optionally a second solubilizing agent;
(vii) optionally a third solubilizing agent; and
optionally one or more of: a diluent, a preservative, a pH adjuster, a chelating agent, a coloring agent, and a fragrance. Exemplary such active agents, solvents, non-carbomer rheology modifiers, solubilizing agents, diluents, preservatives, pH adjusters, and chelating agents, are described above and herein. Exemplary such gel compositions are described in further detail below and herein.

In some embodiments, the present invention provides a gel composition comprising or consisting essentially of at least about 0.01 wt % of a steroid or a pharmaceutically acceptable salt thereof, not more than 50 wt % of a first solvent, a non-carbomer rheology modifier, a first solubilizing agent, and optionally one or more of: a diluent, a preservative, a pH adjuster, a chelating agent, a coloring agent, and a fragrance.

In some embodiments, the present invention provides a gel composition comprising or consisting essentially of at least about 0.01 wt % of a steroid or a pharmaceutically acceptable salt thereof, not more than 45 wt % of a first solvent, a non-carbomer rheology modifier, a first solubilizing agent, and optionally one or more of: a diluent, a preservative, a pH adjuster, a chelating agent, a coloring agent, and a fragrance.

In some embodiments, the present invention provides a gel composition, comprising or consisting essentially of at least about 0.01 wt % of a steroid or a pharmaceutically acceptable salt thereof, not more than 45 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 6.0 wt % of a steroid or a pharmaceutically acceptable salt thereof, not more than 45 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, not more than 45 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, not more than 40 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, not more than 35 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, not more than 30 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, not more than 25 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, not more than 20 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, about 30 wt % to about 50 wt % of a glycol solvent, from about 0.75 wt % to about 2.25 wt % of a hydroxy cellulose, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, about 30 wt % to about 50 wt % of a glycol solvent, from about 0.75 wt % to about 2.25 wt % of a hydroxy cellulose, from about 3 wt % to about 8 wt % of a polysorbate solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, about 30 wt % to about 50 wt % of a glycol solvent, from about 0.75 wt % to about 2.25 wt % of a hydroxy cellulose, from about 3 wt % to about 8 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 1.0 wt % of a steroid or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.05 wt % of a steroid or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of about 0.025 wt % of a steroid or a pharmaceutically acceptable salt thereof, about 41 wt % propylene glycol, about 1.75 wt % of hydroxyethyl cellulose, about 5 wt % Polysorbate 20, water, and optionally one or more of: a pH adjuster, a chelating agent, a preservative, a fragrance, and a coloring agent.

In some embodiments, the present invention provides a gel composition, consisting of about 0.025 wt % of a steroid or a pharmaceutically acceptable salt thereof, about 41 wt % propylene glycol, about 1.75 wt % of hydroxyethyl cellulose, about 5 wt % Polysorbate 20, water, trolamine, ethylenediaminetetracetic acid (EDTA) or a salt thereof, benzyl alcohol, and optionally one or more of: a fragrance and a coloring agent.

In some embodiments, the present invention provides a gel composition, consisting of about 0.025 wt % of a steroid or a pharmaceutically acceptable salt thereof, about 41 wt % propylene glycol, about 1.75 wt % of hydroxyethyl cellulose, about 5 wt % Polysorbate 20, water, about 0.17 wt % trolamine, about 0.02 wt % ethylenediaminetetracetic acid (EDTA) or a salt thereof, about 1.0 wt % benzyl alcohol, and optionally one or more of: a fragrance and a coloring agent.

In some embodiments, the present invention provides a gel composition, comprising or consisting essentially of from about 0.03 wt % to about 0.07 wt % of a steroid or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of about 0.05 wt % of a steroid or a pharmaceutically acceptable salt thereof, about 41 wt % propylene glycol, about 1.75 wt % of hydroxyethyl cellulose, about 5 wt % Polysorbate 20, water, and optionally one or more of: a pH adjuster, a chelating agent, a preservative, a fragrance, and a coloring agent.

In some embodiments, the present invention provides a gel composition, consisting of about 0.05 wt % of a steroid or a pharmaceutically acceptable salt thereof, about 41 wt % propylene glycol, about 1.75 wt % of hydroxyethyl cellulose, about 5 wt % Polysorbate 20, water, trolamine, ethylenediaminetetracetic acid (EDTA) or a salt thereof, benzyl alcohol, and optionally one or more of: a fragrance and a coloring agent.

In some embodiments, the present invention provides a gel composition, consisting of about 0.05 wt % of a steroid or a pharmaceutically acceptable salt thereof, about 41 wt % propylene glycol, about 1.75 wt % of hydroxyethyl cellulose, about 5 wt % Polysorbate 20, water, about 0.17 wt % trolamine, about 0.02 wt % ethylenediaminetetracetic acid (EDTA) or a salt thereof, about 1.0 wt % benzyl alcohol, and optionally one or more of: a fragrance and a coloring agent.

In some embodiments, the present invention provides a gel composition, comprising or consisting essentially of from about 0.01 wt % to about 4.0 wt % of a steroid or a pharmaceutically acceptable salt thereof, about 15 wt % to about 25 wt % of a glycol solvent, from about 0.75 wt % to about 2.25 wt % of a hydroxy cellulose, from about 3 wt % to about 8 wt % of a polysorbate solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, about 15 wt % to about 25 wt % of a glycol solvent, from about 0.75 wt % to about 2.25 wt % of a hydroxy cellulose, from about 3 wt % to about 8 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 4.0 wt % of a steroid or a pharmaceutically acceptable salt thereof, about 18 wt % to about 22 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 1.0 wt % of a steroid or a pharmaceutically acceptable salt thereof, about 18 wt % to about 22 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.05 wt % of a steroid or a pharmaceutically acceptable salt thereof, about 18 wt % to about 22 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of about 0.025 wt % of a steroid or a pharmaceutically acceptable salt thereof, about 20 wt % propylene glycol, about 1.75 wt % of hydroxyethyl cellulose, about 5 wt % Polysorbate 20, water, and optionally one or more of: a pH adjuster, a chelating agent, a preservative, a fragrance, and a coloring agent.

In some embodiments, the present invention provides a gel composition, consisting of about 0.025 wt % of a steroid or a pharmaceutically acceptable salt thereof, about 20 wt % propylene glycol, about 1.75 wt % of hydroxyethyl cellulose, about 5 wt % Polysorbate 20, water, ethylenediaminetetracetic acid (EDTA) or a salt thereof, and optionally one or more of: a preservative, a pH adjuster, a fragrance and a coloring agent.

In some embodiments, the present invention provides a gel composition, consisting of about 0.025 wt % of a steroid or a pharmaceutically acceptable salt thereof, about 20 wt % propylene glycol, about 1.75 wt % of hydroxyethyl cellulose, about 5 wt % Polysorbate 20, water, about 0.02 wt % ethylenediaminetetracetic acid (EDTA) or a salt thereof, and optionally one or more of: preservative, a pH adjuster, a fragrance and a coloring agent.

In some embodiments, the present invention provides a gel composition, comprising or consisting essentially of from about 0.03 wt % to about 0.07 wt % of a steroid or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of about 0.05 wt % of a steroid or a pharmaceutically acceptable salt thereof, about 20 wt % propylene glycol, about 1.75 wt % of hydroxyethyl cellulose, about 5 wt % Polysorbate 20, water, and optionally one or more of: a pH adjuster, a chelating agent, a preservative, a fragrance, and a coloring agent.

In some embodiments, the present invention provides a gel composition, consisting of about 0.05 wt % of a steroid or a pharmaceutically acceptable salt thereof, about 20 wt % propylene glycol, about 1.75 wt % of hydroxyethyl cellulose, about 5 wt % Polysorbate 20, water, ethylenediaminetetracetic acid (EDTA) or a salt thereof, and optionally one or more of: preservative, a pH adjuster, a fragrance and a coloring agent.

In some embodiments, the present invention provides a gel composition, consisting of about 0.05 wt % of a steroid or a pharmaceutically acceptable salt thereof, about 20 wt % propylene glycol, about 1.75 wt % of hydroxyethyl cellulose, about 5 wt % Polysorbate 20, water, about 0.02 wt % ethylenediaminetetracetic acid (EDTA) or a salt thereof, and optionally one or more of: preservative, a pH adjuster, a fragrance and a coloring agent.

In some embodiments, the present invention provides a gel composition, comprising or consisting essentially of from about 0.01 wt % to about 3.0 wt % of a steroid, or a pharmaceutically acceptable salt thereof, from about 10 wt % to about 30 wt % of a first solvent, from about 0.75 wt % to about 2.25 wt % of a non-carbomer rheology modifier, from about 1 wt % to less than about 10 wt % of a first solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 3.0 wt % of a steroid, or a pharmaceutically acceptable salt thereof, from about 15 wt % to about 25 wt % of a first solvent, from about 0.75 wt % to about 2.25 wt % of a non-carbomer rheology modifier, from about 1 wt % to less than about 10 wt % of a first solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of a steroid, or a pharmaceutically acceptable salt thereof, from about 15 wt % to about 25 wt % of a first solvent, from about 0.75 wt % to about 2.25 wt % of a non-carbomer rheology modifier, from about 1 wt % to less than about 10 wt % of a first solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of a steroid, or a pharmaceutically acceptable salt thereof, from about 15 wt % to about 25 wt % of a glycol solvent, from about 0.75 wt % to about 2.25 wt % of a hydroxyl cellulose, from about 1 wt % to less than about 10 wt % of a polysorbate solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of a steroid, or a pharmaceutically acceptable salt thereof, from about 15 wt % to about 25 wt % of a glycol solvent, from about 0.75 wt % to about 2.25 wt % of a hydroxy cellulose, from about 3 wt % to about 8 wt % of a polysorbate solubilizing agent, a second solubilizing agent, optionally a third solubilizing agent, and optionally one or more of: a diluent, a pH adjuster, a chelating agent, a preservative, a fragrance, and a coloring agent. In certain embodiments, the gel composition is as described above, and the optional third solubilizing agent is absent. In certain embodiments, the gel composition is as described above, and the optional third solubilizing agent is present. In certain embodiments, the gel composition is as described above, and either the second or third solubilizing agent is an alcohol solubilizing agent. In certain embodiments, the alcohol solubilizing reagent is present in an amount ranging from about 1 wt % to about 9 wt %. In certain embodiments, the alcohol solubilizing agent is present in an amount ranging from about 2 wt % to about 8 wt %. In certain embodiments, the alcohol solubilizing agent is present in an amount of about 3 wt % to about 6 wt %. In certain embodiments, the alcohol solubilizing agent is present in an amount of less than about 1 wt %. In certain embodiments, the alcohol solubilizing agent is present in an amount of about 1 wt %. In certain embodiments, the alcohol solubilizing agent is present in an amount of about 1.5 wt %. In certain embodiments, the alcohol solubilizing agent is present in an amount of about 2 wt %. In certain embodiments, the alcohol solubilizing agent is present in an amount of about 2.5 wt %. In certain embodiments, the alcohol solubilizing agent is present in an amount of about 3 wt %. In certain embodiments, the alcohol solubilizing agent is present in an amount of about 3.5 wt %. In certain embodiments, the alcohol solubilizing agent is present in an amount of about 4 wt %. In certain embodiments, the alcohol solubilizing agent is present in an amount of about 4.5 wt %. In certain embodiments, the alcohol solubilizing agent is present in an amount of about 5 wt %. In certain embodiments, the alcohol solubilizing agent is present in an amount of about 5.5 wt %. In certain embodiments, the alcohol solubilizing agent is present in an amount of about 6 wt %. In certain embodiments, the alcohol solubilizing agent is present in an amount of about 6.5 wt %. In certain embodiments, the alcohol solubilizing agent is present in an amount of about 7 wt %. In certain embodiments, the alcohol solubilizing agent is present in an amount of about 7.5 wt %. In certain embodiments, the alcohol solubilizing agent is present in an amount of about 8 wt %. In certain embodiments, the alcohol solubilizing agent is present in an amount of about 8.5 wt %. In certain embodiments, the alcohol solubilizing agent is present in an amount of about 9 wt %. In certain embodiments, the alcohol solubilizing agent is present in an amount of about 9.5 wt %. Exemplary such alcohol solubilizing agents are described above and herein and include, e.g., methanol, ethanol, propanol, and the like. In certain embodiments, the gel composition is as described above, and either the second or third solubilizing agent is a glycol ether solubilizing agent. In certain embodiments, the glycol ether solubilizing reagent is present in an amount ranging from about 1 wt % to about 9 wt %. In certain embodiments, the glycol ether solubilizing agent is present in an amount ranging from about 1 wt % to about 5 wt %. In certain embodiments, the glycol ether solubilizing agent is present in an amount of about 1 wt % to about 3 wt %. In certain embodiments, the glycol ether solubilizing agent is present in an amount of less than about 1 wt %. In certain embodiments, the glycol ether solubilizing agent is present in an amount of about 1 wt %. In certain embodiments, the glycol ether solubilizing agent is present in an amount of about 1.1 wt %. In certain embodiments, the glycol ether solubilizing agent is present in an amount of about 1.2 wt %. In certain embodiments, the glycol ether solubilizing agent is present in an amount of about 1.3 wt %. In certain embodiments, the glycol ether solubilizing agent is present in an amount of about 1.4 wt %. In certain embodiments, the glycol ether solubilizing agent is present in an amount of about 1.5 wt %. In certain embodiments, the glycol ether solubilizing agent is present in an amount of about 1.6 wt %. In certain embodiments, the glycol ether solubilizing agent is present in an amount of about 1.7 wt %. In certain embodiments, the glycol ether solubilizing agent is present in an amount of about 1.8 wt %. In certain embodiments, the glycol ether solubilizing agent is present in an amount of about 1.9 wt %. In certain embodiments, the glycol ether solubilizing agent is present in an amount of about 2.0 wt %. Exemplary such glycol ether solubilizing agents are described above and herein and include dialkylene glycol monoalkylethers such as, e.g., diethylene glycol monoethylether.

In some embodiments, the present invention provides a gel composition, comprising or consisting essentially of from about 0.01 wt % to about 2.0 wt % fluticasone, or a pharmaceutically acceptable salt thereof, from about 15 wt % to about 25 wt % propylene glycol, from about 0.75 wt % to about 2.25 wt % of hydroxyethyl cellulose, from about 3 wt % to about 8 wt % of Polysorbate 20, a second solubilizing agent, optionally a third solubilizing agent, and optionally one or more of: a diluent, a pH adjuster, a chelating agent, a preservative, a fragrance, and a coloring agent. In certain embodiments, the gel composition is as described above, and the optional third solubilizing agent is absent. In certain embodiments, the gel composition is as described above, and the optional third solubilizing agent is present. In certain embodiments, the gel composition is as described above, and either the second or third solubilizing agent is an alcohol solubilizing agent. In certain embodiments, the alcohol solubilizing reagent is present in an amount ranging from about 1 wt % to about 9 wt %. In certain embodiments, the alcohol solubilizing agent is present in an amount ranging from about 2 wt % to about 8 wt %. In certain embodiments, the alcohol solubilizing agent is present in an amount of about 3 wt % to about 6 wt %. In certain embodiments, the alcohol solubilizing agent is present in an amount of less than about 1 wt %. In certain embodiments, the alcohol solubilizing agent is present in an amount of about 1 wt %. In certain embodiments, the alcohol solubilizing agent is present in an amount of about 1.5 wt %. In certain embodiments, the alcohol solubilizing agent is present in an amount of about 2 wt %. In certain embodiments, the alcohol solubilizing agent is present in an amount of about 2.5 wt %. In certain embodiments, the alcohol solubilizing agent is present in an amount of about 3 wt %. In certain embodiments, the alcohol solubilizing agent is present in an amount of about 3.5 wt %. In certain embodiments, the alcohol solubilizing agent is present in an amount of about 4 wt %. In certain embodiments, the alcohol solubilizing agent is present in an amount of about 4.5 wt %. In certain embodiments, the alcohol solubilizing agent is present in an amount of about 5 wt %. In certain embodiments, the alcohol solubilizing agent is present in an amount of about 5.5 wt %. In certain embodiments, the alcohol solubilizing agent is present in an amount of about 6 wt %. In certain embodiments, the alcohol solubilizing agent is present in an amount of about 6.5 wt %. In certain embodiments, the alcohol solubilizing agent is present in an amount of about 7 wt %. In certain embodiments, the alcohol solubilizing agent is present in an amount of about 7.5 wt %. In certain embodiments, the alcohol solubilizing agent is present in an amount of about 8 wt %. In certain embodiments, the alcohol solubilizing agent is present in an amount of about 8.5 wt %. In certain embodiments, the alcohol solubilizing agent is present in an amount of about 9 wt %. In certain embodiments, the alcohol solubilizing agent is present in an amount of about 9.5 wt %. Exemplary such alcohol solubilizing agents are described above and herein and include, e.g., methanol, ethanol, propanol, and the like. In certain embodiments, the gel composition is as described above, and either the second or third solubilizing agent is a glycol ether solubilizing agent. In certain embodiments, the glycol ether solubilizing reagent is present in an amount ranging from about 1 wt % to about 9 wt %. In certain embodiments, the glycol ether solubilizing agent is present in an amount ranging from about 1 wt % to about 5 wt %. In certain embodiments, the glycol ether solubilizing agent is present in an amount of about 1 wt % to about 3 wt %. In certain embodiments, the glycol ether solubilizing agent is present in an amount of less than about 1 wt %. In certain embodiments, the glycol ether solubilizing agent is present in an amount of about 1 wt %. In certain embodiments, the glycol ether solubilizing agent is present in an amount of about 1.1 wt %. In certain embodiments, the glycol ether solubilizing agent is present in an amount of about 1.2 wt %. In certain embodiments, the glycol ether solubilizing agent is present in an amount of about 1.3 wt %. In certain embodiments, the glycol ether solubilizing agent is present in an amount of about 1.4 wt %. In certain embodiments, the glycol ether solubilizing agent is present in an amount of about 1.5 wt %. In certain embodiments, the glycol ether solubilizing agent is present in an amount of about 1.6 wt %. In certain embodiments, the glycol ether solubilizing agent is present in an amount of about 1.7 wt %. In certain embodiments, the glycol ether solubilizing agent is present in an amount of about 1.8 wt %. In certain embodiments, the glycol ether solubilizing agent is present in an amount of about 1.9 wt %. In certain embodiments, the glycol ether solubilizing agent is present in an amount of about 2.0 wt %. Exemplary such glycol ether solubilizing agents are described above and herein and include dialkylene glycol monoalkylethers such as, e.g., diethylene glycol monoethylether.

In some embodiments, the present invention provides a gel composition, comprising or consisting essentially of about 0.025 wt % fluticasone, or a pharmaceutically acceptable salt thereof, about 20 wt % propylene glycol, about 1.75 wt % hydroxyethyl cellulose, about 5 wt % of Polysorbate 20, a second solubilizing agent, optionally a third solubilizing agent, and optionally one or more of: a diluent, a pH adjuster, a chelating agent, a preservative, a fragrance, and a coloring agent. In certain embodiments, the gel composition is as described above, and the optional third solubilizing agent is absent. In certain embodiments, the gel composition is as described above, and the optional third solubilizing agent is present. In certain embodiments, the gel composition is as described above, and either the second or third solubilizing agent is an alcohol solubilizing agent. In certain embodiments, the alcohol solubilizing reagent is present in an amount ranging from about 1 wt % to about 9 wt %. In certain embodiments, the alcohol solubilizing agent is present in an amount ranging from about 2 wt % to about 8 wt %. In certain embodiments, the alcohol solubilizing agent is present in an amount of about 3 wt % to about 6 wt %. In certain embodiments, the alcohol solubilizing agent is present in an amount of less than about 1 wt %. In certain embodiments, the alcohol solubilizing agent is present in an amount of about 1 wt %. In certain embodiments, the alcohol solubilizing agent is present in an amount of about 1.5 wt %. In certain embodiments, the alcohol solubilizing agent is present in an amount of about 2 wt %. In certain embodiments, the alcohol solubilizing agent is present in an amount of about 2.5 wt %. In certain embodiments, the alcohol solubilizing agent is present in an amount of about 3 wt %. In certain embodiments, the alcohol solubilizing agent is present in an amount of about 3.5 wt %. In certain embodiments, the alcohol solubilizing agent is present in an amount of about 4 wt %. In certain embodiments, the alcohol solubilizing agent is present in an amount of about 4.5 wt %. In certain embodiments, the alcohol solubilizing agent is present in an amount of about 5 wt %. In certain embodiments, the alcohol solubilizing agent is present in an amount of about 5.5 wt %. In certain embodiments, the alcohol solubilizing agent is present in an amount of about 6 wt %. In certain embodiments, the alcohol solubilizing agent is present in an amount of about 6.5 wt %. In certain embodiments, the alcohol solubilizing agent is present in an amount of about 7 wt %. In certain embodiments, the alcohol solubilizing agent is present in an amount of about 7.5 wt %. In certain embodiments, the alcohol solubilizing agent is present in an amount of about 8 wt %. In certain embodiments, the alcohol solubilizing agent is present in an amount of about 8.5 wt %. In certain embodiments, the alcohol solubilizing agent is present in an amount of about 9 wt %. In certain embodiments, the alcohol solubilizing agent is present in an amount of about 9.5 wt %. Exemplary such alcohol solubilizing agents are described above and herein and include, e.g., methanol, ethanol, propanol, and the like. In certain embodiments, the gel composition is as described above, and either the second or third solubilizing agent is a glycol ether solubilizing agent. In certain embodiments, the glycol ether solubilizing reagent is present in an amount ranging from about 1 wt % to about 9 wt %. In certain embodiments, the glycol ether solubilizing agent is present in an amount ranging from about 1 wt % to about 5 wt %. In certain embodiments, the glycol ether solubilizing agent is present in an amount of about 1 wt % to about 3 wt %. In certain embodiments, the glycol ether solubilizing agent is present in an amount of less than about 1 wt %. In certain embodiments, the glycol ether solubilizing agent is present in an amount of about 1 wt %. In certain embodiments, the glycol ether solubilizing agent is present in an amount of about 1.1 wt %. In certain embodiments, the glycol ether solubilizing agent is present in an amount of about 1.2 wt %. In certain embodiments, the glycol ether solubilizing agent is present in an amount of about 1.3 wt %. In certain embodiments, the glycol ether solubilizing agent is present in an amount of about 1.4 wt %. In certain embodiments, the glycol ether solubilizing agent is present in an amount of about 1.5 wt %. In certain embodiments, the glycol ether solubilizing agent is present in an amount of about 1.6 wt %. In certain embodiments, the glycol ether solubilizing agent is present in an amount of about 1.7 wt %. In certain embodiments, the glycol ether solubilizing agent is present in an amount of about 1.8 wt %. In certain embodiments, the glycol ether solubilizing agent is present in an amount of about 1.9 wt %. In certain embodiments, the glycol ether solubilizing agent is present in an amount of about 2.0 wt %. Exemplary such glycol ether solubilizing agents are described above and herein and include dialkylene glycol monoalkylethers such as, e.g., diethylene glycol monoethylether.

In some embodiments, the present invention provides a gel composition, comprising or consisting essentially of from about 0.01 wt % to about 2.0 wt % of a steroid, or a pharmaceutically acceptable salt thereof, from about 15 wt % to about 25 wt % of a glycol solvent, from about 0.75 wt % to about 2.25 wt % of a hydroxy cellulose, from about 3 wt % to about 8 wt % of a polysorbate solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of a steroid, or a pharmaceutically acceptable salt thereof, from about 15 wt % to about 25 wt % propylene glycol, from about 0.75 wt % to about 2.25 wt % of hydroxyethyl cellulose, from about 3 wt % to about 8 wt % of Polysorbate 20, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of a steroid, or a pharmaceutically acceptable salt thereof, from about 15 wt % to about 25 wt % propylene glycol, from about 0.75 wt % to about 2.25 wt % of hydroxyethyl cellulose, from about 3 wt % to about 8 wt % of Polysorbate 20, from about 1 wt % to less than about 10 wt % of a second solubilizing agent selected from an alcohol or glycol ether solubilizing agent, optionally from about 1 wt % to less than about 10 wt % of a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of a steroid, or a pharmaceutically acceptable salt thereof, from about 15 wt % to about 25 wt % propylene glycol, from about 0.75 wt % to about 2.25 wt % of hydroxyethyl cellulose, from about 3 wt % to about 8 wt % of Polysorbate 20, from about 1 wt % to less than about 10 wt % of a second solubilizing agent selected from an alcohol or glycol ether solubilizing agent, optionally from about 1 wt % to less than about 10 wt % of a third solubilizing agent selected from an alcohol or glycol ether solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of a steroid, or a pharmaceutically acceptable salt thereof, from about 15 wt % to about 25 wt % propylene glycol, from about 0.75 wt % to about 2.25 wt % of hydroxyethyl cellulose, from about 3 wt % to about 8 wt % of Polysorbate 20, from about 7 wt % to about 9 wt % of an alcohol solubilizing agent, optionally from about 1 wt % to about 3 wt % of a glycol ether solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 2.0 wt % of a steroid, or a pharmaceutically acceptable salt thereof, from about 15 wt % to about 25 wt % propylene glycol, from about 0.75 wt % to about 2.25 wt % of hydroxyethyl cellulose, from about 3 wt % to about 8 wt % of Polysorbate 20, from about 1 wt % to about 3 wt % of a glycol ether solubilizing agent, optionally from about 3 wt % to about 8 wt % of an alcohol solubilizing agent selected, and optionally one or more of: a diluent, a pH adjuster, a chelating agent, a preservative, a fragrance, and a coloring agent.

Fluticasone

In some embodiments, the present invention provides a gel composition, comprising or consisting essentially of from about 0.01 wt % to about 0.1 wt % fluticasone or a pharmaceutically acceptable salt thereof, not more than 40 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, not more than 35 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, not more than 30 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, not more than 25 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, not more than 20 wt % of a first solvent, from about 0.75 wt % to about 2.25 wt % of a non-carbomer rheology modifier, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, about 30 wt % to about 50 wt % of a glycol solvent, from about 0.75 wt % to about 2.25 wt % of a hydroxy cellulose, from about 1 wt % to less than about 10 wt % of a first solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, about 30 wt % to about 50 wt % of a glycol solvent, from about 0.75 wt % to about 2.25 wt % of a hydroxy cellulose, from about 3 wt % to about 8 wt % of a polysorbate solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, about 30 wt % to about 50 wt % of a glycol solvent, from about 0.75 wt % to about 2.25 wt % of a hydroxy cellulose, from about 3 wt % to about 8 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.075 wt % fluticasone or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.075 wt % fluticasone or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of about 0.025 wt % fluticasone or a pharmaceutically acceptable salt thereof, about 41 wt % propylene glycol, about 1.75 wt % of hydroxyethyl cellulose, about 5 wt % Polysorbate 20, water, and optionally one or more of: a pH adjuster, a chelating agent, a preservative, a fragrance, and a coloring agent.

In some embodiments, the present invention provides a gel composition, consisting of about 0.025 wt % fluticasone or a pharmaceutically acceptable salt thereof, about 41 wt % propylene glycol, about 1.75 wt % of hydroxyethyl cellulose, about 5 wt % Polysorbate 20, water, trolamine, ethylenediaminetetracetic acid (EDTA) or a salt thereof, benzyl alcohol, and optionally one or more of: a fragrance and a coloring agent.

In some embodiments, the present invention provides a gel composition, consisting of about 0.025 wt % fluticasone or a pharmaceutically acceptable salt thereof, about 41 wt % propylene glycol, about 1.75 wt % of hydroxyethyl cellulose, about 5 wt % Polysorbate 20, water, about 0.17 wt % trolamine, about 0.02 wt % ethylenediaminetetracetic acid (EDTA) or a salt thereof, about 1.0 wt % benzyl alcohol, and optionally one or more of: a fragrance and a coloring agent.

In some embodiments, the present invention provides a gel composition, comprising or consisting essentially of from about 0.03 wt % to about 0.07 wt % fluticasone or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of about 0.05 wt % fluticasone or a pharmaceutically acceptable salt thereof, about 41 wt % propylene glycol, about 1.75 wt % of hydroxyethyl cellulose, about 5 wt % Polysorbate 20, water, and optionally one or more of: a pH adjuster, a chelating agent, a preservative, a fragrance, and a coloring agent.

In some embodiments, the present invention provides a gel composition, consisting of about 0.05 wt % fluticasone or a pharmaceutically acceptable salt thereof, about 41 wt % propylene glycol, about 1.75 wt % of hydroxyethyl cellulose, about 5 wt % Polysorbate 20, water, trolamine, ethylenediaminetetracetic acid (EDTA) or a salt thereof, benzyl alcohol, and optionally one or more of: a fragrance and a coloring agent.

In some embodiments, the present invention provides a gel composition, consisting of about 0.05 wt % fluticasone or a pharmaceutically acceptable salt thereof, about 41 wt % propylene glycol, about 1.75 wt % of hydroxyethyl cellulose, about 5 wt % Polysorbate 20, water, about 0.17 wt % trolamine, about 0.02 wt % ethylenediaminetetracetic acid (EDTA) or a salt thereof, about 1.0 wt % benzyl alcohol, and optionally one or more of: a fragrance and a coloring agent.

In some embodiments, the present invention provides a gel composition, comprising or consisting essentially of from about 0.01 wt % to about 0.1 wt % fluticasone or a pharmaceutically acceptable salt thereof, about 15 wt % to about 25 wt % of a glycol solvent, from about 0.75 wt % to about 2.25 wt % of a hydroxy cellulose, from about 3 wt % to about 8 wt % of a polysorbate solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, about 15 wt % to about 25 wt % of a glycol solvent, from about 0.75 wt % to about 2.25 wt % of a hydroxy cellulose, from about 3 wt % to about 8 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone or a pharmaceutically acceptable salt thereof, about 18 wt % to about 22 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.075 wt % fluticasone or a pharmaceutically acceptable salt thereof, about 18 wt % to about 22 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of about 0.025 wt % fluticasone or a pharmaceutically acceptable salt thereof, about 20 wt % propylene glycol, about 1.75 wt % of hydroxyethyl cellulose, about 5 wt % Polysorbate 20, water, and optionally one or more of: a pH adjuster, a chelating agent, a preservative, a fragrance, and a coloring agent.

In some embodiments, the present invention provides a gel composition, consisting of about 0.025 wt % fluticasone or a pharmaceutically acceptable salt thereof, about 20 wt % propylene glycol, about 1.75 wt % of hydroxyethyl cellulose, about 5 wt % Polysorbate 20, water, ethylenediaminetetracetic acid (EDTA) or a salt thereof, and optionally one or more of: a preservative, a pH adjuster, a fragrance and a coloring agent.

In some embodiments, the present invention provides a gel composition, consisting of about 0.025 wt % fluticasone or a pharmaceutically acceptable salt thereof, about 20 wt % propylene glycol, about 1.75 wt % of hydroxyethyl cellulose, about 5 wt % Polysorbate 20, water, about 0.02 wt % ethylenediaminetetracetic acid (EDTA) or a salt thereof, and optionally one or more of: preservative, a pH adjuster, a fragrance and a coloring agent.

In some embodiments, the present invention provides a gel composition, comprising or consisting essentially of from about 0.03 wt % to about 0.07 wt % fluticasone or a pharmaceutically acceptable salt thereof, about 35 wt % to about 45 wt % propylene glycol, from about 1.5 wt % to about 2.0 wt % of hydroxyethyl cellulose, from about 4 wt % to about 6 wt % Polysorbate 20, and optionally one or more of: a diluent, a pH adjuster, a chelating agent, a preservative, a fragrance, and a coloring agent.

In some embodiments, the present invention provides a gel composition, comprising or consisting essentially of about 0.05 wt % fluticasone or a pharmaceutically acceptable salt thereof, about 20 wt % propylene glycol, about 1.75 wt % of hydroxyethyl cellulose, about 5 wt % Polysorbate 20, water, and optionally one or more of: a pH adjuster, a chelating agent, a preservative, a fragrance, and a coloring agent.

In some embodiments, the present invention provides a gel composition, consisting of about 0.05 wt % fluticasone or a pharmaceutically acceptable salt thereof, about 20 wt % propylene glycol, about 1.75 wt % of hydroxyethyl cellulose, about 5 wt % Polysorbate 20, water, ethylenediaminetetracetic acid (EDTA) or a salt thereof, and optionally one or more of: preservative, a pH adjuster, a fragrance and a coloring agent.

In some embodiments, the present invention provides a gel composition, consisting of about 0.05 wt % fluticasone or a pharmaceutically acceptable salt thereof, about 20 wt % propylene glycol, about 1.75 wt % of hydroxyethyl cellulose, about 5 wt % Polysorbate 20, water, about 0.02 wt % ethylenediaminetetracetic acid (EDTA) or a salt thereof, and optionally one or more of: preservative, a pH adjuster, a fragrance and a coloring agent.

In some embodiments, the present invention provides a gel composition comprising or consisting essentially of:
 (i) an active agent selected from a steroid;
 (ii) a first solvent selected from a glycol solvent;
 (iii) a second solvent selected from an alkyl alcohol solvent;
 (iv) a non-carbomer rheology modifier selected from a hydroxyl cellulose;
 (v) a solubolzing agent selected from a polysorbate solubilizing agent; and
optionally one or more of: an additional solubilizing agent, a diluent, a preservative, a pH adjuster, a chelating agent, a coloring agent, and a fragrance.

In some embodiments, the present invention provides a gel composition wherein the active agent a steroid or a salt thereof. In some embodiments, the present invention provides a gel composition wherein the active agent is fluticasone propionate.

In some embodiments, the present invention provides a gel pharmaceutical composition, comprising or consisting essentially of fluticasone or pharmaceutically acceptable salt thereof, in an amount of from about 0.01 wt % to about 0.1 wt %, propylene glycol in an amount of about 20 wt %, ethanol in an amount of about 19 wt %, hydroxyethyl cellulose in an amount of about 1.75 wt %, Polysorbate 20 in an amount of about 5 wt %, water, and optionally one or more of: a pH adjuster, a chelating agent, a preservative, a fragrance, and a coloring agent. In certain embodiments, the gel composition is as described above, with the exception that Polysorbate 20 is replaced with Polysorbate 80.

In some embodiments, the present invention provides a gel composition, comprising or consisting essentially of fluticasone or pharmaceutically acceptable salt thereof, in an amount of from about 0.01 wt % to about 0.075 wt %, about 20 wt % propylene glycol, about 19 wt % ethanol, about 1.75 wt % hydroxyethyl cellulose, about 5 wt % Polysorbate 20, water, ethylenediaminetetracetic acid (EDTA) or a salt thereof, benzyl alcohol, and optionally one or more of: a pH adjuster, a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of fluticasone or pharmaceutically acceptable salt thereof, in an amount of from about 0.01 wt % to about 0.075 wt %, about 20 wt % propylene glycol, about 19 wt % ethanol, about 1.75 wt % hydroxyethyl cellulose, about 5 wt % Polysorbate 20, water, about 0.02 wt % ethylenediaminetetracetic acid (EDTA) or a salt thereof, about 1.0 wt % benzyl alcohol, and optionally one or more of: a pH adjuster, a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of fluticasone or pharmaceutically acceptable salt thereof in an amount of about 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, or 0.075 wt %, about 20 wt % propylene glycol, about 19 wt % ethanol, about 1.75 wt % hydroxyethyl cellulose, about 5 wt % Polysorbate 20, water, about 0.02 wt % ethylenediaminetetracetic acid (EDTA) or a salt thereof, about 1.0 wt % benzyl alcohol, and optionally one or more of: a pH adjuster, a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of fluticasone or pharmaceutically acceptable salt thereof in an amount of about 0.025 wt % or about 0.05 wt %, propylene glycol in an amount of about 20 wt %, ethanol in an amount of about 19 wt %, Polysorbate 20 in an amount of about 5 wt %, hydroxyethyl cellulose in an amount of about 1.75 wt %, and water. In certain embodiments, the gel composition is as described above, with the exception that Polysorbate 20 is replaced with Polysorbate 80.

In some embodiments, the present invention provides a gel composition, comprising or consisting essentially of fluticasone or pharmaceutically acceptable salt thereof in an amount of about 0.025 wt % or about 0.05 wt %, about 20 wt % propylene glycol, about 19 wt % ethanol, about 1.75 wt % hydroxyethyl cellulose, about 5 wt % Polysorbate 20, water, about 0.02 wt % ethylenediaminetetracetic acid (EDTA) or a salt thereof, about 1.0 wt % benzyl alcohol, and optionally one or more of: a pH adjuster, a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of fluticasone propionate in an amount of about 0.025 wt % or about 0.05 wt %, about 20 wt % propylene glycol, about 19 wt % ethanol, about 1.75 wt % hydroxyethyl cellulose, about 5 wt % Polysorbate 20, water, about 0.02 wt % ethylenediaminetetracetic acid (EDTA) or a salt thereof, about 1.0 wt % benzyl alcohol, and optionally one or more of: a pH adjuster, a fragrance and a coloring agent. In certain embodiments, the gel composition is as described above, with the exception that Polysorbate 20 is replaced with Polysorbate 80.

In some embodiments, the present invention provides a gel composition, comprising or consisting essentially of fluticasone propionate in an amount of about 0.025 wt % or about 0.05 wt %, about 20 wt % propylene glycol, about 19 wt % ethanol, about 1.75 wt % hydroxyethyl cellulose, about 5 wt % Polysorbate 20, water, about 0.17 wt % trolamine, about 0.02 wt % ethylenediaminetetracetic acid (EDTA) or a salt thereof, and about 1.0 wt % benzyl alcohol. In certain embodiments, the gel composition is as described above, with the exception that Polysorbate 20 is replaced with Polysorbate 80.

In some embodiments, the present invention provides a gel composition for topical administration consisting essentially of:
 (i) fluticasone or a pharmaceutically acceptable salt thereof, present in an amount of from about 0.01 wt % to about 0.075 wt %;
 (ii) a first solvent which is a glycol solvent present in an amount of from about 10 wt % to about 25 wt %;
 (iii) a second solvent which is an alcohol solvent present in an amount of from about 10 wt % to about 25 wt %;
 (iv) a non-carbomer rheology modifier; and optionally one or more of: a solubilizing agent, water, a preservative, a pH adjuster, a chelating agent, a coloring agent, and a fragrance.

In certain embodiments, the gel composition is as described above, wherein the fluticasone or a pharmaceutically acceptable salt thereof is present in an amount of about 0.025 wt % or 0.05 wt %. In certain embodiments, the gel composition is as described above, wherein the glycol solvent is present in an amount of about 18 wt % to about 22 wt %. In certain embodiments, the gel composition is as described above, wherein the glycol solvent is propylene glycol. In certain embodiments, the gel composition is as described above, wherein the alcohol is present in an amount of from about 17 wt % to about 22 wt %. In certain embodiments, the gel composition is as described above, wherein the alcohol is ethanol. In certain embodiments, the gel composition is as described above, wherein the non-carbomer rheology modifier is a hydroxy cellulose. In certain embodiments, the gel composition is as described above, wherein the hydroxy cellulose is present in an amount of from about 0.75 wt % to about 2.25 wt %. In certain embodiments, the gel composition is as described above, wherein the hydroxy cellulose hydroxyethyl cellulose. In certain embodiments, the gel composition is as described above, wherein at least one of the one or more solubilizing agents is a polysorbate solubilizing agent. In certain embodiments, the gel composition is as described above, wherein the polysorbate solubilizing agent is present in an amount of from about 3 wt % to about 8 wt %. In certain embodiments, the gel composition is as described above, wherein the polysorbate solubilizing agent is Polysorbate 20 or Polysorbate 80. In certain embodiments, the gel composition is as described above, wherein the fluticasone or pharmaceutically acceptable salt thereof is fluticasone propionate. In certain embodiments, the gel composition is as described above, wherein the fluticasone or a pharmaceutically acceptable salt thereof (e.g., fluticasone propionate) is present in an amount of about 0.025 wt % or about 0.05 wt %, the glycol solvent (e.g., propylene glycol) is present in an amount of about 20 wt %, the alcohol solvent (e.g., ethanol) is present in an amount of about 19 wt %, the non-carbomer rheology modifier (e.g., hydroxyethyl cellulose) is present in an amount of about 1.75 wt %, and the solubilizing agent is a polysorbate (e.g., Polysorbate 20 or Polysorbate 80) present in an amount of about 5 wt %.

In some embodiments, the present invention provides a gel composition, comprising or consisting essentially of from about 0.01 wt % to about 1.0 wt % fluticasone, or a pharmaceutically acceptable salt thereof, from about 10 wt % to about 30 wt % of a first solvent, from about 0.75 wt % to about 2.25 wt % of a non-carbomer rheology modifier, from about 1 wt % to less than about 10 wt % of a first solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 1.0 wt % fluticasone, or a pharmaceutically acceptable salt thereof, from about 15 wt % to about 25 wt % of a first solvent, from about 0.75 wt % to about 2.25 wt % of a non-carbomer rheology modifier, from about 1 wt % to less than about 10 wt % of a first solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.5 wt % fluticasone, or a pharmaceutically acceptable salt thereof, from about 15 wt % to about 25 wt % of a first solvent, from about 0.75 wt % to about 2.25 wt % of a non-carbomer rheology modifier, from about 1 wt % to less than about 10 wt % of a first solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.5 wt % fluticasone, or a pharmaceutically acceptable salt thereof, from about 15 wt % to about 25 wt % of a glycol solvent, from about 0.75 wt % to about 2.25 wt % of a hydroxyl cellulose, from about 1 wt % to less than about 10 wt % of a polysorbate solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone, or a pharmaceutically acceptable salt thereof, from about 15 wt % to about 25 wt % of a glycol solvent, from about 0.75 wt % to about 2.25 wt % of a hydroxy cellulose, from about 3 wt % to about 8 wt % of a polysorbate solubilizing agent, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone, or a pharmaceutically acceptable salt thereof, from about 15 wt % to about 25 wt % propylene glycol, from about 0.75 wt % to about 2.25 wt % hydroxyethyl cellulose, from about 3 wt % to about 8 wt % Polysorbate 20, from about 1 wt % to less than about 10 wt % of a second solubilizing agent, optionally a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.1 wt % fluticasone, or a pharmaceutically acceptable salt thereof, from about 15 wt % to about 25 wt % propylene glycol, from about 1.5 wt % to about 2.0 wt % hydroxyethyl cellulose, from about 3 wt % to about 8 wt % Polysorbate 20, from about 1 wt % to less than about 10 wt % of a second solubilizing agent selected from an alcohol or glycol ether solubilizing agent, optionally from about 1 wt % to less than about 10 wt % of a third solubilizing agent, and optionally one or more of: a diluent, a pH adjuster, a chelating agent, a preservative, a fragrance, and a coloring agent.

In some embodiments, the present invention provides a gel composition, comprising or consisting essentially of from about 0.01 wt % to about 0.075 wt % fluticasone, or a pharmaceutically acceptable salt thereof, from about 15 wt % to about 25 wt % propylene glycol, from about 1.5 wt % to about 2.0 wt % hydroxyethyl cellulose, from about 3 wt % to about 8 wt % Polysorbate 20, from about 1 wt % to less than about 10 wt % of a second solubilizing agent selected from an alcohol or glycol ether solubilizing agent, optionally from about 1 wt % to less than about 10 wt % of a third solubilizing agent selected from an alcohol or glycol ether solubilizing agent, and optionally one or more of: a diluent, a pH adjuster, a chelating agent, a preservative, a fragrance, and a coloring agent.

In some embodiments, the present invention provides a gel composition, comprising or consisting essentially of about 0.025 wt % fluticasone, or a pharmaceutically acceptable salt thereof, about 20 wt % propylene glycol, about 1.75 wt % hydroxyethyl cellulose, about 5 wt % Polysorbate 20, about 5 wt % ethanol, and optionally one or more of: a diluent, a pH adjuster, a chelating agent, a preservative, a fragrance, and a coloring agent. In certain embodiments, the gel composition is as described above and further comprises diethylene glycol monoethylether in an amount of from about 1 wt % to about 3 wt %. For instance, in certain embodiments, the present invention provides a gel composition, comprising or consisting essentially of about 0.025 wt % fluticasone, or a pharmaceutically acceptable salt thereof, about 20 wt % propylene glycol, about 1.75 wt % hydroxyethyl cellulose, about 5 wt % Polysorbate 20, about 5 wt % ethanol, about 1.5 wt % diethylene glycol monoethylether, and optionally one or more of: a diluent, a pH adjuster, a chelating agent, a preservative, a fragrance, and a coloring agent.

In some embodiments, the present invention provides a gel composition, comprising or consisting essentially of about 0.05 wt % fluticasone, or a pharmaceutically acceptable salt thereof, about 20 wt % propylene glycol, about 1.75 wt % hydroxyethyl cellulose, about 5 wt % Polysorbate 20, about 5 wt % ethanol, and optionally one or more of: a diluent, a pH adjuster, a chelating agent, a preservative, a fragrance, and a coloring agent. In certain embodiments, the gel composition is as described above and further comprises diethylene glycol monoethylether in an amount of from about 1 wt % to about 3 wt %. For instance, in certain embodiments, the present invention provides a gel composition, comprising or consisting essentially of about 0.05 wt % fluticasone, or a pharmaceutically acceptable salt thereof, about 20 wt % propylene glycol, about 1.75 wt % hydroxyethyl cellulose, about 5 wt % Polysorbate 20, about 5 wt % ethanol, about 1.5 wt % diethylene glycol monoethylether, and optionally one or more of: a diluent, a pH adjuster, a chelating agent, a preservative, a fragrance, and a coloring agent.

In some embodiments, the present invention provides a gel composition, comprising or consisting essentially of about 0.025 wt % fluticasone, or a pharmaceutically acceptable salt thereof, about 20 wt % propylene glycol, about 1.75 wt % hydroxyethyl cellulose, about 5 wt % Polysorbate 20, about 5 wt % ethanol, about 1.5 wt % diethylene glycol monoethylether, water, 0.02 wt % ethylenediaminetetracetic acid (EDTA) or a salt thereof, and optionally a preservative, a pH adjuster, a fragrance, and a coloring agent.

In some embodiments, the present invention provides a gel composition, comprising or consisting essentially of about 0.05 wt % fluticasone, or a pharmaceutically acceptable salt thereof, about 20 wt % propylene glycol, about 1.75 wt % hydroxyethyl cellulose, about 5 wt % Polysorbate 20, about 5 wt % ethanol, about 1.5 wt % diethylene glycol monoethylether, water, 0.02 wt % ethylenediaminetetracetic acid (EDTA) or a salt thereof, and optionally a preservative, a pH adjuster, a fragrance, and a coloring agent.

In some embodiments, the present invention provides a gel composition, comprising or consisting essentially of about 0.025 wt % fluticasone, or a pharmaceutically acceptable salt thereof, about 20 wt % propylene glycol, about 1.75 wt % of hydroxyethyl cellulose, about 5 wt % Polysorbate 20, from about 7 wt % to about 9 wt % ethanol, and optionally one or more of: a diluent, a pH adjuster, a chelating agent, a preservative, a fragrance, and a coloring agent. For instance, in certain embodiments, the present invention provides a gel composition, comprising or consisting essentially of about 0.025 wt % fluticasone, or a pharmaceutically acceptable salt thereof, about 20 wt % propylene glycol, about 1.75 wt % of hydroxyethyl cellulose, about 5 wt % Polysorbate 20, about 8 wt % ethanol, water, 0.02 wt % ethylenediaminetetracetic acid (EDTA) or a salt thereof, and optionally a preservative, a pH adjuster, a fragrance, and a coloring agent. In certain embodiments, the gel composition is as described above and further comprises diethylene glycol monoethylether in an amount of from about 1 wt % to about 3 wt %.

In some embodiments, the present invention provides a gel composition, comprising or consisting essentially of about 0.05 wt % fluticasone, or a pharmaceutically acceptable salt thereof, about 20 wt % propylene glycol, about 1.75 wt % of hydroxyethyl cellulose, about 5 wt % Polysorbate 20, from about 7 wt % to about 9 wt % ethanol, and optionally one or more of: a diluent, a pH adjuster, a chelating agent, a preservative, a fragrance, and a coloring agent. For instance, in certain embodiments, the present invention provides a gel composition, comprising or consisting essentially of about 0.05 wt % fluticasone, or a pharmaceutically acceptable salt thereof, about 20 wt % propylene glycol, about 1.75 wt % of hydroxyethyl cellulose, about 5 wt % Polysorbate 20, about 8 wt % ethanol, water, 0.02 wt % ethylenediaminetetracetic acid (EDTA) or a salt thereof, and optionally a preservative, a pH adjuster, a fragrance, and a coloring agent. In certain embodiments, the gel composition is as described above and further comprises diethylene glycol monoethylether in an amount of from about 1 wt % to about 3 wt %.

In some embodiments, the present invention provides a gel composition, comprising or consisting essentially of about 0.025 wt % fluticasone, or a pharmaceutically acceptable salt thereof, about 20 wt % propylene glycol, about 1.5 wt % to about 2.0 wt % hydroxyethyl cellulose, from about 3 wt % to about 8 wt % Polysorbate 20, from about 1 wt % to about 3 wt % of a glycol ether solubilizing agent, and optionally one or more of: a diluent, a pH adjuster, a chelating agent, a preservative, a fragrance, and a coloring agent. For instance, in certain embodiments, the present invention provides a gel composition, comprising or consisting essentially of about 0.025 wt % fluticasone, or a pharmaceutically acceptable salt thereof, about 20 wt % propylene glycol, about 1.75 wt % hydroxyethyl cellulose, about 5 wt % Polysorbate 20, about 1.5 wt % diethylene glycol monoethylether, water, 0.02 wt % ethylenediaminetetracetic acid (EDTA) or a salt thereof, and optionally a preservative, a pH adjuster, a fragrance, and a coloring agent.

In some embodiments, the present invention provides a gel composition, comprising or consisting essentially of about 0.05 wt % fluticasone, or a pharmaceutically acceptable salt thereof, about 20 wt % propylene glycol, about 1.5 wt % to about 2.0 wt % hydroxyethyl cellulose, from about 3 wt % to about 8 wt % Polysorbate 20, from about 1 wt % to about 3 wt % of a glycol ether solubilizing agent, and optionally one or more of: a diluent, a pH adjuster, a chelating agent, a preservative, a fragrance, and a coloring agent. For instance, in certain embodiments, the present invention provides a gel composition, comprising or consisting essentially of about 0.05 wt % fluticasone, or a pharmaceutically acceptable salt thereof, about 20 wt % propylene glycol, about 1.75 wt % hydroxyethyl cellulose, about 5 wt % Polysorbate 20, about 1.5 wt % diethylene glycol monoethylether, water, 0.02 wt % ethylenediaminetetracetic acid (EDTA) or a salt thereof, and optionally a preservative, a pH adjuster, a fragrance, and a coloring agent.

Methods of Treatment

The presently described subject matter relates to a method of treating a condition, disease or disorder in a subject, comprising: topically administering to a subject in need thereof, a therapeutically effective amount of any presently described topical gel composition. In some embodiments, the present invention provides a method for treating a superficial disease, disorder, or condition in a subject, comprises topically administering to the subject a therapeutically effective amount of a provided topical gel composition. In some embodiments, the superficial disease, disorder, or condition is selected from a superficial microbial infection or an inflammatory disease, disorder, or condition.

Methods of Treating Microbial Infections

In some embodiments, the present invention provides a method of treating a microbial infection in a subject, comprising: topically administering to a subject in need thereof a therapeutically effective amount of any presently described topical gel composition useful in treating a microbial infection.

In some embodiments, administration of a provided gel composition reduces the number of microbes, preferably pathogenic microbes, in or on the mammal to which it is administered. The microbes that can be acted on by the present compositions are selected from the group consisting of fungi, molds, yeast and combinations thereof.

In some embodiments, the presently described subject matter relates to a method for treating a condition, disease or disorder in a subject, wherein the condition, disease or disorder is a fungal infection. In certain embodiments, the fungal infection is a fungal infection of the skin. In certain embodiments, the fungal infection is a fungal infection of the nail. In certain embodiments, the fungal infection is a fungal infection of the hair follicle.

In some embodiments, the presently described subject matter relates to the use of a presently described composition to treat a microbial infection in a subject by topically administering the composition to the subject in need thereof.

In some embodiments, the presently described subject matter relates to the use of a presently described composition to treat a fungal infection in a subject by topically administering the composition to the subject in need thereof.

In some embodiments, the presently described subject matter relates to the use of an antifungal agent or a pharmaceutically salt thereof in the manufacture of a medicament for the treatment of a fungal infection.

In some embodiments, the presently described subject matter relates to the use of naftifine, or a pharmaceutically salt thereof, in the manufacture of a medicament for the treatment of a fungal infection.

In some embodiments, conditions treated by administration of a provided composition include superficial fungal infections of the skin that appear on the outer layer of skin and can cause *Tinea cruris* (jock itch), *Tinea corporis* (ringworm), *Tinea pedis*, interdigital *Tinea pedis*, moccasin-type *Tinea pedis*, *Tinea manuum*, *Tinea versicolor* (piyriasis), *Tinea nigra*, cutaneous candidiasis, *Tinea faciei* (facial ringworm), and white and black piedra.

*Tinea corporis* (body ringworm), *Tinea cruris* (jock itch), and *Tinea faciei* (facial ringworm), may be caused by *Epidermophyton floccosum*, *Microsporum canis*, *Trichophyton mentagrophytes*, *T. rubrum*, *T. tonsurans*, *T. verrucosum*, and/or *T. violaceum*, and are treatable by the administration of the present compositions.

*Tinea pedis* (athlete's foot) or *Tinea manuum* (fungal infection of the hand), which may be caused *Epidermophyton floccosum*, *Microsporum canis*, *Trichophyton mentagrophytes*, *T. rubrum*, *T. tonsurans*, *T. verrucosum*, and/or *T. violaceum*, are treatable by the administration of the present compositions.

Cutaneous candidiasis, which may be caused by *Candida albicans*, may also be treatable by the administration of the present compositions.

Antifungal agents, for example, naftifine, or a pharmaceutically acceptable salt thereof have fungicidal activity against multiple organisms. Accordingly, the administration of the present compositions may treat, for example, superficial fungal infections of the skin related to or caused by *Epidermophyton floccosum*, *Microsporum canis*, *Microsporum gypseum*, *Trichophyton mentagrophytes*, *T. interdigitale*, *T. rubrum*, *T. soudanense*, *T. tonsurans*, *T. verrucosum*, *T. violaceum*, and *Candida albicans*.

In some embodiments, the present subject matter also relates to a method of treating and/or preventing a fungal infection of the hair follicle, including for example, one or more of *Tinea capitis*, *Tinea favosa*, and *Tinea barbae*, in a mammal comprising administering to a mammal in need thereof an effective amount of presently described gel composition.

In some embodiments, conditions treated by administration of a provided composition include *Tinea capitis* and/or *Tinea favosa* and/or *Tinea barbae*.

*Tinea capitis* and/or *Tinea favosa* and/or *Tinea barbae* are treatable by the administration of a provided composition.

*Tinea capitis* is a superficial fungal infection (dermatophytosis) of the skin of the scalp, eyebrows, and eyelashes, that attacks the hair shaft and follicles. The disease is primarily caused by dermatophytes in the *Trichophyton* and *Microsporum* genera, including for example, *Microsporum audouini*, *Microsporum canis*, *Microsporum Microsporum distortum*, *Microsporum gypseum*, *Trichophyton megninii*, *Trichophyton mentagrophytes*, *Trichophyton rubrum*, *Trichophyton schoenleinii*, *Trichophyton tonsurans*, and *Trichophyton verrucosum*. The clinical presentation is typically a single or multiple patches of hair loss, sometimes with a 'black dot' pattern (often with broken-off hairs), that may be accompanied by inflammation, scaling, pustules, and itching. *Tinea favosa* can be considered a variety of *Tinea capitis* because it involves the scalp. *Tinea favosa* is primarily caused by dermatophytes in the *Trichophyton* and *Microsporum* genera, including for example, *Microsporum gypseum* and *Trichophyton schoenleinii*. *Tinea barbae* is a superficial dermatophytosis that is limited to the bearded areas of the face and neck and occurs almost exclusively in older adolescent and adult males. The clinical presentation of *Tinea barbae* includes inflammatory, deep, kerion-like plaques and non-inflammatory superficial patches resembling *Tinea corporis* or bacterial folliculitis. The mechanism that causes *Tinea barbae* is similar to that of *Tinea capitis*, and is frequently the result of a *Trichophyton rubrum* (*T. rubrum*) infection but may also be the result of *Trichophyton mentagrophytes* var *granulosum* and *Trichophyton verrucosum*. Finally *Microsporum canis* and *Trichophyton mentagrophytes* var *erinacei* have been known to cause *Tinea barbae* but are relatively rare.

*Tinea capitis* which may be caused by one or more of *Microsporum audouini*, *Microsporum canis*, *Microsporum Microsporum distortum*, *Microsporum gypseum*, *Trichophyton megninii*, *Trichophyton mentagrophytes*, *Trichophyton rubrum*, *Trichophyton schoenleinii*, *Trichophyton tonsurans*, and/or *Trichophyton verrucosum*, and *Tinea favosa* which may be caused by one or more of *Microsporum gypseum* and/or *Trichophyton schoenleinii*, and *Tinea barbae* which may be caused by one of more of *Trichophyton rubrum* (*T.*

*rubrum*), *Trichophyton mentagrophytes* var *granulosum*, *Trichophyton verrucosum*, *Microsporum canis* and *Trichophyton mentagrophytes* var *erinacei*, are treatable by the administration of the present compositions.

Antifungal agents, for example, naftifine, or a pharmaceutically acceptable salt thereof have fungicidal activity against multiple organisms. Accordingly, the administration of the present compositions may treat, for example, conditions related to or caused by *Microsporum audouini*, *Microsporum canis*, *Microsporum distortum*, *Microsporum gypseum*, *Trichophyton megninii*, *Trichophyton mentagrophytes* var *granulosum*, *Trichophyton mentagrophytes* var *erinacei*, *Trichophyton rubrum*, *Trichophyton schoenleinii*, *Trichophyton tonsurans*, and/or *Trichophyton verrucosum*.

In some embodiments, the present subject matter relates to a method of treating and/or preventing onychomycosis in a subject comprising administering to a subject in need thereof an effective amount of presently described gel composition.

Non-limiting conditions that are treated by the administration of the present compositions include onychomycosis including onychomycosis caused by one or more of dermatophytes, yeasts (candidal onychomycosis), and non-dermatophyte molds.

Onychomycosis is treatable by the administration of the present compositions.

Onychomycosis is a fungal infection of the nail bed, matrix, and/or or nail plate. It is caused by 3 main classes of fungi: dermatophytes, yeasts (candidal onychomycosis), and nondermatophyte molds. Dermatophytes are the most common cause of onychomycosis. onychomycosis caused by non-dermatophyte molds is becoming more common worldwide. onychomycosis due to *Candida* is less common. Dermatophytes that can cause onychomycosis include one or more of *Trichophyton rubrum*, *Trichophyton interdigitale*, *Epidermophyton floccosum*, *Trichophyton violaceum*, *Microsporum gypseum*, *Trichophyton tonsurans*, *Trichophyton soudanense*, and *Trichophyton verrucosum*, and dermatophyte associated onychomycosis is often also referred to as *tinea ungium*. *Candidal onychomycosis* include cutaneous candidisis and mucocutaneous candidiasis, that are caused by one or more *Candida* species, including for example, *Candida albicans* and *Candida parapsilosis*. Non-dermatophyte molds that can cause onychomycosis can include one or more of, for example, *Scopulariopsis brevicaulis*, *Fusarium* spp., *Aspergillus* spp., *Alternaria*, *Acremonium*, *Scytalidinum dimidiatum*, and *Scytalidinium hyalinum*.

There are four classic types of onychomycosis including the following: distal subungual onychomycosis (DLSO) that is the most common form of onychomycosis, and is usually caused by *Trichophyton rubrum* and/or *Trichophyton interdigitale*, which invades the nail bed and the underside of the nail plate; white superficial onychomycosis (WSO) is caused by fungal (e.g., *T. mentagrophytes*) invasion of the superficial layers of the nail plate to form "white islands" on the plate, nondermatophyte molds cause deep white superficial onychomycosis; proximal subungual onychomycosis (PSO) is fungal penetration of the newly formed nail plate through the proximal nail fold and it is the least common form of onychomycosis in healthy people, but is found more commonly when the patient is immunocompromised; endonyx onychomycosis (EO), and candidal onychomycosis (CO) which is *Candida* species invasion of the fingernails.

Antifungal agents, for example, naftifine, or a pharmaceutically acceptable salt thereof have fungicidal activity against multiple organisms. Accordingly, the administration of the present compositions may treat, for example, conditions, including for example, onychomycosis, related to or caused by one or more dermatophytes, including for example, *Trichophyton rubrum*, *Trichophyton interdigitale*, *Epidermophyton floccosum*, *Trichophyton violaceum*, *Microsporum gypseum*, *Trichophyton tonsurans*, *Trichophyton soudanense*, and *Trichophyton verrucosum*; caused by one or more *Candida* species, including for example, *Candida albicans* and *Candida parapsilosis*; and/or caused by one or more molds, including for example, *Scopulariopsis brevicaulis*, a *Fusarium* spp., a *Aspergillus* spp., *Alternaria*, *Acremonium*, *Scytalidinum dimidiatum*, and *Scytalidinium hyalinum*.

In some embodiments, the present invention provides a gel composition as described above and herein, wherein the composition is combined with a physical/mechanical penetration enhancer that, for example, acts by increasing permeability by reversibly damaging or altering the physicochemical nature of the stratum corneum or nail surface to reduce its diffusional resistance. Such mechanical enhancement can include those known in the art such as manual and electrical nail abrasion, acid etching, ablation by laser, microporation, iontophoresis, application of low-frequency ultrasound, heat or electric currents on/through the nail or skin to make the diffusion of topical moieties more efficient.

Methods of Treating Inflammatory Diseases, Disorders, and Conditions

In some embodiments, the presently described subject matter relates to a method of treating a superficial inflammatory disease, disorder, or condition in a subject, comprising: topically administering to a subject in need thereof a therapeutically effective amount of any presently described topical gel composition useful in treating aninflammatory disease, disorder, or condition of the skin.

Exemplary such inflammatory diseases, disorders, and conditions of the skin include, but are not limited to, atopic dermatitis, psoriasis, eczema, acne, rosacea, and lichenoid disorders.

In some embodiments, treatment of an inflammatory disease (e.g. atopic dermatitis), disorder, or condition of the skin comprises topical administration of a provided gel composition comprising a steroid. Exemplary such steroids are described above. In some embodiments, the steroid is a corticosteroid. In some embodiments, the steroid is fluticasone, or a pharmaceutically acceptable salt thereof. In certain embodiments, the steroid is fluticasone propionate.

In some embodiments, the presently described subject matter relates to the use of a presently described composition to treat a superficial inflammatory disease, disorder, or condition in a subject by topically administering the composition to the subject in need thereof.

In some embodiments, the presently described subject matter relates to the use of a presently described composition to treat atopic dermatitis in a subject by topically administering the composition to the subject in need thereof.

In some embodiments, the presently described subject matter relates to the use of a steroid or a pharmaceutically salt thereof in the manufacture of a medicament for the treatment of a superficial inflammatory disease, disorder, or condition.

In some embodiments, the presently described subject matter relates to the use of fluticasone, or a pharmaceutically salt thereof, in the manufacture of a medicament for the treatment of atopic dermatitis.

Administration

The presently described gel compositions can be topically administered in any formulation, including a gel. A sufficient amount of the topical preparation can be gently rubbed onto the affected area and surrounding skin, for example, in an amount sufficient to cover an affected area plus a margin of healthy skin or tissue surrounding the affected area, for example, a margin of about 0.5 inches. The compositions can be applied to any body surface, including for example, a skin surface, scalp, eyebrows, eyelashes, bearded areas, nail surface, nail bed, nail matrix, and nail fold, as well as to the mouth, vagina, eye, nose, or other mucous membranes.

For most superficial fungal infections of the skin, the composition can be applied in a single, one-time application, once a week, once a bi-week, once a month, or from one to four times daily, for a period of time sufficient to alleviate symptoms or clear the fungal infection, for example, for a period of time of one week, from 1 to 12 weeks or more, from 1 to 10 weeks, from 1 to 8 weeks, from 2 to 12 weeks, from 2 to 10 weeks, from 2 to 8 weeks, from 2 to 6 weeks, from 2 to 4 weeks, from 4 to 12 weeks, from 4 to 10 weeks, from 4 to 8 weeks, from 4 to 6 weeks. The present compositions can be administered, for example, at a frequency of once per day or twice per day. The presently described compositions can be topically administered once per day for a period of time from 1 week to 8 weeks, from 1 week to 4 weeks, for 1 week, for 2 weeks, for 3 weeks, for 4 weeks, for 5 weeks, for 6 weeks, for 7 weeks, or for 8 weeks.

The presently described compositions can be applied in a therapeutically effective amount, for example, an amount sufficient to cover an affected area plus a margin of healthy skin or tissue surrounding the affected area, for example, a margin of about 0.5 inches. Suitable amounts, for example, per application per affected area or cumulative daily dosage per affected area (for example two applications in a 24 hour period), can include, for example, from about 0.1 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

In certain severe cases, for example, of *Tinea pedis* and/or *Tinea cruris*, a maximum per application, per affected area, dose of 8 grams of the presently described composition can be applied to an affected area, for example, once or twice daily.

For example, generally for *Tinea corporis* or *Tinea cruris* or *Tinea faciei*, the present composition can be applied, for example once or twice daily, for example, morning and evening, for about 2-4 weeks. Generally for *Tinea pedis* application the present composition can be applied once daily, for 2 weeks or longer. For example, the presently described compositions can be topically applied in an amount sufficient to cover an affected area plus a margin of healthy skin or tissue surrounding the affected area, for example, a margin of about 0.5 inches, at a frequency, for example, of once a day, for a time period, for example of about two weeks.

If desired, other therapeutic agents can be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

In some embodiments, the pharmaceutical compositions are given in a single or multiple doses per time period, for example, daily, weekly, bi-weekly, or monthly. For example, in some embodiments, the pharmaceutical compositions are given from one to four times per period.

In some embodiments, for superficial fungal infections of the skin, the present compositions are given once per week, for a period of from one to six weeks, for example for one week, for two weeks, for three weeks, for four weeks, five weeks, or for six weeks.

In some embodiments, for onychomycosis infections, the composition are applied at a frequency of from one to four times daily, including for example, once daily, twice daily, three times daily, or four times daily, one a daily or weekly basis, or on a monthly or every other month schedule, for a period of time sufficient to alleviate symptoms or clear the fungal infection, for example, for a period of time of from 1 to 52 weeks, from 1 to 26 weeks, from 26 to 52 weeks, from 13 to 39 weeks, from 20 to 40 weeks, from 20 to 48 weeks, from 5 to 50 weeks, from 10 to 45 weeks, from 15 to 40 weeks, from 20 to 35 weeks, from 25 to 30 weeks, for about 30 weeks; from 28 weeks to 50 weeks, from 30 week to 48 weeks, from 32 to 46 weeks, from 34 to 44 weeks, from 36 to 42 weeks, from 38 to 40 weeks, from 2 to 24 weeks, from 2 to 22 weeks, from 2 to 20 weeks, from 2 to 18 weeks, from 2 to 16 weeks, from 2 to 14 weeks, from 2 to 12 weeks, from 2 to 10 weeks, from 2 to 8 weeks, from 2 to 6 weeks, from 2 to 4 weeks, from 10 to 48 weeks, from 12 to 48 weeks, from 14 to 48 weeks, from 16 to 48 weeks, from 18 to 48 weeks, from 20 to 48 weeks, from 22 weeks to 48 weeks, from 24 week to 48 weeks, from 26 to 48 weeks, from 28 to 48 weeks, from 30 to 48 weeks, from 32 to 48 weeks, from 34 to 48 weeks, from 34 to 48 weeks, from 36 to 48 weeks, from 38 to 48 weeks, from 40 to 48 weeks, from 42 to 48 weeks, from 44 to 48 weeks, from 46 to 48 weeks, for 1 weeks, for 2 weeks, for 4 weeks, for 6 weeks, for 8 weeks, for 10 weeks, for 12 weeks, for 24 weeks, for 26 weeks, for 28 weeks, for 30 weeks, for 32 weeks, for 34 weeks, for 36 weeks, for 38 weeks, for 40 weeks, for 42 weeks, for 44 weeks, for 46 weeks, for 48 weeks, for 50 weeks, for 50 weeks, or for 52 weeks. For example, the present compositions can be topically administered, at a frequency of once per day for a period of time from 1 week to 52 weeks, for example for about from 24 weeks to 48 weeks.

In some embodiments, for onychomycosis infections the presently described compositions are applied in a therapeutically effective amount, for example, an amount sufficient to cover an affected area plus a margin of healthy skin and/or nail surrounding the affected area, for example, a margin of about 0.1 to about 0.5 inches. Suitable amounts, for example, per application per affected area or cumulative daily dosage per affected area (one or more nails and, for example, one or two applications in a 24 hour period), can include, for example, from about 0.1 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

In certain onychomycosis cases a maximum per application, per affected area, dose of 8 grams of the presently described composition is applied to an affected area (all nails), for example, once or twice daily. In some embodiments, the present composition is applied, for example once or twice daily, for example, morning and/or evening, for about 1-52 weeks. For example, in some embodiments, the presently described compositions are topically applied in an amount sufficient to cover an affected area plus a margin of healthy skin and/or nail surrounding the affected area, for example, a margin of about 0.1 to about 0.5 inches, at a frequency, for example, of once a day, for a time period, for example of about 24 to about 48 weeks.

EXEMPLIFICATION

The following examples are illustrative of the present pharmaceutical compositions and are not intended to be limitations thereon.

Example 1

2% Naftifine Hydrochloride Gel

By way of Example 1, a gel formulation comprising 2% naftifine hydrochloride was prepared according to the present invention. The formulation is shown in Table 1 below:

TABLE 1

| Ingredient | % w/w |
|---|---|
| Purified Water USP | 51.06 |
| Polysorbate 20 NF | 5.00 |

TABLE 1-continued

| Ingredient | % w/w |
|---|---|
| Edetate Disodium USP | 0.02 |
| Ethanol | 19.00 |
| Propylene Glycol | 20.00 |
| Naftifine Hydrochloride USP | 2.00 |
| Hydroxyethyl Cellulose | 1.75 |
| Benzyl Alcohol | 1.00 |
| Trolamine | 0.17 |
| Total | 100 |

In order to formulate the gel, three separate phases, i.e., an alcohol phase, a solubilizing agent phase and a water phase, were prepared and combined. More specifically, the alcohol phase was prepared by combining the propylene glycol, ethanol, and benzyl alcohol, which were mixed until uniform. Next, naftifine hydrochloride was added and mixed until dissolved. Hydroxyethyl cellulose was then added and mixed until dispersed.

The solubilizing agent phase was prepared by combining purified water, polysorbate 20 and edetate disodium. The ingredients were mixed until dissolved.

Next, the alcohol phase was combined with the solubilizing agent phase and mixed together to obtain a mixed phase. To the mixed phase, ethanol was added, and the resulting product was mixed.

The water phase was prepared by combining trolamine and purified water and mixing until dissolved. Subsequently, the water phase was combined with mixed phases and the product was mixed until hydrated. After that, the product was deaerated with a counter-rotating mixer to obtain a bulk drug product. The bulk drug product may be transferred to a holding tank and/or packaged.

Example 1a

Alternative 2% Naftifine Hydrochloride Gel

An alternative gel formulation comprising 2% naftifine hydrochloride was prepared according to the present invention. The formulation is shown in Table 1a below:

TABLE 1a.

| Ingredient | % w/w |
|---|---|
| Purified Water USP | 46.85 |
| Polysorbate 80 NF | 5.00 |
| Edetate Disodium USP | 0.02 |
| Ethanol | 44.50 |
| Naftifine Hydrochloride USP | 2.00 |
| Hydroxypropyl Cellulose | 1.50 |
| Diisopropanolamine | 0.13 |
| Total | 100 |

Example 2

2.5% Naftifine Hydrochloride Gel

A gel formulation comprising 2.5% naftifine hydrochloride will be prepared in the same manner as the formulation in Example 1. The formulation is shown in Table 2 below:

TABLE 2

| Ingredient | % w/w |
|---|---|
| Purified Water USP | 50.56 |
| Polysorbate 20 NF | 5.00 |
| Edetate Disodium USP | 0.02 |
| Ethanol | 19.00 |
| Propylene Glycol | 20.00 |
| Naftifine Hydrochloride USP | 2.50 |
| Hydroxyethyl Cellulose | 1.75 |
| Benzyl Alcohol | 1.00 |
| Trolamine | 0.17 |
| Total | 100 |

Example 3

1.5% Naftifine Hydrochloride Gel

A gel formulation comprising 1.5% naftifine hydrochloride will be prepared in the same manner as the formulation in Example 1. The formulation is shown in Table 3 below:

TABLE 3

| Ingredient | % w/w |
|---|---|
| Purified Water USP | 51.56 |
| Polysorbate 20 NF | 5.00 |
| Edetate Disodium USP | 0.02 |
| Ethanol | 19.00 |
| Propylene Glycol | 20.00 |
| Naftifine Hydrochloride USP | 1.50 |
| Hydroxyethyl Cellulose | 1.75 |
| Benzyl Alcohol | 1.00 |
| Trolamine | 0.17 |
| Total | 100 |

Example 4

3.0% Naftifine Hydrochloride Gel

A gel formulation comprising 3.0% naftifine hydrochloride will be prepared in the same manner as the formulation in Example 1. The formulation is shown in Table 4 below:

TABLE 4

| Ingredient | % w/w |
|---|---|
| Purified Water USP | 50.06 |
| Polysorbate 20 NF | 5.00 |
| Edetate Disodium USP | 0.02 |
| Ethanol | 19.00 |
| Propylene Glycol | 20.00 |
| Naftifine Hydrochloride USP | 3.00 |
| Hydroxyethyl Cellulose | 1.75 |
| Benzyl Alcohol | 1.00 |
| Trolamine | 0.17 |
| Total | 100 |

In order to evaluate the gel preparations of Examples 1-3, the following Comparative Examples were prepared.

Comparative Example 1

1% Naftifine Hydrochloride Gel

Comparative Example 1 was prepared in a similar manner to the preparations of Examples 1-3, except that Comparative Example 1 comprises 1% naftifine hydrochloride, a carbomer as thickener instead of a cellulose derivative, and 45.5% w/w ethanol. The formulation of Comparative Example 1 is provided in Table 5 below:

TABLE 5

| Ingredient | % w/w |
|---|---|
| Purified Water USP | 45.48 |
| Naftifine Hydrochloride USP | 1.00 |
| Ethanol | 45.50 |
| Carbomer 934P, NF | 1.50 |
| Polysorbate 80 NF | 5.00 |
| Edetate Disodium USP | 0.02 |
| Diisopropanolamine | 1.50 |
| Total | 100 |

The NDC code for commercially available NAFTIN® Gel, 1% is 40 g NDC 0259-4770-40.

Comparative Example 2

1% Naftifine Hydrochloride Cream

Comparative Example 2 is a commercially available naftifine hydrochloride cream formulation marked as NAFTINO Cream, 1%. The formulation of Comparative Example 2 is provided in Table 6 below:

TABLE 6

| Ingredient |
|---|
| Purified Water USP |
| Polysorbate 60 |
| Isopropyl Myristate |
| Stearyl Alcohol |
| Cetyl Alcohol |
| Cetyl Esters Wax |
| Naftifine Hydrochloride USP |
| Sorbitan Monostearate |
| Benzyl Alcohol |
| Sodium Hydroxide |

The NDC codes for NAFTIN® Cream, 1%, are as follows: 30 g NDC 0259-4126-30; 60 g NDC 0259-4126-60; and 90 g NDC is 0259-4126-90.

Comparative Example 3

2% Naftifine Hydrochloride Cream

Comparative Example 3 is a commercially available naftifine hydrochloride cream formulation marked as NAFTINO Cream, 2%. The formulation of Comparative Example 3 is provided in Table 7 below:

TABLE 7

| Ingredient |
|---|
| Purified Water USP |
| Polysorbate 60 |
| Isopropyl Myristate |
| Stearyl Alcohol |
| Cetyl Alcohol |
| Cetyl Esters Wax |
| Naftifine Hydrochloride USP |
| Sorbitan Monostearate |
| Benzyl Alcohol |
| Sodium Hydroxide |

The NDC code for NAFTINO Cream, 2% is 45 g NDC 0259-1102-45.

Release Assay In Vitro Test

Studies entitled "Characterization of the Release Kinetics of Naftifine using the in vitro Membrane Rate of Release Assay" were conducted under contract by Cetero Research, Pre-Clinical Dermatology Research Laboratory, in Fargo, N. Dak., for MERZ Pharmaceuticals LLC. The studies were designed to determine the relative rates of release of Naftifine from a reference and test formulations, using the FDA's Guidance for Industry—"Non-sterile Semisolid Dosage Forms "Scale-Up and Post-approval Changes: Chemistry, Manufacturing, and Controls; In Vitro Release Testing and In Vivo Bioequivalence Documentation" known as the SUPAC-SS guidance.

Under this SUPAC-SS recommended membrane in vitro rate of release method, each product was tested in sets of 6 diffusion chambers fitted with Supor®-450 membranes (a polyethersulfone membrane). The receptor compartment contained a solution consisting of 52% Ethanol and 48% Water. Six receptor solution aliquots were collected over a period of 6 hours. The aliquots were analyzed for Naftifine content by High Performance Liquid Chromatography with a diode array detector (HPLC-UV). This measurement indicates the rate of membrane diffusion of a topical product, and is seen as an industry standard in vitro method to predict rate of absorption on human skin in vivo following topical application.

Formulations of Comparative Examples 2 and 3

Commercially available naftifine hydrochloride cream formulation marked as NAFTIN® Cream, 1% of Comparative Example 2, and commercially available naftifine hydrochloride cream formulation marked as NAFTIN® Cream, 2% of Comparative Example 3, both include identical amounts of each of the inactive ingredients, i.e., polysorbate 60, isopropyl myristate, stearyl alcohol, cetyl alcohol, cetyl esters wax, sorbitan monostearate, benzyl alcohol, and sodium hydroxide, with the only difference being that the 2% naftifine cream (NAFTIN® Cream, 2%) contains 1% less water than the 1% naftifine cream (NAFTIN® Cream, 1%).

Table 8 shows a comparison of the rate of membrane release of achieved with the 1% (Comparative Example 2) and 2% (Comparative Example 3) Naftifine creams.

TABLE 8

Membrane Rate of Release Regression Slopes ($\mu g/cm^2/hr^{1/2}$)
Referance naftifine 1% cream (Comparative Example 2) vs.
naftitine 2% cream (Comparative Example 3) (n = 6)

| Chamber No. | Naftifine 1% Cream | Chamber No. | Naftifine 2% Cream |
|---|---|---|---|
| 74 | 325.125 | 73 | 331.688 |
| 76 | 203.892 | 75 | 464.125 |
| 78 | 214.711 | 77 | 454.141 |
| 80 | 302.451 | 79 | 435.799 |
| 82 | 328.250 | 81 | 468.310 |
| 84 | 323.728 | 83 | 496.056 |
| Mean ± SD | 283.026 ± 57.932 | Mean ± SD | 441.686 ± 57.372 |
| Mean $r^2$ ± SD | 0.983 ± 0.027 | Mean $r^2$ ± SD | 0.994 ± 0.004 |

As shown in Table 8, the mean rate of membrane release for the naftifine 1% cream was 283 $\mu g/cm^2/hr^{1/2}$. The release rate of the naftifine 2% cream was 442 $\mu g/cm^2/hr^{1/2}$. These results suggest that doubling the active ingredient in the same formulation would result in an almost doubled release rate, i.e., approximately 1.6-fold increase in the release rate.

Formulations of Example 1 or Example 1a and Comparative Example 1

Tables 9a and 9b show a comparison of the rate of membrane release for Comparative Example 1 (NAFTIN Gel 1%), Example 1 (NAFTIN Gel 2%) and Example 1a (Alternative NAFTIN Gel 2%).

TABLE 9a

Membrane Rate of Release Regression Slopes ($\mu g/cm^2/hr^{1/2}$)
Comparative Example 1 vs. Example 1 (n = 6)

| Chamber | Naftifine 1% Gel Comparative Example 1 | Chamber | Naftifine 2% Gel Example 1 |
|---|---|---|---|
| 175 | 345.855 | 177 | 2621.582 |
| 178 | 360.562 | 180 | 3102.955 |
| 181 | 324.761 | 183 | 3099.807 |
| 184 | 376.649 | 186 | 2679.009 |
| 187 | 362.804 | 189 | 3069.425 |
| 190 | 324.698 | 192 | 2928.111 |
| Mean ± SD | 349.221 ± 21.337 | Mean ± SD | 2916.815 ± 216.917 |
| Mean $r^2$ ± SD | 0.996 ± 0.004 | Mean $r^2$ ± SD | 0.987 ± 0.005 |

TABLE 9b

Membrane Rate of Release Regression Slopes ($\mu g/cm^2/hr^{1/2}$)
Comparative Example 1 vs. Example 1a
(Alternative 2% Naftifine Gel) (n = 6)

| Chamber | Naftifine 1% Gel Comparative Example 1 | Chamber | Alternative Naftifine 2% Gel Example 1a |
|---|---|---|---|
| 175 | 345.855 | 176 | 2343.946 |
| 178 | 360.562 | 179 | 2332.724 |
| 181 | 324.761 | 182 | 2307.076 |
| 184 | 376.649 | 185 | 2442.054 |
| 187 | 362.804 | 188 | 2296.518 |
| 190 | 324.698 | 191 | 2247.276 |
| Mean ± SD | 349.221 ± 21.337 | Mean ± SD | 2328.266 ± 65.161 |
| Mean $r^2$ ± SD | 0.996 ± 0.004 | Mean $r^2$ ± SD | 0.996 ± 0.004 |

In complete contrast to the findings demonstrated in the comparison of the Comparative Example 2 and Comparative Example 3 (1% and 2% Naftifine cream products) where doubling the API effectively doubled the rate of release, in the case of the Comparative Example 1 and Example 1, doubling the API in the context of these altered gel formulations increased rate of release by an unexpectedly large amount. Likewise, in the case of the Comparative Example 1 and Example 1a, doubling the API in the context of these altered gel formulations increased rate of release by an unexpectedly large amount.

More specifically, the gel of Comparative Example 1 releases naftifine at a rate of 349 $\mu g/cm^2/hr^{1/2}$. The gel of Example 1, i.e., the formulation with hydroxyethyl cellulose replacing the carbomer and having a reduced alcohol content of 19% the release rate was 2917 $\mu g/cm^2/hr^{1/2}$. The gel of Example 1a, i.e., with hydroxypropyl cellulose replacing the carbomer, had a release rate of 2328 $\mu g/cm^2/hr^{1/2}$*

FIG. 1 is a graphical representation of the results obtained from the release assay in vitro test. As shown in FIG. 1, the gel according to Example 1 exhibited substantially higher naftifine release rates when compared to the gel of Comparative Example 1. Squares are used to denote the Comparative Example 1 gel; triangles are used to denote the Example 1 gel; circles are used to denote the Example 1a gel.

The magnitude of these changes was not expected in view of the relatively small increase resulting from the change in naftifine concentration from 1 to 2% in the cream formulations of Comparative Examples 2 and 3. The improvement is expected to have substantial benefits on the efficiency of delivery of the anti-fungal compound into the skin surface and may therefore also improve the activity and functionality of the product to mediate its antimicrobial activity.

Example 5

In Vivo Maximal Use Study

Initial evaluation of the 2% naftifine gel according to Example 1 was conducted in a Maximal Use Study in humans. The study had the following goals: (1) to quantify the pharmacokinetics of Example 1 in subjects with *Tinea pedis* under maximal use conditions for 2-weeks of once daily applications; (2) to evaluate efficacy of Example 1 after 2-weeks of once daily applications and 2-weeks after last application; to evaluate safety and tolerability of Example 1 throughout the study.

The study was an Open-label, single center, multiple applications to the feet, Phase 1 study designed to quantify the pharmacokinetic (PK) profile in plasma and urine of 2-weeks of once daily application of Example 1.

Maximal use conditions defined as application of a total of 4 grams (2 grams/foot) of Example 1 in the morning for 2-weeks. Example 1 is applied in a thin layer to the affected area plus a margin of about 0.5 inches of healthy skin. PK blood and PK urine samples were obtained on Days 1 and 14 for 24 hours. Efficacy assessments for Example 1 were carried out on Days 7, 15, and 28. Safety evaluation carried out throughout the entire trial.

The study enrolled 32 participants, and all subjects had both feet infected with *Tinea pedis*, 31 (96.9%) subjects had both interdigital and moccasin type of *Tinea pedis*, and 30 (93.8%) subjects completed study. PK and safety data was excellent leading to the conclusions that under conditions of Maximal Use, Example 1 was well tolerated by all subjects.

The most stringent endpoint for anti-fungal products known as the "Complete Cure Rate" is defined as negative mycology results (dermatophyte culture and potassium hydroxide staining (KOH) from a central laboratory and negative clinical signs and symptoms of disease (absence of erythema, scaling, and pruritus)). In *Tinea pedis* which is more difficult to cure than other skin fungal infections the Complete Cure Rate mediated by Comparative Example 3 (2% naftifine cream), ranged from 14.3% in a maximal use Phase 1 study to 17.7% in a more comprehensive Phase 3 study. Surprisingly, the Example 1 (naftifine 2% gel), tested in the same Phase 1 maximal use study mediated a Complete Clinical cure rate of 59.4%, which is substantially greater than any cure rate obtained for naftifine products previously. Since the concentration of active naftifine in the cream and gel is equivalent, therefore the substantially improved clinical efficacy must be due to the formulation improvement of Example 1. Taken together with the evidence obtained from the rate of release studies may indicate that the formulations described herein, for example, the formulations of Examples 1-3, are capable of mediating substantially better clinical effect and antifungal benefits for the patient.

Example 6

Safety and Efficacy Study: Study Design

The formulation described in Example 1 was evaluated in 2 separate 6-week, double-blind, randomized placebo-controlled, multicenter, parallel group phase 3 studies comparing Example 1 to a placebo vehicle in the treatment of *Tinea pedis*. In each study, approximately 850-860 subjects were planned to be enrolled in a 2:1 ratio (Example 1: placebo) so as to obtain approximately 600 (~400:200) evaluable subjects with positive baseline cultures (after accounting for an assumed 30% culture failure during screening).

The objectives of these studies were to evaluate the efficacy and safety of Example 1, applied once daily for 2 weeks, when compared to placebo for 2 weeks in the treatment of subjects with *Tinea pedis* in independent Phase III clinical trials.

In each study, 3 analysis populations were used for summarizing subjects in the trial, depending on whether the summaries were for safety or efficacy purposes. These were: (1) The Safety Evaluation Set (SES) comprised subjects who received study medication at least once (2) The Full Analysis Set (FAS) was the subset of the SES who had positive culture results at baseline and (3) The Per-Protocol Set (PPS) who were comprised of subjects in the FAS who did not have any major protocol deviations during the trial.

In study 1: Eight hundred and fifty nine (859) subjects belonged to the SES, while 613 subjects belonged to the FAS and 509 subjects belonged to the PPS. Two hundred and thirteen (213) FAS subjects had at least one protocol deviation each. There were a total of 330 protocol deviations distributed among these 213 subjects. The most common protocol deviations were the following: Visit 4 out of window (64 occurrences); Visit 3 out of window (35 occurrences); Visit 2 out of window (32 occurrences) and; Visit 3 missed (22 occurrences). One hundred and nine (109) of the 213 FAS subjects did not have a major protocol deviation and therefore were retained in the PPS.

In study 2: Eight hundred and fifty five (855) subjects belonged to the SES, while 561 subjects belonged to the FAS and 436 subjects belonged to the PPS. Two hundred and thirteen (213) FAS subjects had at least one protocol deviation each. There were a total of 125 subjects who were removed from the PPS.

Efficacy Results: Primary Efficacy

The primary efficacy variable was the percentage of subjects in the Example 1 group or placebo group with complete cure of interdigital *Tinea pedis* by Week 6. Complete cure was defined as negative mycology results from the central laboratory (negative dermatophyte culture and negative Potassium Hydroxide (KOH) staining) and absence of erythema, scaling, and pruritus (grade 0 for each).

In order to compare complete cure between the Example 1 treatment group and the placebo treatment group by Week 6, the following one-sided hypothesis test was carried out:

$$H_o(\text{null}): p_1 = p_o \text{ versus } H_1 (\text{alternate}): p_1 > p_o$$

where $p_o$ was the proportion of complete cure in the placebo treatment group and $p_1$ was the proportion of complete cure in the Example 1 treatment group.

The primary efficacy analysis evaluated the superiority of Example 1 over placebo using the general association Cochran-Mantel-Haenszel (CMH) test after stratification by (pooled) clinical site. This test was conducted with the FAS (using the Missing Value Treated as Treatment Failure, MVTF as the primary missing value imputation method) at a one-sided level of significance of $\alpha = 0.025$. The MVTF method for missing primary and most important secondary efficacy variables imputed missing post-baseline data as not having complete cure, mycological cure or treatment effectiveness.

TABLE 10

Primary Efficacy Variable - Complete Cure
By Week 6 (MVTF Imputation)
Full Analysis Set

| Primary Efficacy Variable | Example 1 (N = 400) | Placebo (N = 213) |
|---|---|---|
| Complete Cure | | |
| n (%) | 104 (26.0) | 7 (3.3) |
| p-value [1] <0.0001 | | |

Note: % = (n/N) × 100.
[1] Comparison of complete cure for Example 1 versus Placebo from one-side CMH test with (pooled) site as stratification variable.

TABLE 11

Primary Efficacy Variable - Complete Cure
at Week 6 (MVTF Imputation)
Per-Protocol Set

| Primary Efficacy Variable | Example 1 (N = 329) | Placebo (N = 180) |
|---|---|---|
| Complete Cure | | |
| n (%) | 93 (28.3) | 5 (2.8) |
| p-value [1] <0.0001 | | |

Note: %—(n/N) × 100.
[1] Comparison of complete cure for Example 1 versus Placebo from one-side CMH test with (pooled) site as stratification variable.

For the FAS subjects (using the MVTF missing value imputation method), the complete cure rates in the Example 1 and Placebo treatment groups were 104/400 (26.0%) and 7/213 (3.3%) respectively. The test statistic (CMH) used to compare the proportion of complete cure in Example 1 to that of Placebo proves that Example 1 is statistically superior to Placebo, i.e., the null hypothesis is rejected in favor of the alternate hypothesis. These results are corroborated using the PPS where 93/329 (28.3%) and 5/180 (2.8%) of complete cure in the Example 1 and Placebo treatment groups were obtained.

Very similar positive results were seen in the second identical study. Without recapitulating all results and data, a brief synopsis revealed a Primary Efficacy Variable—Complete Cure at Week 6 (MVTF Imputation) Full analysis set of 64/382 patients ((16.8%) in the Example 1 treated group versus 3/179 patients (1.7%) in the placebo group (p<0.001)). Primary Efficacy Variable—Complete Cure at Week 6 (MVTF Imputation) of the Per Protocol Set (PPS) demonstrated a complete cure in 59/296 (19.9%) in the Example 1 treated group versus 3/140 patients (2.1%) in the Placebo treated group. (p<0.001).

Secondary Efficacy

The secondary efficacy variables were the following: Mycological Cure of interdigital *Tinea pedis* defined as negative KOH result and negative dermatophyte culture by Week 6; and Effective Treatment of interdigital *Tinea pedis* defined as negative KOH, negative culture, and erythema, scaling, and pruritus scores of 0 or 1 by Week 6.

If the test on the primary efficacy variable yielded a statistically significant result (i.e. p=0.025 for a rejection of the null hypothesis to occur), then the most important secondary efficacy variables (mycological cure at Week 6 and effective treatment by week 6) was simultaneously tested applying adjustment for the level of significance a using the Hochberg's step-up procedure (one-sided CMH test at a=0.0125) to evaluate superiority of Formulation 1 over placebo on the FAS (using the MVTF imputation). This sequential testing accounted for multiplicity between the primary efficacy variable (first stage) and the two most important secondary efficacy variables (second stage).

TABLE 12

Secondary Efficacy Variable - Mycological Cure and Treatment Effectiveness by Week 6 (MVTF Imputation) Full Analysis Set

| Secondary Efficacy Variable | Example 1 (N = 400) | Placebo (N = 213) |
|---|---|---|
| Mycological Cure | | |
| n (%) | 235 (58.8) | 22 (10.3) |
| p-value [1] | <0.0001 | |
| Treatment Effectiveness | | |
| n (%) | 203 (50.8) | 15 (7.0) |
| p-value [1] | <0.0001 | |

Note: = (n/N) × 100.
[1] Comparison of mycological cure or treatment effectiveness for Example 1 versus Placebo from one-side CMH test with (pooled) site as stratification variable.

Since the null hypothesis corresponding to the primary efficacy analysis was rejected, the hypotheses corresponding to the secondary efficacy variables (mycological cure and treatment effectiveness) were tested. The CMH test was also used as the test statistic for the comparisons. Both unadjusted and adjusted (using Hochberg's step-up procedure) were used. The unadjusted and Hochberg-adjusted p-values for mycological cure and treatment effectiveness were both statistically significant. Mycological cure rate was 235/400 (58.8%) and 22/213 (10.3%) among subjects in the Example 1 and Placebo treatment groups respectively. Treatment effectiveness was accomplished among 203/400 (50.8%) and 15/213 (7.0%) of subjects in the Example 1 and Placebo treatment groups respectively.

Again, these results were confirmed in the second independent phase III study. To summarize, the Mycological Cure rates and Treatment effectiveness at Week 6 (MTVF Imputation) in the Full Analysis set revealed 250/382 (65.4%) vs. 25/179 (14.0%) mycological cure rates for Example 1 vs. Placebo respectively. Similarly, 207/382 (54.2%) vs. 11/179 (6.1%) Treatment Effectiveness comparing Example 1 to Placebo, respectively. Each of these endpoints demonstrated statistically significance (p>0.001) using a one-sided CMH test with (pooled) site as stratification variable.

Based on these results, a clear improvement in efficacy can be seen to be afforded by Example 1. A direct comparison to Complete Cure rates following identical treatment regimes (QD for 2 weeks application) with Comparative Example 3 conducted as part of phase III clinical studies for the approval of this product resulted in a Complete Cure rate differential of 11.1% between vehicle (placebo) and the Comparative Example 3. In contrast, in the two studies outlined above, Complete Cure Rates from Example 1 were substantially better, generating a Complete Cure average differential of 19% between vehicle (placebo) and Example 1 difference in complete cure rate can be attributed to the difference between the formulation/excipients of Example 1 and Comparative Example 3 since the active naftifine concentrations in both products are identical (2% naftifine hydrochloride).

Efficacy for Moccasin *Tinea Pedis*

Further demonstration of the superiority of the formulation of Example 1 is offered by the clinical data resulting from treatment of Moccasin-type *Tinea pedis*. In the previously outlined study in subjects who had moccasin type *Tinea pedis* in addition to interdigital type *Tinea pedis*, their efficacy is descriptively summarized based on complete cure, mycological cure and treatment effectiveness by Week 6 based on observed data below.

In study 1 Complete cure in the moccasin infected area of the foot was 33/152 (21.7%) and 1/78 (1.3%) following treatment with Example 1 or placebo respectively. Mycological cure was observed among 92/151 (60.9%) and 5/78 (6.4%) subjects in the Example 1 and Placebo treated subjects respectively, in the moccasin affected areas of the foot. Treatment effectiveness was observed among 77/151 (51.0%) and 1/78 (1.3%) subjects in the Example 1 and Placebo treated subjects respectively, in the moccasin affected areas of the foot.

In study 2 Complete cure in the moccasin infected area of the foot was 25/144 (17.4%) and 0/72 (0.0%) following treatment with Example 1 or placebo respectively. Mycological cure was observed among 100/143 (69.9%) and 10/72 (13.9%) subjects in the Example 1 and Placebo treated subjects respectively, in the moccasin affected areas of the foot. Treatment effectiveness was observed among 73/143 (51.0%) and 8/72 (11.1%) subjects in the Example 1 and Placebo treated subjects respectively, in the moccasin affected areas of the foot.

This data is very significant since prior to the present invention there were no known topically administered antifungal agents which achieve any substantial Complete Cure activity in this disease setting.

Indeed, as direct evidence, previous phase III studies with Comparative Example 3 (identical 2% naftifine hydrochloride, cream) demonstrated no effective ability to offer any Complete Cure of Moccasin-type *Tinea pedis*.

Safety

In both of these large clinical studies Example 1 was deemed to be very well tolerated and had an excellent safety profile. The incidence of TEAEs (Treatment-associated adverse events) related to treatment were 12/572 (2.1%) and 9/571 (1.6% compared to 2/287 (0.7%) and 2/284 (0.7%) in the placebo groups of Study 1 and 2 respectively.

In previous clinical trials of the Comparative Example 1, comprising 1% Naftifine Hydrochloride, a carbomer as thickener instead of a cellulose derivative, and 45.5% w/w ethanol, the incidence of Application Site AEs (adverse events) were as follows: burning/stinging (5.0%), itching (1.0%), erythema (0.5%), rash (0.5%), and skin tenderness (0.5%).

In stark contrast, the Application Site AEs associated with Example 1 as recorded in the two phase III clinical studies described herein were remarkably infrequent. In fact, Application Site AEs did not even reach the 1% incidence threshold required for reporting, and less than 1% of patients treated with Example 1 exhibited any of the following symptoms: pain, application site dermatitis, pruritus, dryness, erosion, fissure, paraesthesia, rash, swelling or warmth.

These results indicate that Example 1 was extremely well tolerated during application, and is a major improvement over the previous Comparative Example 1 in terms of an excellent application site safety profile and absence of adverse events when applied to the fungal-affected area.

Conclusion

The primary efficacy objective of this study was met. Example 1 was resoundingly statistically superior to Placebo (p<0.025) in the proportion of subjects attaining complete cure. The results of this study provided clinical evidence that the Example 1 clinical trial had a complete cure of all signs and symptoms in 26% (Study 1) and 17% (Study 2) of patients after 2 weeks treatment (once daily) resulting in a clinical meaningfulness and practical relevance to patients and health care providers. Significant results were also obtained for the most important secondary efficacy variables (mycological cure and treatment effectiveness). Of further importance is the efficacy analysis of subjects with moccasin type *Tinea pedis*. Complete cure among subjects with moccasin-type *Tinea pedis* in the Example 1 group was 22% (Study 1) and 17% (Study 2)—a clinically significant outcome considering that that treatment for moccasin type *Tinea pedis* previously has required an oral anti-fungal medication. Example 1 was well tolerated, generating an AE profile where local application site AEs were less than 1% of the treated population. This absence of application site AEs indicates an extremely well tolerated topical product, and one that appears to be significantly improved over comparative examples 1 and 2. The minimal application site AE profile of this formulation is expected to be very beneficial in the case of active fungal infection where the skin is frequently inflamed, red, and highly sensitive to topical interventions. Such a combination of potent clinical activity and an excellent tolerability profile confirm Example 1 to be unexpectedly superior over existing products.

Example 7

Skin Deposition of Topically Applied Naftifine

Studies were conducted in patients to assess the amount of naftifine available in the stratum corneum following daily topical application of Example 1 (2% Naftifine Gel) and Comparative Example 3 (2% Naftifine Cream) for a period of 14 days.

This was an open-label, intra-subject, single-exposure study on healthy adult male and female subjects comparing the amount of naftifine that was absorbed into the stratum corneum following topical application of the different formulations. Six subjects were treated with the formulation of Example 1 and 6 subjects were treated with the formulation of Comparative Example 3. Individuals who met all inclusion/exclusion criteria were qualified for enrollment into the treatment phase of the study.

Enrolled subjects had a total of twelve 8-cm$^2$ (2 cm×4 cm, long side parallel to spine) test application sites demarcated on the upper back (randomly assigned and as 2 rows of 3 on one side and 2 rows of 3 on the other side of the spine). Of these, a total of 11 sites were dosed with the test formulations once daily (5.001 cm$^2$ or 40 µL per site) for 1 to 14 days. A final site remained untreated to serve as the non-dosed control site. Applications were made using an EPPENDORF repeat dose pipette. The applied dose was then evenly spread and gently rubbed into the test site with a glass rod.

On days 2, 3, 4, 5, 6, 7, 15, 22, 29, 36, and 43, a selected test site was tape stripped (adhesive tape applied to the skin and then removed taking with it a thin layer of the strateum corneum which was then analyzed for content of naftifine). The tape used was Transpore Tape (3M), measuring (nominally) 1"×2" to allow tape stripping of the dosed area including a small margin around the application site. Each tape strip was applied to the test site and gently but firmly pressed with a rubber brayer across the entire site of application for 5 seconds to ensure complete contact. The strip was removed with 1 smooth continuous motion over a 1-2 second duration. After each set of applications (sequential grouped sets of 5, 5, 5, and 5 tape strips) the direction of tape stripping and rolling were reversed (ie, top to bottom, bottom to top). A total of 25 individual sequential fresh strips were applied to each test site. The sequential sets of strips (1-5, 6-10, 11-15, 16-20, and 21-25) were placed into pre-labeled glass vials and sealed following collection. At the completion of each study day's activity, the vials were transferred and stored at −20° C. until processed by the analytical laboratory. The tape strips from each side were processed and quantified for amount of naftifine present. This study was designed to determine the amount of naftifine that penetrated into the stratum corneum from 1 to 14 days of application, and its elimination from the stratum corneum over 28 days following the last dose application. The quantification of naftifine present in the stratum corneum tape strip samples was measured using extraction and analytical methods developed for these samples, and according to Cetero Research Analytical Laboratory's Standard Operating Procedures and FDA Guidelines.

Table 13 shows a comparison of the rate deposition of naftifine into the skin of patients following once-daily dosing of Example 1 (2% Naftifine Hydrochloride Gel) and Comparative Example 3 (2% Naftifine Hydrochloride Cream) onto the skin for a period of 14 days. These pharmacokinetic results represent the Mean and Standard Deviation results by treatment of total recovered naftifine from the tape strip samples normalized to area dosed (ng/mL).

TABLE 13

Skin Deposition Rates of Naftifine (ng/mL) comparing the formulation of Example 1 (2% Naftifine Hydrochloride Gel) and the formulation of Comparative Example 3 (2% Naftifine Hydrochloride Cream) following once-daily application for a period of 14 days (N = 6 patients per sample group)

| Day | Naftifine 2% Cream Comparative Example 3 | Naftifine 2% Gel Example 1 |
| --- | --- | --- |
| 1 | 0.097 ± 0.212 | 0.009 ± 0.011 |
| 2 | 762.67 ± 874.96 | 1150.65 ± 1976.45 |
| 3 | 1045.47 ± 1823.31 | 1509.98 ± 2421.35 |
| 4 | 281.49 ± 310.64 | 751.73 ± 908.97 |
| 5 | 254.24 ± 338.08 | 831.31 ± 888.05 |
| 6 | 151.70 ± 121.89 | 457.49 ± 552.38 |
| 7 | 161.63 ± 221.87 | 534.15 ± 512.86 |
| 15 | 321.63 ± 245.90 | 199.97 ± 172.83 |
| 22 | 159.98 ± 231.79 | 126.39 ± 212.22 |
| 29 | 66.60 ± 157.38 | 5.45 ± 5.08 |
| 36 | 20.97 ± 29.28 | 128.62 ± 201.11 |
| 43 | 2.87 ± 3.39 | 20.30 ± 28.98 |

With regard to safety results, no serious adverse events were reported over the course of this study. Overall, the most common adverse events reported were application site pain and application site pruritus attributable to site tape stripping. Application site pain was reported on 1 occasion by 3 (3/12) subjects (25.0%) but was considered by the Investigator to be not related to the test products. Application site pruritus was reported on at least 1 occasion by 2 (2/12) subjects (16.7%) and was considered by the Investigator to be related to the test products on 1 occasion and not related to the test products on 2 occasions.

As shown in Table 13, the data indicate the presence of naftifine in the tape strips on all sample collection days. However, the amount of naftifine recovered from the tape strips was higher following treatment with Example 1 (naftifine 2% gel) from Day 2 to 7 and from Day 36 to 43, while the amount of naftifine recovered from the tape strips was slightly higher following treatment with Comparative Example 3 (naftifine 2% cream) from Day 15 to 29. The maximum amount of naftifine HCl recovered in the tape strips occurred on Day 3 for both test articles before decreasing (despite continuation of dosing through Day 14) through the remaining duration of study conduct (Day 43).

Both with Example 1 (naftifine 2% gel) and Comparative Example 3 (naftifine 2% cream) were well tolerated as single daily site applications of 5.0 µL/cm2 (40 µL total/8 cm² site) applied topically to healthy adult subjects for 1 to 14 consecutive days.

In conclusion, these data demonstrate that the rate with which the active naftifine agent is deposited into the skin of a patient is more rapid/efficient when delivered via Example 1 (naftifine 2% gel) compared to Comparative Example 3 (naftifine 2% cream), and this difference in the efficiency of delivery can be solely attributed to inherent difference in the formulation of the delivery vehicle.

Example 8

Corticosteroid Gel Formulations

The following Tables provide examples of fluticasone formulations.

TABLE 24

Fluticasone Formulation

| Ingredient | Formula % |
|---|---|
| Active Ingredients: | |
| Fluticasone Propionate | 0.025 |
| Also contains: | |
| Water | 66.71 |
| Propylene Glycol | 20.0 |
| Ethanol | 5.0 |
| Polysorbate 20 | 5.0 |
| Hydroxyethyl Cellulose | 1.75 |
| Benzyl alcohol | — |
| Disodium EDTA | 0.02 |
| Transcutol (ethoxydiglycol) | 1.5 |
| | 100.00 |
| pH | 5.43 |

TABLE 25

Fluticasone Formulation

| Ingredient | Formula % | Formula % |
|---|---|---|
| Active Ingredients: | | |
| Fluticasone Propionate | 0.05 | 0.025 |
| Also contains: | | |
| Water | 53.18 | 53.21 |
| Propylene Glycol | 20.0 | 20.0 |
| Ethanol | 19.0 | 19.0 |
| Polysorbate 20 | 5.0 | 5.0 |
| Hydroxyethyl Cellulose | 1.75 | 1.75 |
| Benzyl alcohol | 1.00 | 1.00 |
| Disodium EDTA | 0.02 | 0.02 |
| | 100.00 | 100.00 |
| pH | 5.5 | 5.49 |

TABLE 26

Fluticasone Formulation

| Ingredient | Formula % | Formula % |
|---|---|---|
| Active Ingredients: | | |
| Fluticasone Propionate | 0.025 | 0.025 |

TABLE 26-continued

Fluticasone Formulation

| Ingredient | Formula % | Formula % |
|---|---|---|
| Also contains: | | |
| Water | 71.71 | 65.21 |
| Propylene Glycol | 20.0 | 20.0 |
| Ethanol | — | 8.0 |
| Polysorbate 20 | 5.0 | 5.0 |
| Hydroxyethyl Cellulose | 1.75 | 1.75 |
| Benzyl alcohol | — | — |
| Disodium EDTA | 0.02 | 0.02 |
| Transcutol (ethoxydiglycol) | 1.5 | — |
| | 100.00 | 100.00 |
| pH | 5.78 | 5.43 |

TABLE 27

Fluticasone Propionate Gel

| | A | B |
|---|---|---|
| Active Ingredients: | | |
| Fluticasone Propionate | 0.05 | 0.025 |
| Also contains: | | |
| Ethanol | NA | NA |
| Benzyl Alcohol | 1.00 | 1.00 |
| Edetate Disodium | 0.02 | 0.02 |
| Hydroxyethyl Cellulose | 1.75 | 1.75 |
| Disodium EDTA | 0.02 | 0.02 |
| Polysorbate | 5.00 | 5.00 |
| Propylene Glycol | 41.00 | 41.025 |
| Purified Water | 51.01 | 51.01 |
| Trolamine | 0.17 | 0.17 |
| pH | 8.17 | 8.01 |
| Viscosity (#6 @ 10 rpm) | 65,300 cP | 62,900 cP |

NOTE: pH before Trolamine addition for all samples was approximately pH 5.4-5.5

TABLE 28

Fluticasone Formulation

| Ingredient | Formula % |
|---|---|
| Active Ingredients: | |
| Fluticasone Propionate | 0.025 |
| Also contains: | |
| Water | 73.21 |
| Propylene Glycol | 20.0 |
| Ethanol | — |
| Polysorbate 20 | 5.0 |
| Hydroxyethyl Cellulose | 1.75 |
| Benzyl alcohol | — |
| Disodium EDTA | 0.02 |
| Transcutol (ethoxydiglycol) | — |
| | 100.00 |

Preliminary stability studies demonstrate that the formulations shown in Tables 24, 25, and 26 are stable for up to one month at ambient temperature (ca. 22° C.), for at least one week at elevated temperatures (ca. 50° C.), and for at least one week at lowered temperatures (ca. to 8° C.).

Release Assay In Vitro Test

Under this SUPAC-SS recommended membrane in vitro rate of release method, each product is tested in sets of 6 diffusion chambers fitted with Supor®-450 membranes (a polyethersulfone membrane). The receptor compartment contains a solution consisting of an amount of Ethanol and an amount of Water. Six receptor solution aliquots are collected over a period of 6 hours. The aliquots are analyzed for fluticasone content by High Performance Liquid Chromatography with a diode array detector (HPLC-UV). This measurement indicates the rate of membrane diffusion of a topical product, and is seen as an industry standard in vitro method to predict rate of absorption on human skin in vivo following topical application.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A gel composition for topical administration consisting essentially of:
   (i) naftifine or a pharmaceutically acceptable salt thereof, present in an amount of from about 0.5 wt % to about 4 wt %;
   (ii) a first solvent which is a glycol solvent, present in an amount of from about 10 wt % to about 25 wt %;
   (iii) a second solvent which is an alkyl alcohol solvent, present in an amount of from about 10 wt % to about 25 wt %;
   (iv) a non-carbomer rheology modifier selected from a hydroxy cellulose, present in an amount of from about 0.75 wt % to about 2.25 wt %;
   (v) a polysorbate solubilizing agent present in an amount of from about 3 wt % to about 8 wt %;
   (vi) a pH adjuster selected from an amine base; and
   optionally one or more of: water, a preservative, a chelating agent, a coloring agent, and a fragrance,
wherein the gel composition has a pH of about 4.5 to about 6.0.

2. The gel composition of claim 1, wherein the naftifine or a pharmaceutically acceptable salt thereof is present in an amount of from about 1.0 wt % to about 3.0 wt %.

3. The gel composition of claim 1, wherein the glycol solvent is present in an amount of about 18 wt % to about 22 wt %.

4. The gel composition of claim 3, wherein the glycol solvent is propylene glycol.

5. The gel composition of claim 1, wherein the alkyl alcohol is present in an amount of from about 17 wt % to about 22 wt %.

6. The gel composition of claim 5, wherein the alkyl alcohol is ethanol.

7. The gel composition of claim 1, wherein the hydroxy cellulose is hydroxyethyl cellulose.

8. The gel composition of claim 1, wherein the polysorbate solubilizing agent is Polysorbate 20.

9. The gel composition of claim 1, wherein the polysorbate solubilizing agent is Polysorbate 80.

10. The gel composition of claim 1, wherein the naftifine, or pharmaceutically acceptable salt thereof, is naftifine hydrochloride.

11. The gel composition of claim 1, wherein the naftifine, or a pharmaceutically acceptable salt thereof, is present in an amount of about 2.0 wt %, the glycol solvent is present in an amount of about 20 wt %, the alkyl alcohol solvent is present in an amount of about 19 wt %, the non-carbomer rheology modifier is present in an amount of about 1.75 wt %, and the polysorbate solubilizing agent is present in an amount of about 5 wt %.

12. The gel composition of claim 11, wherein the glycol solvent is propylene glycol.

13. The gel composition of claim 11, wherein the alcohol solvent is ethanol.

14. The gel composition of claim 11, wherein the non-carbomer rheology modifier is hydroxyethyl cellulose.

15. The gel composition of claim 11, wherein the polysorbate solubilizing agent is Polysorbate 20 or Polysorbate 80.

16. The gel composition of claim 11, wherein the naftifine or pharmaceutically acceptable salt thereof is naftifine hydrochloride.

17. The gel composition of claim 1, consisting essentially of 2.0 wt % naftifine hydrochloride, about 20 wt % propylene glycol, about 19 wt % ethanol, about 5 wt % Polysorbate 20, about 1.75 wt % hydroxyethyl cellulose, about 1.0 wt % benzyl alcohol, about 0.17 wt % trolamine, about 0.02 wt % ethylenediaminetetracetic acid or a salt thereof, water, and optionally one or more of a coloring agent and a fragrance.

* * * * *